(12) United States Patent
Yang et al.

(10) Patent No.: US 10,080,484 B2
(45) Date of Patent: Sep. 25, 2018

(54) MULTISPECTRAL WIDE-FIELD ENDOSCOPIC IMAGING OF FLUORESCENCE

(71) Applicant: University of Washington, Seattle, WA (US)

(72) Inventors: Chenying Yang, Seattle, WA (US); Eric J. Seibel, Seattle, WA (US); Leonard Y. Nelson, Seattle, WA (US); Timothy D. Soper, San Jose, CA (US)

(73) Assignee: University of Washington, Seattle, WA (US)

( * ) Notice: Subject to any disclaimer, the term of this patent is extended or adjusted under 35 U.S.C. 154(b) by 647 days.

(21) Appl. No.: 14/611,015

(22) Filed: Jan. 30, 2015

(65) Prior Publication Data

US 2015/0216398 A1     Aug. 6, 2015

Related U.S. Application Data

(60) Provisional application No. 61/934,479, filed on Jan. 31, 2014.

(51) Int. Cl.
  *A61B 6/00* (2006.01)
  *A61B 1/04* (2006.01)
  (Continued)

(52) U.S. Cl.
  CPC .......... *A61B 1/043* (2013.01); *A61B 1/00009* (2013.01); *A61B 1/00165* (2013.01); *A61B 1/00172* (2013.01); *G01J 3/0208* (2013.01); *G01J 3/0218* (2013.01); *G01J 3/06* (2013.01); *G01J 3/10* (2013.01); *G01J 3/28* (2013.01); *G01J 3/36* (2013.01); *G01J 3/4406* (2013.01); *G01N 21/6456* (2013.01); *G01N 21/6486* (2013.01); *G02B 23/26* (2013.01); *G01J 3/0278* (2013.01); *G01J 2003/065* (2013.01); *G01N 21/278* (2013.01); *G01N 21/474* (2013.01);
  (Continued)

(58) Field of Classification Search
  CPC . A61B 1/043; A61B 1/00009; A61B 1/00165; A61B 1/00172; G02B 23/26; G01N 21/6456; G01N 2201/08; G01N 2201/12
  See application file for complete search history.

(56) References Cited

U.S. PATENT DOCUMENTS 4,479,449 A   10/1984   Alfano
RE31,815 E    1/1985    Alfano
(Continued)

OTHER PUBLICATIONS

D. Spitzer et al., "The Absorption and Scattering of Light in Bovine and Human Dental Enamel," Calcified Tissue Research, 17(2):129-137 (1975).
(Continued)

*Primary Examiner* — Mallika D Fairchild
(74) *Attorney, Agent, or Firm* — Christensen O'Connor Johnson Kindness PLLC

(57) ABSTRACT

Improved methods, systems and apparatus relating to wide field fluorescence and reflectance imaging are provided, including improved methods, systems and apparatus relating to removal of background signals such as autofluorescence and/or fluorophore emission cross-talk; distance compensation of fluorescent signals; and co-registration of multiple signals emitted from three dimensional tissues.

23 Claims, 56 Drawing Sheets

(51) Int. Cl.
| | |
|---|---|
| G02B 23/26 | (2006.01) |
| G01N 21/64 | (2006.01) |
| A61B 1/00 | (2006.01) |
| G01J 3/06 | (2006.01) |
| G01J 3/10 | (2006.01) |
| G01J 3/28 | (2006.01) |
| G01J 3/36 | (2006.01) |
| G01J 3/44 | (2006.01) |
| G01N 21/27 | (2006.01) |
| G01N 21/47 | (2006.01) |
| G01J 3/02 | (2006.01) |

(52) U.S. Cl.
CPC .............. *G01N 2021/4742* (2013.01); *G01N 2021/6417* (2013.01); *G01N 2021/6419* (2013.01); *G01N 2021/6484* (2013.01)

(56) References Cited

U.S. PATENT DOCUMENTS

| | | |
|---|---|---|
| 4,515,476 A | 5/1985 | Ingmar |
| 5,345,941 A | 9/1994 | Rava et al. |
| 5,382,163 A | 1/1995 | Putnam |
| 5,413,108 A | 5/1995 | Alfano |
| 5,450,293 A | 9/1995 | Hoffman |
| 5,483,951 A | 1/1996 | Frassica et al. |
| 5,816,676 A | 10/1998 | Koenen Meyers et al. |
| 6,024,562 A | 2/2000 | Hibst et al. |
| 6,186,780 B1 | 2/2001 | Hibst et al. |
| 6,231,338 B1 | 5/2001 | de Josselin de Jong et al. |
| 6,294,775 B1 | 9/2001 | Seibel et al. |
| 6,563,105 B2 | 5/2003 | Seibel et al. |
| 6,584,341 B1 | 6/2003 | Mandelis et al. |
| 6,615,068 B1 | 9/2003 | Alfano et al. |
| 6,821,116 B2 | 11/2004 | Severance |
| 6,975,898 B2 | 12/2005 | Seibel |
| 7,475,821 B2 | 1/2009 | Barkan et al. |
| 7,942,814 B2 | 5/2011 | Remijan et al. |
| 7,955,076 B2 | 6/2011 | Yamagishi |
| 8,027,709 B2 | 9/2011 | Arnone et al. |
| 8,182,479 B2 | 5/2012 | Schneider |
| 8,184,147 B2 | 5/2012 | Crucs et al. |
| 8,224,045 B2 | 7/2012 | Burns et al. |
| 8,285,039 B2 | 10/2012 | Komiya |
| 8,371,848 B2 | 2/2013 | Okawa et al. |
| 8,556,625 B2 | 10/2013 | Lovely |
| 8,992,216 B2 | 3/2015 | Karazivan |
| 9,060,690 B2 | 6/2015 | Liang et al. |
| 2004/0220498 A1 | 11/2004 | Li et al. |
| 2004/0240716 A1 | 12/2004 | de Josselin de Jong et al. |
| 2005/0202363 A1 | 9/2005 | Osterwalder |
| 2007/0134615 A1 | 6/2007 | Lovely |
| 2008/0248447 A1 | 10/2008 | Karazivan |
| 2009/0055024 A1 | 2/2009 | Kay |
| 2011/0090513 A1 | 4/2011 | Seidl et al. |
| 2011/0117025 A1 | 5/2011 | Dacosta et al. |
| 2012/0326055 A1* | 12/2012 | Wilson ................ A61B 5/0059 250/459.1 |
| 2013/0323674 A1 | 12/2013 | Hakomori et al. |
| 2015/0005596 A1 | 1/2015 | Wilzbach |
| 2015/0010878 A1 | 1/2015 | Seibel et al. |
| 2015/0216398 A1 | 8/2015 | Yang et al. |

OTHER PUBLICATIONS

JBD Featherstone et al., "A Mechanism for Dental Caries Based on Chemical Processes and Diffusion Phenomena During In-Vitro Caries Simulation on Human Tooth Enamel," Archives of Oral Biology, 24(2):101-112 (1979).
Sa Prahl et al., "A Monte Carlo Model of Light Propagation in Tissue," SPIE Proceedings of Dosimetry of Laser Radiation in Medicine and Biology, IS 5:102-111 (1989).
L. Giniunas et al., "Endoscope With Optical Sectioning Capability," Applied Optics, 32(16):2888-2890 (1993).
D. Fried et al., "Nature of Light Scattering in Dental Enamel and Dentin at Visible and Near-Infrared Wavelengths," Applied Optics, 34(7):1278-1285 (1995).
LH Wang et al., "MCML—Monte Carlo Modeling of Photon Transport in Multi-Layered Tissues," Computer Methods and Programs in Biomedicine, 47(2):131-146 (1995).
JR Zijp et al., "HeNe-Laser Light Scattering by Human Dental Enamel," Journal of Dental Research, 74(12):1891-1898 (1995).
OM Winn et al., "Coronal and Root Caries in the Dentition of Adults in the United States, 1988-1991," Journal of Dental Research, 75:642-651 (1996).
KJ Anusavice., "Management of Dental Caries as a Chronic Infectious Disease," Journal of Dental Education, 62(10):791-802 (1998).
BW Colston Jr et al., "Dental OCT," Optics Express, 3(6):230-238 (1998).
BW Colston Jr et al., "Imaging of Hard- and Soft-Tissue Structure in the Oral Cavity by Optical Coherence Tomography," Applied Optics, 37(16):3582-3585 (1998).
KR Ekstrand et al., "Detection, Diagnosing, Monitoring and Logical Treatment of Occlusal Caries in Relation to Lesion Activity and Severity. An in Vivo Examination With Histological Validation," Caries Research, 32(4):247-254 (1998).
F. Feldchtein et al., "In Vivo OCT Imaging of Hard and Soft Tissue of the Oral Cavity," Optics Express, 3(6):239-250 (1998).
Ferreira Zandona et al., "Laser Fluorescence Detection of Demineralization in Artificial Occlusal Fissures," Caries Research, 32(1):31-40 (1998).
AG Almeida et al., "Future Caries Susceptibility in Children With Early Childhood Caries Following Treatment Under General Anesthesia," Pediatric Dentistry, 22(4):302-306 (2000).
FLL Otis et al., "Optical Coherence Tomography: A New Imaging Technology for Dentistry," Journal of the American Dental Association, 131(4):511-514 (2000).
C. Robinson et al., "The Chemistry of Enamel Caries," Critical Reviews in Oral Biology and Medicine, 11(4):481-495 (2000).
J. Bush et al., "All-Fiber Optic Coherence Domain Interferometric Techniques," Fiber Optic Sensor Technology II, 4204:71-80 (2001).
J. Knittel et al., "Endoscope-Compatible Confocal Microscope Using a Gradient Index-Lens System," Optics Communications, 188(5-6):267-273 (2001).
P. Niederer et al., "Image Quality of Endoscopes," Biomonitoring and Endoscopy Technologies, Proceedings of SPIE, 4158:1-10 (2001).
EJ Seibel et al., "'Single Fiber Flexible Endoscope: General Design for Small Size, High Resolution, and Wide Field of View," Biomonitoring and Endoscopy Technologies, Proceedings of SPIE, 4158:29-39 (2001).
QYJ Smithwick et al., "Control Aspects of the Single Fiber Scanning Endoscope,"' Optical Fibers and Sensors for Medical Applications, Proceedings of SPIE, 4253:176-188 (2001).
Me Fauver et al., "Microfabrication of Fiber Optic Scanners," Optical Scanning 2002, Proceedings of SPIE, 4773:102-110 (2002).
D Fried et al., "Imaging Caries Lesions and Lesion Progression With Polarization Sensitive Optical Coherence Tomography," Journal of Biomedical Optics, 7(4):618-627 (2002).
D. Fried et al., "Imaging Caries Lesions and Lesion Progression With Polarization-Sensitive Optical Coherence Tomography," Lasers in Dentistry VIII, 4610:113-124 (2002).
RS Jones et al., "Attenuation of 1310- and 1550-nm Laser Light Through Sound Dental Enamel," Lasers in Dentistry VIII, 4610:187-190 (2002).
EJ Seibel et al., "Prototype Scanning Fiber Endoscope," Optical Fibers and Sensors for Medical Applications II, Proceedings of the SPIE, 4616:173-179 (2002).
EJ Seibel et al., "Unique Features of Optical Scanning, Single Fiber Endoscopy," Lasers in Surgery and Medicine, 30(3):177-183 (2002).
QYJ Smithwick et al., "Depth Enhancement Using a Scanning Fiber Optical Endoscope," Optical Biopsy IV, Proceedings of SPIE, 4613:222-233 (2002).
N Tinanoff et al., "Clinical Decision Making for Caries Management in Children," Pediatric Dentistry, 24(5):386-392 (2002).

(56) References Cited

OTHER PUBLICATIONS

AI Ismail, "Determinants of Health in Children and the Problem of Early Childhood Caries," Pediatric Dentistry, 25(4):328-333 (2003).
RS Jones et al., "Near-Infrared Transillumination at 1310-nm for the Imaging of Early Dental Decay," Optics Express, 11(18):2259-2265 (2003).
RO Rocha et al., "In Vivo Effectiveness of Laser Fluorescence Compared to Visual Inspection and Radiography for the Detection of Occlusal Caries in Primary Teeth," Caries Research, 37(6):437-441 (2003).
JD Bader et al., "A Systematic Review of the Performance of a Laser Fluorescence Device for Detecting Caries," Journal of the American Dental Association, 135(10):1413-1426 (2004).
K Carter et al., "Automated Quantification of Dental Plaque Accumulation Using Digital Imaging," Journal of Dentistry, 32(8):623-628 (2004).
PR Gomes et al., "Dental Caries in Paulinia, Sao Paulo State, Brazil, and WHO Goals for 2000 and 2010," Cad Saude Publica, 20(3):866-870 (2004).
GC Jones et al., "Transillumination of Interproximal Caries Lesions with 830-nm Light," Lasers in Dentistry X, 5313:17-22 (2004).
RS Jones et al., "Imaging Artificial Caries Under Composite Sealants and Restorations," Journal of Biomedical Optics, 9(6):1297-1304 (2004).
CM Bühler et al., "Imaging of Occlusal Dental Caries (Decay) with Near-IR Light at 1310-nm," Optics Express, 13(2):573-582 (2005).
D Fried et al., "Early Caries Imaging and Monitoring With Near-Infrared Light," Dental Clinics of North America, 49(4):771-793 (2005).
JC Hamilton "Should a Dental Explorer Be Used to Probe Suspected Lesions?" Journal of the American Dental Association, 136(11):1526-1532 (2005).
RS Jones et al., "The Effect of High-Index Liquids on PS-OCT Imaging of Dental Caries," Lasers in Dentistry XI, 5687:34-41 (2005).
P Ngaotheppitak et al., "Measurement of the Severity of Natural Smooth Surface (Interproximal) Caries Lesions with Polarization Sensitive Optical Coherence Tomography," Lasers in Surgery and Medicine, 37(1):78-88 (2005).
CM Brown et al., "Optomechanical Design and Analysis for a Scanning Fiber Endoscope," Proceedings of the 2001 ASME International Mechanical Engineering Congress and Exposition, 51:165-166 (2006).
CL Darling et al., "Light Scattering Properties of Natural and Artificially Demineralized Dental Enamel at 1310 nm," Journal of Biomedical Optics, 11(3):034023 (2006).
EK Delgado-Angulo et al., "Influence of Host Related Indicators on Dental Caries in the Permanent Dentition," Acta Odontal Latinoam, 19(2):85-92 (2006).
RS Jones et al., "Remineralization of Enamel Caries Can Decrease Optical Reflectivity," Journal of Dental Research, 85(9):804-808 (2006).
RS Jones et al., "Imaging Artificial Caries on the Occlusal Surfaces With Polarization-Sensitive Optical Coherence Tomography," Caries Research, 40(2):81-89 (2006).
RS Jones et al., "Remineralization of In Vitro Dental Caries Assessed With Polarization-Sensitive Optical Coherence Tomography," Journal of Biomedical Optics, 11(1):014016-1-9 (2006).
P Ngaotheppitak et al., "PS-OCT of Occlusal and Interproximal Caries Lesions Viewed From Occlusal Surfaces," Lasers in Dentistry X, 6137:61370L-1-8 (2006).
T Al et al., "Risk Indicators for Childhood Caries in Taiwan," Community Dentistry and Oral Epidemiology, 34(6):437-445 (2006).
AF Zandona et al., "Diagnostic Tools for Early Caries Detection," Journal of the American Dental Association, 137(12):1675-1684 (2006).
SL Chong et al., "Nondestructive Measurement of the Inhibition of Demineralization on Smooth Surfaces Using Polarization-Sensitive Optical Coherence Tomography," Lasers in Surgery and Medicine, 39(5):422-427 (2007).

M Du et al., "Caries in Preschool Children and Its Risk Factor in 2 Provinces in China," Quintessence International, 38(2):143-151 (2007).
D Fried et al.,"Polarization Sensitive Optical Coherence Tomography for Quantifying the Severity of Natural Caries Lesions on Occlusal Surfaces," Lasers in Dentistry XIII, 6425:64250U-1-8 (2007).
JS Greenspan et al., "A Global Theme—Poverty and Human Development," Journal of Dental Research, 86(10):917-918 (2007).
S Naidoo et al., "Nutrition, Oral Health and the Young Child," Maternal and Child Nutrition, 3(4):312-321 (2007).
HD Sgan-Cohen et al., "Health, Oral Health and Poverty," Journal of the American Dental Association, 138(11):1437-1442 (2007).
E Barberia et al., "A Clinical Study of Caries Diagnosis With a Laser Fluorescence System," Journal of the American Dental Association, 139(5):572-579 (2008).
K Hirasuna et al., "Near-Infrared Imaging of Developmental Defects in Dental Enamel," Journal of Biomedical Optics, 13(4):044011-1-7 (2008).
JA Rodrigues et al., "The Influence of Zero-Value Subtraction on the Performance of Two Laser Fluorescence Devices for Detecting Occlusal Caries in Vivo," Journal of the American Dental Association, 139(8):1105-1112 (2008).
B Valera et al., "Comparison of Visual Inspection, Radiographic Examination, Laser Fluorescence and Their Combinations on Treatment Decisions for Occlusal Surfaces," American Journal of Dentistry, 21(1):25-29 (2008).
L Coulthwaite et al., "Evaluation of in Vivo Denture Plaque Assessment Methods," British Dental Journal, 207(6):E12, 6 pages (2009).
L Coulthwaite et al., "QLF is Not Readily Suitable for in Vivo Denture Plaque Assessment," Journal of Dentistry, 37(11):898-901 (2009).
JD Featherstone., "Remineralization, the Natural Caries Repair Process—the Need for New Approaches," Advances in Dental Research, 21(1):4-7 (2009).
LE Kagihara et al., "Assessment, Management, and Prevention of Early Childhood Caries," Journal of the American Academy of Nurse Practitioners, 21(1):1-10 (2009).
C Lee et al., "Non-Destructive Measurement of Demineralization and Remineralization in the Occlusal Pits and Fissures of Extracted 3rd Molars with PS-OCT," Lasers in Dentistry XV, 7162:71620V-1-6 (2009).
C Lee et al., "Polarization-Sensitive Optical Coherence Tomographic Imaging of Artificial Demineralization on Exposed Surfaces of Tooth Roots," Dental Materials, 25(6):721-728 (2009).
D Lee et al., "Near-IR Multi-Modal Imaging of Natural Occlusal Lesions," Lasers in Dentistry XV, 7162:71620X-1-7 (2009).
CH Silva-Lovato et al., "Evaluation of a Computerized Method for Denture Biofilm Quantification: Inter-Examiner Reproducibility," Journal of Prosthodontics, 18(4):332-336 (2009).
SK Manesh et al., "Nondestructive Assessment of Dentin Demineralization Using Polarization-Sensitive Optical Coherence Tomography After Exposure to Fluoride and Laser Irradiation," Journal of Biomedical Materials Research B: Applied Biomaterials, 90(2):802-812 (2009).
SK Manesh et al., "Polarization-Sensitive Optical Coherence Tomography for the Nondestructive Assessment of the Remineralization of Dentin," Journal of Biomedical Optics, 14(4):044002-1-6 (2009).
SM Douglas et al., "Imaging Natural Occlusal Caries Lesions With Optical Coherence Tomography," Lasers in Dentistry XVI, 7549:75490N-1-7 (2010).
D Fried., "Lasers and Optics Measuring Tooth Decay," Optics & Photonics News, pp. 15-19 (2010).
C Lee et al., "In Vitro Near-Infrared Imaging of Occlusal Dental Caries Using a Germanium-Enhanced CMOS Camera," Lasers in Dentistry XVI, 7549:75490K-1-7 (2010).
C Lee et al., "Nondestructive Assessment of the Severity of Occlusal Caries Lesions With Near-Infrared Imaging at 1310 NM," Journal of Biomedical Optics, 15(4):047011-1-7 (2010).
CM Lee et al., "Scanning Fiber Endoscopy With Highly Flexible, 1 MM Catheterscopes for Wide-Field, Full-Color Imaging," Journal of Biophotonics. 3(5-6):385-407 (2010).

(56) References Cited

OTHER PUBLICATIONS

CM Lee et al., "Wide Field Fluorescence Imaging in Narrow Passageways Using Scanning Fiber Endoscope Technology," Endoscopic Microscopy V, Proceedings of SPIE, 7558:755806-1-10 (2010).

T Louie et al., "Clinical Assessment of Early Tooth Demineralization Using Polarization Sensitive Optical Coherence Tomography," Lasers in Surgery and Medicine, 42(10):738-745 (2010).

M Staninec et al., "In Vivo Near-IR Imaging of Approximal Dental Decay at 1,310 NM," Lasers in Surgery and Medicine, 42(4):292-298 (2010).

MAB Blank et al., "Laser Scanning Dental Probe for Endodontic Root Canal Treatment," Lasers in Dentistry XVII, Proceedings of SPIE 2011, 7884:788403-1-7 (2011).

CK Hope et al., "Photobleaching of Red Fluorescence in Oral Biofilms," Journal of Periodontal Research, 46(2):228-234 (2011).

National Institute of Dental and Craniofacial Research., "Dental Caries (Tooth Decay) in Children (Age 2 to 11)," NIDCR (2011).

EJ Seibel et al., "Multimodal Flexible Cystoscopy for Creating Co-Registered Panoramas of the Bladder Urothelium," Photonic Therapeutics and Diagnostics VIII, Proceedings of SPIE, 8207:82071A-1-7 (2012).

FTD Soper et al., "Surface Mosaics of the Bladder Reconstructed From Endoscopic Video for Automated Surveillance," IEEE Transactions on Biomedical Engineering, 59(6):1670-1680 (2012).

L Zhang et al., "Spectrally Enhanced Image Resolution of Tooth Enamel Surfaces," Lasers in Dentistry XVIII, Proceedings of SPIE, 8208:82080E-1-15 (2012).

L Zhang et al., "Optical Measure of Enamel Health," 2012 IEEE Global Humanitarian Technology Conference, pp. 345-349 (2012).

C Yang et al., "Mitigating Fluorescence Spectral Overlap in Wide-Field Endoscopic Imaging," Journal of Biomedical Optics, 18(8):086012-1-13 (2013).

C Yang et al., "Color-Matched and Fluorescence-Labeled Esophagus Phantom and Its Applications," Journal of Biomedical Optics, 18(2):026020-1-11 (2013).

L Zhang et al., "Tri-Modal Detection of Early Childhood Caries Using Laser Light Scanning and Fluorescence Spectroscopy—Clinical Prototype," Journal of Biomedical Optics, 18(11):111412-1-8 (2013).

C Yang et al., "Target-To-Background Enhancement in Multispectral Endoscopy with Background Autofluorescence Mitigation for Quantitative Molecular Imaging," Journal of Biomedical Optics, 19(7):076014-1-16 (2014).

Wikipedia., "Methylene blue," available online at: http://en.wikipedia.org/wiki/Methylene_blue_(2016).

CM Brown et al., "Mechanical Design and Analysis for a Scanning Fiber Endoscope," Proceedings of the 2001 ASME International Mechanical Engineering Congress and Exposition, 51:165-166 (2001).

\* cited by examiner

FIG. 19

MULTISPECTRAL WIDE-FIELD ENDOSCOPIC IMAGING OF FLUORESCENCE

CROSS-REFERENCE

This application claims the benefit of U.S. Provisional Application No. 61/934,479, filed Jan. 31, 2014, which application is incorporated herein by reference.

STATEMENT AS TO FEDERALLY SPONSORED RESEARCH

This invention was made with government support under U54CA163059, awarded by the National Institutes of Health. The government has certain rights in the invention.

BACKGROUND OF THE INVENTION

Prior methods and apparatus for wide field fluorescence imaging can be less than ideal in at least some respects, and the prior methods and apparatus can be less than ideal in one or more of many ways. The sensitivity and specificity for diagnosis of diseases of prior wide field fluorescence imaging apparatus can be less than ideal, for example. Also, quantification of the amounts of fluorescence can be less than ideal. Wide field imaging with a small device such as an endoscope can include imaging tissue structures of objects at varying distances from the object. The varying distance can lead to variability in the intensity of the measured fluorescence. Prior methods and apparatus that may be suited for use with imaging devices such as microscopes, which may be limited to a plane, can be less than ideally suited for use with wide field imaging in which the distance of the object can vary (e.g. within a cylindrical shaped body lumen), and field-of-view is limited in real time. Also, the stability and repeatability of the measurement scans of the prior methods and apparatus can be less than ideal in at least some instances.

Determining the location and registration of prior fluorescence signals can be less than ideal in at least some instances. For example, the fluorescence measurement may be combined with one or more imaging modalities, and the fluorescence measurement itself may not provide sufficient structure to register the fluorescence signal with images from other signals.

Prior methods and apparatus of wide field fluorescence imaging can be less than ideal suited to determine subtle variations of the desired measurement signal. For example, prior methods and apparatus can be less than ideally suited to correct spectral overlap, in which a spectrum from one molecular labeling species overlaps with one or more other molecular labeling species. Also, the prior methods and apparatus can be less than ideally suited to correct background fluorescence, which can at least partially obscure a desired measurement signal in at least some instances.

The prior methods and apparatus of wide field fluorescence imaging can be less than ideally suited to measure changes over time. Measuring changes of a tissue structure over time could potentially allow the detection of subtle changes, which could lead to more accurate diagnosis and treatment. However, the prior methods and apparatus are less than ideally suited to repeatedly locate, identify, and measure changes in tissue over time for a specified location for an individual patient.

In light of the above, improved methods and apparatus for wide field spectral imaging are needed. Ideally, such improved methods and apparatus would provide one or more of the following: decreased effects of interfering background fluorescence, compensation for spectral cross-talk between fluorescent molecular labels, improved quantification of the fluorescence signal of interest, decreased quantitative errors associated with imaging distance and angle, improved co-registration of reflectance and fluorescence signals, or improved repeat measurements separated by sufficient time for tissue to change, and combinations thereof.

SUMMARY OF THE INVENTION

Methods and apparatus as described herein provide improved imaging with co-registered fluorescence and reflectance signals. The reflectance signal co-registered with the fluorescence signal allows the fluorescence signal to be corrected in response to the reflectance signal. In many embodiments, one or more characteristics of an interfering background fluorescence can be used to decrease one or more undesirable effects of the interfering fluorescence signal on a fluorescence signal of interest in order to characterize and/or quantify the fluorescence signal of interest. The interfering fluorescence signal may be related to the reflectance signal, such that the reflectance signal can be used to decrease interference from the interfering fluorescence signal from the fluorescence signal of interest. The interfering fluorescence signal may comprise a fluorescence emission spectrum overlapping with the signal of interest. Correcting for the interfering fluorescence signal with the reflectance signal can provide an improved signal to background ratio and improved quantification of the fluorescence signal of interest.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 19 shows CIE color calculations of: A. previously reported BE color, B. simulated healthy esophagus mucosa color, C. simulated BE color, D. Atlantic salmon fillet color in accordance with embodiments.

DETAILED DESCRIPTION OF THE INVENTION

Figure 1A:
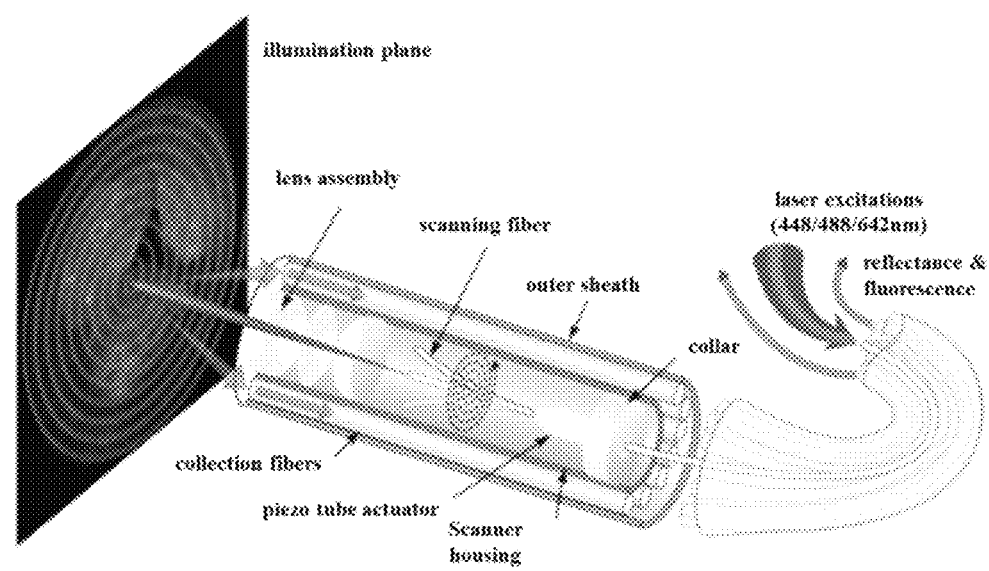
FIG. 1A shows a schematic illustration of the scanning fiber lens assembly and concentric light collection fibers in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

As used herein A and/or B encompasses one or more of A or B, and combinations thereof such as A and B.

Concurrent reflectance and fluorescence imaging as described herein encompasses detecting the collected light from the scanned illumination beam at substantially the same time with a plurality of photodetectors in parallel. Since a typical fluorescence photon is emitted within about 10 nanoseconds from the excitation of the illumination, the detection of light within 30 nanoseconds for a single pixel in the image can insure that the fluorescence and reflectance images are co-registered with no significant time or spatial differences between signals.

The embodiments disclosed herein can be combined in one or more of many ways to provide improved detection and registration of one or more fluorescent or related phosphorescent signals.

Although embodiments herein are described in the context of image acquisition and imaging systems, this is not intended to be limiting, and it shall be understood that the disclosed embodiments can be used for any suitable application.

As used herein like characters identify like elements.

Methods and apparatus for combined imaging with co-registered fluorescence and reflectance signals are described herein. In methods and apparatus described herein, characteristics of interfering background fluorescence can be used to decrease one or more undesirable effects of the interfering fluorescence signal on a fluorescence signal of interest in order to characterize and/or quantify the fluorescence signal of interest. The methods and apparatus described herein can provide an imager, such as a wide field spectral imager, is calibrated with stable and well-characterized fluorescence standards. In order to make measurements over time, image drift is minimized or eliminated by characterization of the stability of the imager.

In methods and apparatus described herein, an imager can be tested using a phantom that mimics human tissue. The methods and apparatus described herein can provide phantoms that mimic the complexities of the fluorescence of a live animal. In methods and apparatus described herein, the animal/organ e.g. esophagus can be open. In methods and apparatus described herein, the animal/organ can be closed. In methods and apparatus described herein, the animal/organ can alternate between open and closed states. In methods and apparatus described herein, the model can include the presence of molecules that are present in an organism's body, e.g. in the human body. The methods and apparatus described herein can involve imaging three dimensional (3D) tissues, including 3D rendering of 3D tissues and two dimensional (2D) rendering of 3D tissues.

In methods and apparatus described herein, dual modes of fluorescence and reflectance can be imaged and processed so as to be in co-registration with one another. Co-registration of reflectance and fluorescence images provides many benefits, including the ability to perform accurate distance compensation for the quantification of fluorescence images. Co-registered reflectance images are used to perform distance compensation on fluorescence images, which eliminates the largest error in quantitative fluorescence measurement. Reflectance images provide depth (3D) information, which is used to correct for possible disparities in fluorescence signals due to differences in depth. The methods and apparatus for distance compensation provided herein are highly advantageous in many applications, including clinical applications, as they are performed in real time during image acquisition and are compatible with wide field imaging. In methods and apparatus described herein, 3D imaging and rendering of 3D anatomical structures, such as tubular structures (e.g. esophagus) can be performed.

In methods and apparatus described herein, the imager can be an endoscope that has a very long depth of focus. Distance compensation is highly important in many applications, such as clinical applications (e.g. mapping of tumor tissue). In contrast to conventional microscopes, for imagers having a long depth of focus (e.g. endoscopes), distance is not automatically corrected for by simply changing the plane of focus. The methods and apparatus for distance compensation described herein provide accurate calibration standards and testing to correct for distance, and are superior to distance compensation methods that rely on modeling rather than precise measurements from a tissue or phantom.

In methods and apparatus described herein, the source of light excitation can include one or more lasers with peak excitation wavelengths ranging from ultraviolet to visible light to infrared spectra, including but limited to red, blue, and/or green lasers. The imager can be a laser scanning endoscope. In methods and apparatus described herein, one excitation source (e.g. one excitation laser) can be used to generate fluorescence and reflectance signals. Reflectance signals can be used to generate anatomical images that contain anatomical information about the tissue being imaged. Fluorescence signals can be used to generate fluorescence images that contain information about the presence and location of a biochemical within the tissue. In methods and apparatus described herein, the emitted reflectance and fluorescence signals can be effectively separated. In methods and apparatus described herein, the emitted reflectance and fluorescence signals can be effectively co-registered. In methods and apparatus described herein, a phantom can be used to model and predict interactions between biological tissues and the imager and light generated by the imager, such as how a light collection portion of the imager receives light in an organ (e.g. a tubular organ, including but not limited to esophagus).

Methods and apparatus for removing interfering background fluorescence, such as autofluorescence and spectral cross-talk due to overlapping emission spectra, are described herein. The methods and apparatus described provide improved signal-to-background ratio. Many fluorescent species emit light in a broad band or spectrum. The methods and apparatus described herein can include characterizing the fluorescence spectra of potentially interfering fluorescent species. The methods and apparatus provided herein can include computing a background fluorescence in a spectrum of interest based on a measured fluorescence in another spectrum, and based on a characterization of the relative amounts of fluorescence emitted at the two spectrums by a given fluorescent species (e.g. collagen) or by a tissue. The methods and apparatus provide for quantitative imaging of one or more fluorescence signals of interest with increased signal over background. The quantification of a fluorescence signal of interest can be a relative quantification or an absolute quantification (e.g. intensity [Watts/mm$^2$]).

Quantification of a fluorescence signal is important in many applications, such as tumor diagnosis, in which autofluorescence and/or aberrations in a fluorescence signal due to distance of a tissue from a light collection portion can lead to an incorrect diagnosis. For example, in cases where reduced intensity of a fluorescence signal of interest indicates disease, a healthy portion of a tissue having a lower concentration of an autofluorescent species, such as collagen, may be misdiagnosed as a tumor. Methods and apparatus are described herein that can circumvent misdiagnoses by accurately correcting fluorescence signals of interest.

Methods and apparatus for enhancing target-to-background ratios of fluorescence signals in an image, such as by signal averaging, are described herein. In methods and apparatus described herein, image processing from a series of video images can be used to increase signal-to-noise by enhancing the target-to-background ratios of fluorescence signals, in particular weak fluorescence signals, in an image. In methods and apparatus described herein, a moving imager (e.g. an endoscope disposed in a tissue) acquires images at a defined rate (e.g. 30 frames per second (FPS)). In methods and apparatus described herein, signal averaging can be performed to average signal intensity at a fixed location and multiple frames are averaged while a light collection portion of an imager remains motionless. In methods and apparatus described herein, signal averaging can be performed on multiple (e.g. sequential) frames that are collected while a light collection portion of an imager moves. In methods and apparatus described herein, the rate of movement of the light collector can be slow relative to the rate of image acquisition, and image stitching can be used to stitch sequentially acquired images together. In methods and apparatus described herein, hundreds of frames can be captured in a period of seconds and sequentially captured images can be stitched together, providing signal averaging of hundreds of frames. A concurrently captured, co-registered sequence of images can also be stitched together, such as, e.g., a sequence of reflectance images.

Methods and apparatus for concurrent imaging of multiple signals in an image are described herein. Other imaging modalities may rely on sequential imaging of multiple signals. In cases where scanning of a light source is required to form an image, the time difference between imaging of a first signal versus a second signal can be on the order of milliseconds or more. This time delay can result in less than ideal co-registration of images of a first signal with a second signal, particularly in cases where the light collector is moving (e.g. a camera moving through a tissue), for example. The methods and apparatus described herein can allow imaging of multiple signals from each pixel location with temporal resolution on the order of tens of nanoseconds (e.g. 10, 20, or 30 nanoseconds), for example. This improvement in temporal resolution (e.g. time differences five, six or more orders of magnitude smaller) can result in greatly improved co-registration between signals, including fluorescence and/or reflectance signals.

The methods and apparatus described herein can allow for imaging and characterizing and/or quantifying multiple molecular probes with fluorescence labels to determine the degree of co-localization of these probes. In methods and apparatus described herein, optical properties of the fluorescence and reflectance signals, such as intensity and/or spectral properties, can be analyzed to characterize and quantify the multiple fluorescent species in images of a tissue or a phantom.

The methods and apparatus provided herein can allow for measuring and mapping one or more fluorescence signals of interest to determine where a molecular species is located. In methods and apparatus described herein, measuring and mapping one or more fluorescence signals of interest can be performed and used for clinical procedures such as surgical procedures. In methods and apparatus described herein, measuring and mapping data can be matched to other imaging modalities, including but not limited to X-ray, MRI, ultrasound, optical coherence tomography and/or photoacoustic modalities. In methods and apparatus described herein, fluorescence signals of interest can be mapped on surfaces of one or more organs, including but not limited to esophagus, colon, intestine, heart and stomach. In methods and apparatus described herein, the depth of a molecular species in a tissue can be mapped. In methods and apparatus described herein, depth information of a molecular species of interest can be used to help stage and align with other imaging modalities, such as ultrasound. The methods and apparatus provided herein can allow for measuring and mapping one or more fluorescence signals of interest with sub-cellular spatial resolution.

The methods and apparatus provided herein can allow for measuring and mapping one or more fluorescence signals of interest over time to determine how the spatial distribution of a molecular species is changing over time. The methods and apparatus provided herein can allow the progression of a disease state to be monitored and diagnosed from a healthy or benign state by imaging one or more fluorescence signals of interest over time ("trending"). For example, by measuring the intensity and location of the natural porphyrin signal from the presence of bacteria in the mouth that is separated from the autofluorescence of the teeth and gums at each dental visit or with a home monitoring system over time, there can be prediction of dental disease and improved specificity and sensitivity of disease diagnosis, especially by computer-aided diagnostic algorithms. In methods and apparatus described herein, a tissue can be imaged at multiple time points, such as at a first time point and then at a second time point that occurs, e.g. one month, two months, three months, four months, five months, six months or 12 months after the first time point. In methods and apparatus described herein, changes in one or more fluorescence signals of interest over time can be used to indicate one or more changes in a disease state, such as progression of an infection or growth of a tumor.

Scanning Fiber Endoscope with Multiple Fluorescence-Reflectance Imaging Channels for Guiding Biopsy We report on the performance and detection sensitivity of a newly developed wide-field, multi-spectral fluorescence-reflectance scanning fiber endoscope (SFE), which was designed for imaging of fluorescence labeled molecular probes during endoscopy for early cancer detection. The device contains three fluorescence excitation sources: 448 nm (blue), 488 nm (blue/green) and 642 nm (red). Three fluorescence detection channels for quantitative diagnostic imaging and one reflectance channel for intraoperative navigation are available. Using test targets, concurrent (30 Hz), wide-field)(80° and high resolution (50 µm) imaging was confirmed. The detection sensitivity was evaluated at nanomolar level (5 nmol/L) dye concentrations. Meanwhile, simultaneous detection of blue, green, and red/NIR fluorescence with a gray-scale reflectance background was demonstrated for concurrent multispectral fluorescence endoscopic imaging.

Many early cancerous conditions are treatable but are invisible to conventional white-light endoscopy. The challenge for the next generation of endoscope technology is to provide image contrast for pre-cancerous lesions before they become invasive.

High detection sensitivity at the cellular or sub-cellular level is critical for detecting the earliest stages of cancers in tissue surface epithelia during routine endoscopy, and/or removing any residual malignant cells during surgical resection of tumors. Fluorescence molecular imaging provides specificity along with high contrast of disease lesions which are invisible under conventional white-light endoscopy. In addition, molecularly-specific targeted probes can provide red-flagging of only diseased cells during wide-field fluorescence endoscopic examination.

Furthermore, as many tumors express multiple cell surface markers and these molecular signatures are heterogeneous across patients and within the tumor. Therefore, simultaneous imaging of numerous different molecular targets is important for increasing the sensitivity and specificity of cancer diagnosis.

For molecular imaging of pre-cancerous tissue, a wide-field, high resolution and video rate multi-spectral fluorescence-reflectance scanning fiber endoscope (SFE) was developed. The ultrathin and flexible multispectral SFE scans an illumination optical fiber at 11 kHz in a spiral pattern, and excites fluorescence at 448 nm (blue), 488 nm (blue/green), and 642 nm (red) using individual lasers at low power (<3 mW). Light collection fibers surrounding the illumination fiber transmit the tissue fluorescence and reflectance to a set of wavelength separation beam splitters, filters and photomultipliers. The electronic signals are processed for real time display of concurrent multispectral fluorescence-reflectance images.

Multispectral SFE System

Figure 1B:
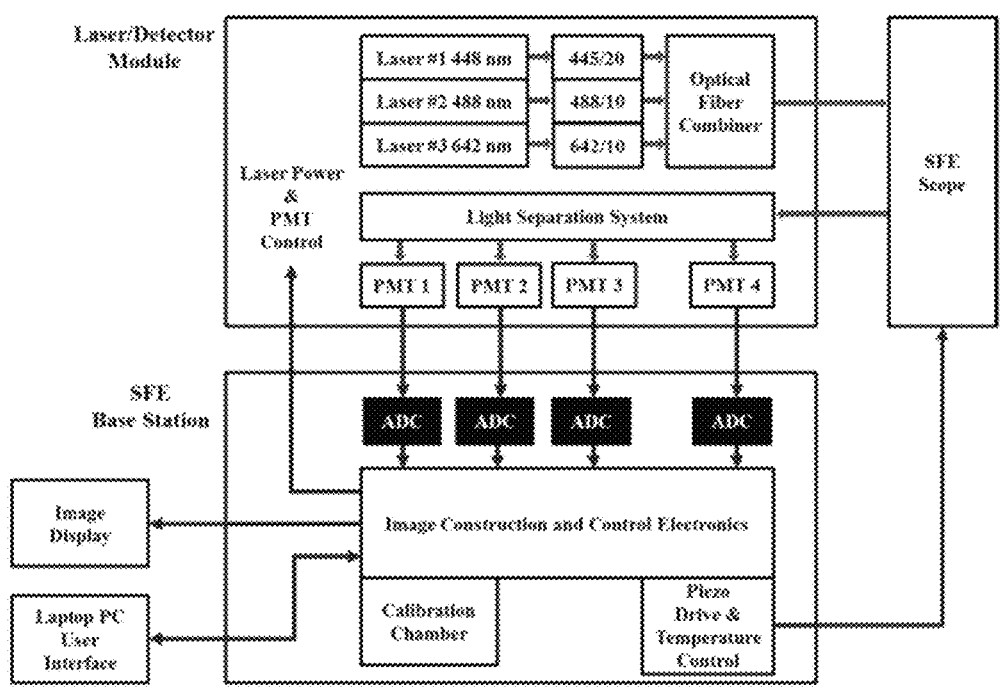
FIG. 1B shows a block diagram of the optical and electrical components of the scanning fiber endoscope system in accordance with embodiments.

The new multispectral SFE system was specifically designed and engineered for wide field, high-resolution and real-time fluorescence molecular imaging and guiding biopsy. Compared to a conventional endoscopic passive imaging system using diffuse light illumination, the multispectral SFE incorporates 3 diode lasers (FiberTec™, Blue Sky Research): 448, 488, and 642 nm that can be jointly or selectively launched at the base station (FiberTec™, Blue Sky Research). The fiber-coupled laser outputs are sent to the distal end of the SFE scope via a single mode optical fiber using a custom optical fiber combiner (Wave Division Multiplexer, or WDM, Oz Optics). The combined multi-laser beam is scanned in a spiral pattern within the tip of this single illumination fiber by a piezoelectric transducer and focused onto the target surface by a lens assembly. FIG. 1A shows a schematic diagram of the multispectral SFE system, and FIG. 1B shows the design diagram of the system.

Figure 1C:
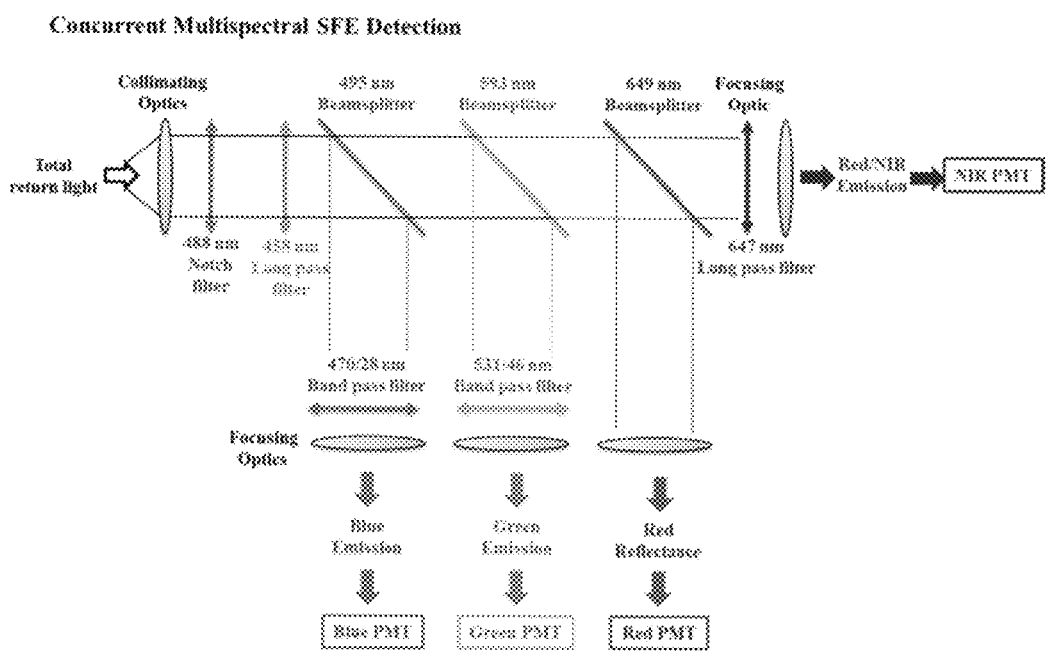
FIG. 1C shows a wavelength separation system of the multispectral SFE in accordance with embodiments.

Fluorescence or diffuse reflected light is then collected by a concentric ring of high numerical aperture optical fibers which surround the single mode beam delivery fiber and lens assembly. The collected light is separated into four wavelength bands (Blue, Green, Red/NIR fluorescence and Red reflectance respectively) by three dichroic beam splitters. Each separate spectral band is then passed through a high optical density band-pass (>10 OD), or long-pass filter positioned in front of a high gain photomultiplier tube (PMT). Custom designed software maps the synchronized detection signals as points in the spiral scan pattern which are then converted to the 2-dimensional pixel position on the RGB digital display—red, green, and blue for fluorescence images and grayscale for reflectance. FIG. 1C shows the detailed wavelength separation optical system used in the multispectral SFE.

Multispectral Fluorescence-Reflectance Imaging with Optical Standards

Quantitative dye-in-polymer fluorescent targets were fabricated as calibration standards for evaluation of the multispectral fluorescence imaging system. Photostable dyes Fluorol 555 (FL), Pyrromethene 567 (PM) and Oxazine 725 (OX) (Exciton, Dayton, Ohio) were selected to represent in vivo fluorophores such as Coumarin (DEAC), Fluorescein, and Cyanine (Cy5), respectively. And the targets were made by following an established dye-in-polymer protocol.

The dye-in-polymer calibration standards (6 mm thick) were cast into 1.5-cm diameter off-the-shelf black phenolic screw-caps (16198-911 VWR, Visalia, Calif.). The targets covered a range of concentrations from 1-100 micromolar. Standards without dye were also prepared as negative controls to confirm that clear polymer targets exhibit no autofluorescence.

Figure 2A:
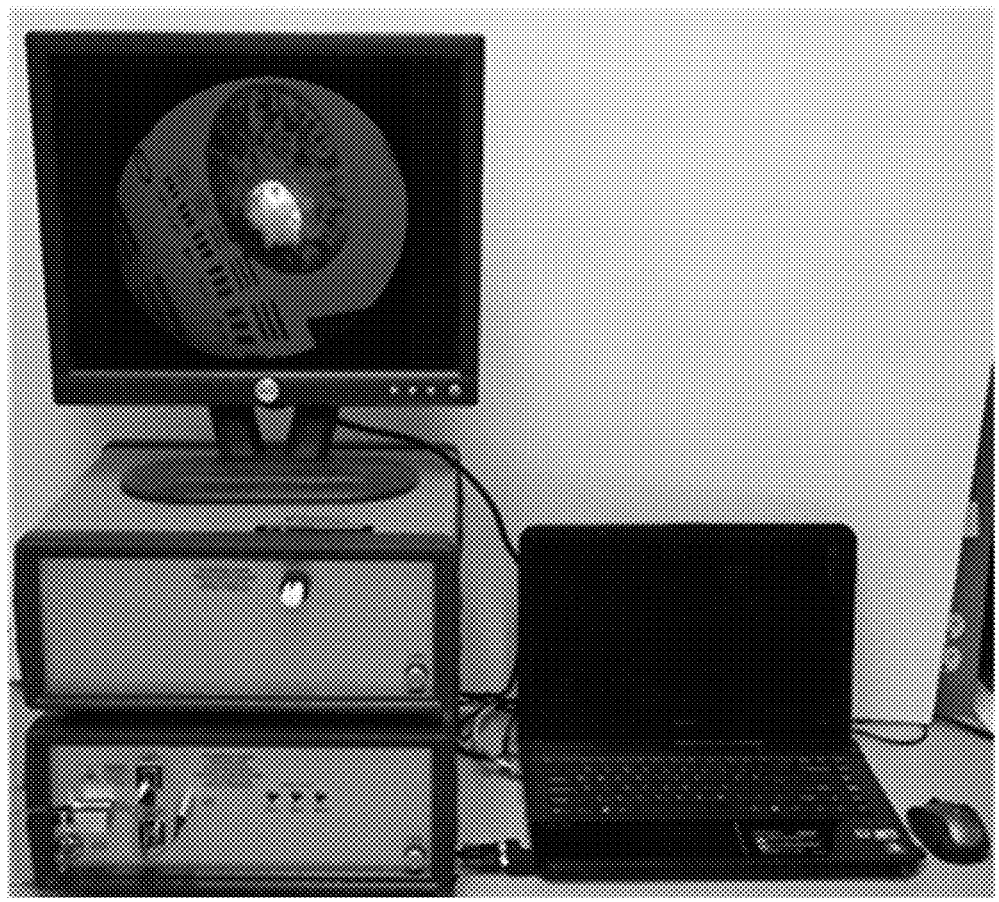
FIG. 2A shows a real-time, high-sensitivity and concurrent multispectral fluorescence Scanning Fiber Endoscope (SFE) system with a 2.1-mm endoscope in accordance with embodiments.

Furthermore, imaging resolution of the multispectral SFE was evaluated using a 1951 USAF resolution test chart, as shown in FIG. 2A.

SFE Fluorescence Sensitivity Measurement

Sensitivity of the SFE was defined as the minimum amount of fluorescence measurable by the system, more specifically, the lowest concentration of fluorescent dye molecules that can be detected/imaged with a signal-to-noise ratio (SNR) greater than 2. For high sensitivity fluorescence detection, a new 2.1-mm outer diameter (OD) scope was designed and fabricated for the multispectral SFE system. The light collection portion of the scope consists of a concentric ring of 6 identical, 500 micron diameter multimode optical plastic fibers (Mitsubishi Rayon Co., LTD, Tokyo, Japan). Since the collection numerical aperture remained high (NA=0.6), it is estimated that the 2.1-mm scope has 20× increase in collection efficiency due to the larger (20×) collection area of the fibers compared to the 1.2-mm diameter SFE scope.

Fluorescent dyes for ex vivo application, fluorescein and Cy5.5 were chosen for the sensitivity measurement. Dilutions of fluorescein (Sodium Fluorescein, Sigma-Aldrich, St. Louis, Mo., USA) and Cy5.5 NHS ester (Lumiprobe, Fla., USA) were prepared in double distilled water (ddH2O) solution. For making the dilutions of Cy5.5 NHS ester, the dye was first dissolved in DMSO as recommended by the manufacturer, and then serial dilutions were made using double-distilled water (ddH2O). Dilutions covered the range from micromolar (µmol/L) to nanomolar (nmol/L) for both dyes. All dilutions were kept at a neutral pH point (pH=7).

During a measurement, the SFE 488 nm laser was turned on for detection of fluorescein in the Green channel, whereas the SFE 642 nm laser was turned on for the detection of Cy5.5 in the Red/NIR channel. To guarantee reproducibility, all measurements were performed by imaging a 50 µl dye droplet dispensed on a diffuse, non-fluorescent and flat Teflon surface, with the SFE 2.1-mm scope pointing down perpendicularly to the Teflon surface at a 20-mm distance. During the evaluation, the gains and offsets on the PMTs and digital display were held constant. Imaging performance at video-rates (30 Hz) was then evaluated.

High optical density (OD) filters (Semrock, Inc, Rochester, N.Y.) were placed in front of the fluorescence detection PMTs to block light from the excitation laser sources. To verify that the background light from the excitation lasers was more that 10× below the measured fluorescence signals, images were recorded without any dyes placed on the Teflon surface.

Multispectral Scanning Fiber Endoscope (SFE) System

The new multispectral SFE (shown in FIG. 2A-C) was fabricated for the purpose of fluorescence molecular endoscopy. The multispectral SFE system includes a monitor showing live multispectral fluorescence imaging with a gray scale reflectance background, a base station, and a computer with control user interface (FIG. 2A). Under standard operating conditions, the SFE captures and displays images at 30 Hz, with an 80-degree field-of-view, and 50 micron image resolution. The image resolution was measured using the USAF 1951 test chart (on monitor in FIG. 2A): at the group #3 and element #3 of the chart, the difference between the black and white images of the grating can still be clearly determined.

Figure 2B:
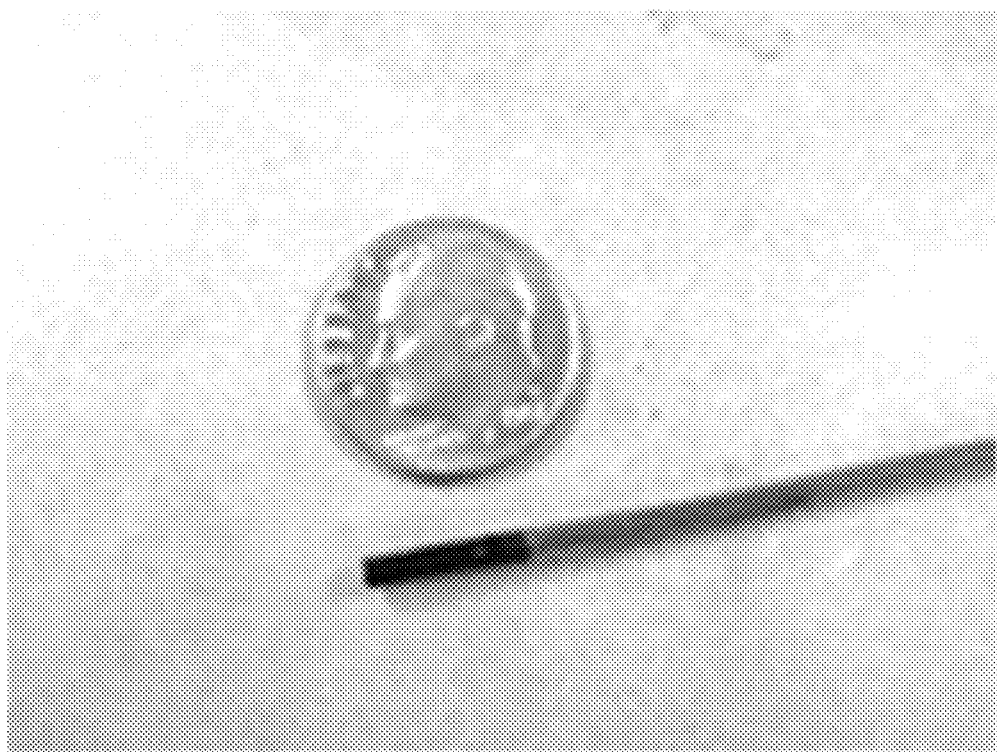
FIG. 2B shows a photo of the 2.1-mm ultrathin and flexible endoscope with 9-mm rigid tip length in accordance with embodiments.

Meanwhile, the 2.1-mm SFE scope uses 6 highly flexible, loosely enclosed optical fibers within the shaft, thereby maintaining low flexural rigidity, and a minimum bend radius of 7 mm. A photo of the 2.1-mm ultrathin and flexible endoscope with 9-mm rigid tip length is shown in FIG. 2B. The high flexibility and small size allows the scope to reach small body ducts, vessels and cavities, where most rigid endoscopes cannot easily reach. In clinical applications, the flexible scope can be incorporated with guide wires, rigid insertion tubes, or working channels to be delivered/pushed into the inspection location. Previous clinical work has shown that smaller diameter SFE scopes using 250 μm plastic optical return fibers can withstand the high-level disinfection and cleaning required for commercial flexible endoscopes during routine clinical testing in a hospital environment.

Figure 2C:
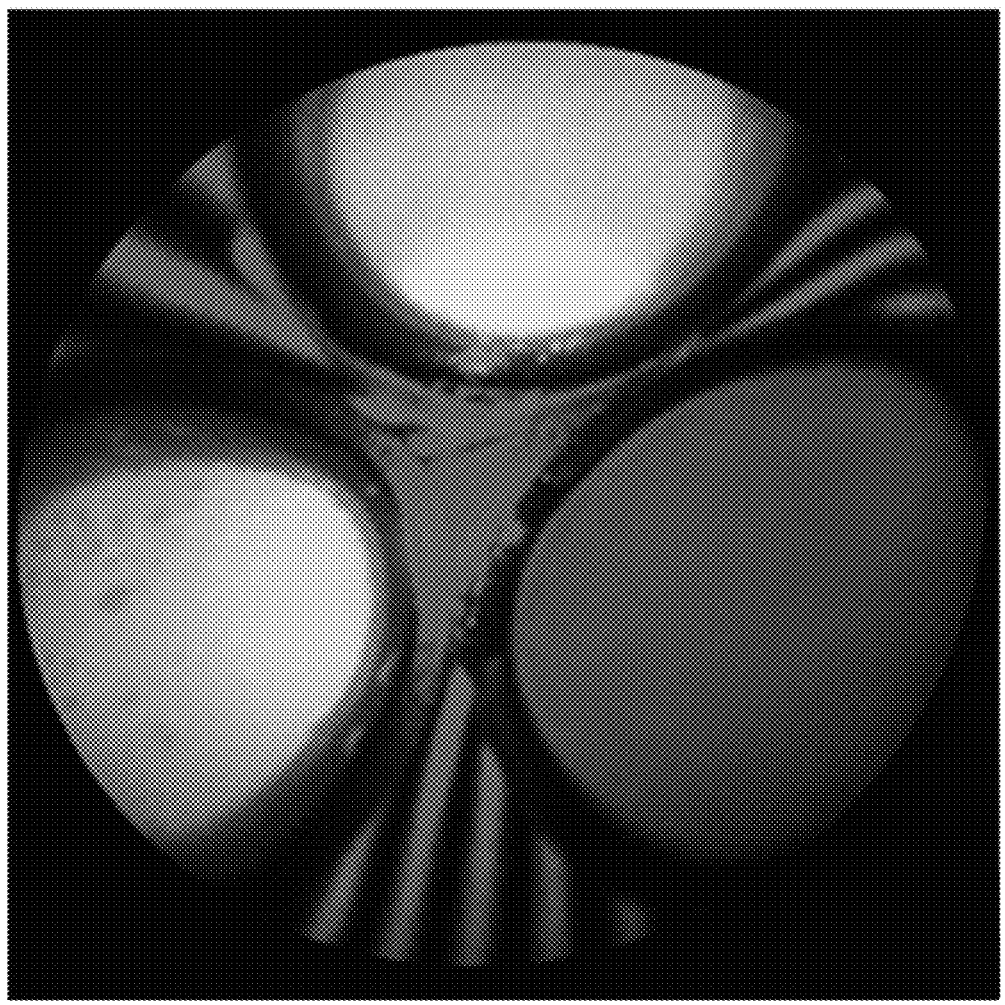
FIG. 2C shows a multispectral fluorescence SFE imaging of the calibration dye-in-polymer targets with a gray scale reflectance background in accordance with embodiments.

Three fluorescence channels and one reflectance channel are simultaneously processed at 12-bits per pixel to create spatially co-registered blue, green, red fluorescence and a grayscale reflectance background images. Concurrent, widefiled and high-resolution imaging was demonstrated on all channels for the multispectral SFE, with intraoperative navigation feature from the gray-scale reflectance background. Multispectral fluorescence SFE imaging of the calibration dye-in-polymer targets with a gray scale reflectance background is shown in FIG. 2C. Meanwhile, the SFE has the ability to perform image guided biopsies using a Distance Compensation algorithm.

Exemplary methods and apparatus related to this section are provided below in Example 1.

Multi-Spectral Scanning Fiber Endoscope with Concurrent Autofluorescence Mitigation for Enhanced Target-to-Background Ratio Imaging We developed a multispectral fluorescence-reflectance scanning fiber endoscope (SFE) for wide-field molecular imaging of fluorescence-labeled molecular probes. Concurrent multi-channels imaging with the wide-field SFE also allows for real-time mitigation of background autofluorescence (AF) signal, especially when the FDA approved fluorescein is used as the target fluorophore. In the current study, we demonstrated a real-time AF mitigation algorithm on a tissue phantom which featured molecular probe targeted cells of high grade dysplasia on a substrate containing AF species. The target-to-background ratio was enhanced by over an order of magnitude when applying the real-time AF mitigation algorithm. By minimizing the background signal, multispectral fluorescence imaging can provide sufficient image contrast and quantitative target information for detecting small pre-cancerous lesions in vivo.

Numerous fluorescent molecular probes targeting disease specific biomarkers are under development for clinical applications. In particular, detection of early cancerous lesions using molecular imaging can improve disease diagnosis and increase survival rate. Numerous studies have demonstrated the application of fluorescence molecular endoscopic imaging. Applications include the detection of high grade dysplasia (HGD) and esophageal adenocarcinoma (EAC) in Barrett's esophagus, detection of early neoplasia in oral tissue, bladder, lung, or small GI ducts, as well as navigation and demarcation of tumor margins during brain surgery.

Compared with other optical contrast enhancements methods, such as narrow-band imaging (NBI™) and autofluorescence imaging (AFI), fluorescence imaging with exogenous probes can target disease specific molecular signatures. Overexpressed proteins at the cell surface present excellent targets for disease identification. Numerous targets have been studied and include epidermal growth factor receptor (EGFR), ERBB2, Cyclophilin A (CYPA). Therefore, fluorescence-based molecular imaging can be more sensitive and specific for the detection of early stage pre-cancerous changes in the epithelium mucosa proteomics before deeper level tissue penetration.

However, as many pre-cancerous lesions are small and patchy, providing sufficient image contrast and quantitative information on fluorophore probe location can be challenging, especially in narrow lumens and ducts.

For in vivo endoscopic molecular imaging, the background tissue autofluorescence (AF) is often a limiting factor for achieving high image contrast, which is often referred to as the target-to-background ratio (T/B). Sometimes, the tissue AF signal can even mask the target fluorescence signal if the early-cancer lesion is composed of only a few cells, thus making the molecular endoscopic diagnosis impossible.

To address this limitation a wide-field multi-spectral scanning fiber endoscope (SFE) was developed, with the capability to increase the T/B of fluorescent images by mitigating background AF. The SFE employs multiple concurrent channels which allows for wide-field fluorescence imaging with real-time image subtraction of AF, especially when the FDA approved fluorescein dye is used as the target probe fluorophore.

In the present study, we report on the in vitro validation of the real-time AF mitigation technique. The imaging device—wide-field multispectral SFE, was combined with a plug-in-and-play multi-laser fiber-optic source—Coherent® OBIS Galaxy™ with OBIS™ FP lasers (Coherent, Santa Clara, Calif.) for imaging of a newly developed tissue phantom. The realistic phantom features a mucosal layer that exhibits high-grade dysplasia (HGD) and esophageal adenocarcinoma (EAC) cells, and a sub-mucosal AF background. Fluorescent probes were then applied to the phantom for molecular targeting of cancer associated biomarker proteins. The target to background ratio was raised by an order of magnitude for a fluorescein fluorophore. Moreover, rationale for the AF mitigation algorithm was further supported by ex vivo quantitative fluorescence imaging using an IVIS Spectrum Imaging device (Perkin Elmer, Norwalk, Conn.).

Realistic Tissue Phantom

Bovine collagen (Sigma Aldrich, St. Louis, Mo.) was digested using collagenase (Invitrogen/Life Technologies, Carlsbad, Calif.) and reconstituted into a solid gel to serve as the AF background. Rat tail collagen gels (Invitrogen/Life Technologies, Carlsbad, Calif.) were seeded with CP-D (American Type Culture Collection, Manassas, Va.), a HGD Barrett's Esophagus cell line. Cultures were fixed in methanol. Overexpression of EGFR, ERBB2, and CYPA were identified through concurrent direct and indirect immunofluorescence staining. Direct staining was accomplished using anti-CYPA conjugated to FITC (Bioss, Woburn, Mass.). Indirect staining was performed using goat Alexa fluor 488 (Invitrogen/Life Technologies, Carlsbad, Calif.) conjugated antibodies to target anti-ERBB2 and anti-EGFR. The seeded gels were laid upon the solid collagen background for imaging. Detailed protocols regarding the tissue phantom are provided in.

Imaging Instrumentation

The multispectral SFE system has wide field (80 degree), high-resolution (50 microns) and real-time (30 Hz) fluorescence-reflectance endoscopic imaging capabilities. Compared to a conventional endoscopic imaging system using passive diffuse light illumination, the SFE incorporates laser-based illumination/fluorescence excitation that can be jointly or selectively launched at the base station and sent to the distal end of the SFE scope via a single mode optical fiber. In the present study, a multi-laser fiber-optic source—the Coherent® OBIS Galaxy™ with OBIS™ FP lasers at 445 nm, 488 nm and 640 nm were used (Coherent, Santa Clara, Calif.). The combined multi-laser beam is scanned in a spiral pattern by a piezoelectric transducer and focused onto the target surface by a lens assembly.

Fluorescence and reflectance are then collected by a concentric ring of high numerical aperture optical fibers which surround the single mode beam delivery fiber and lens assembly. To increase the sensitivity for fluorescence detection, a 2.1-mm outer diameter (OD) scope was designed and fabricated. Compared to the previous 1.2-mm SFE scope, this new design employs a concentric ring of 6 identical, 500-micron diameter high numerical aperture light collection fibers, which yields a 20× gain in returning light collection. Therefore, the new 2.1-mm SFE scope provides a significant increase in light detection sensitivity, and without significantly increasing size or flexural rigidity.

The collected light is separated into four wavelength bands (Blue, Green, and Red fluorescence and Red reflectance respectively) by three dichroic beam splitters. Each band is then passed through a high optical density band-pass (>10 OD), or long-pass filter positioned in front of a high gain photomultiplier tube (PMT). Custom designed software maps the synchronized detection signals as points in the spiral scan pattern of the single mode fiber which are then converted to the 2-dimensional pixel position on the RGB digital display. Red, green, and blue color channels for fluorescence images and grayscale for reflectance. The resulting images are in spatial registration since all of the excitation lasers are coincident at the target location simultaneously.

AF Mitigation Algorithm

Figure 3A:
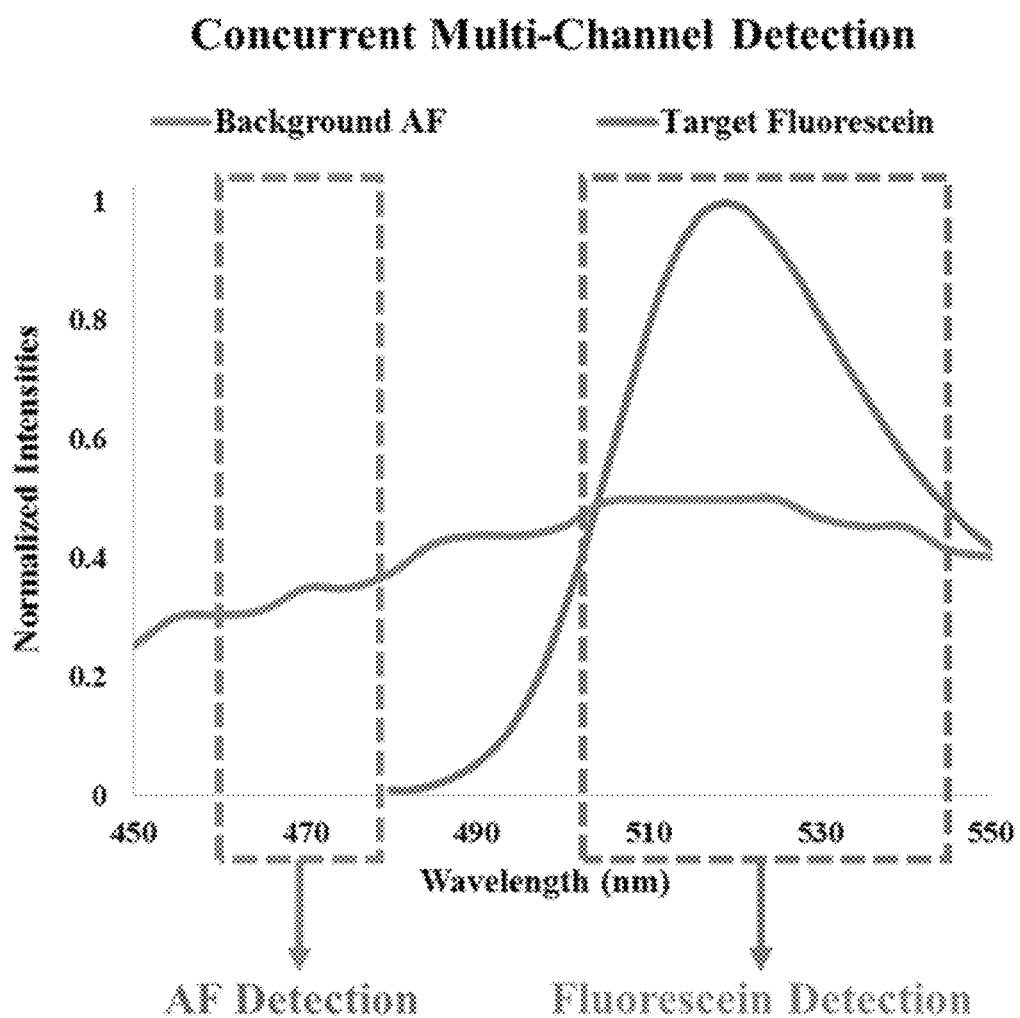
FIG. 3A-3D show a graphical illustration of the real time AF mitigation algorithm on the multispectral SFE system for fluorescein fluorescence imaging in accordance with embodiments.
Figure 3B:
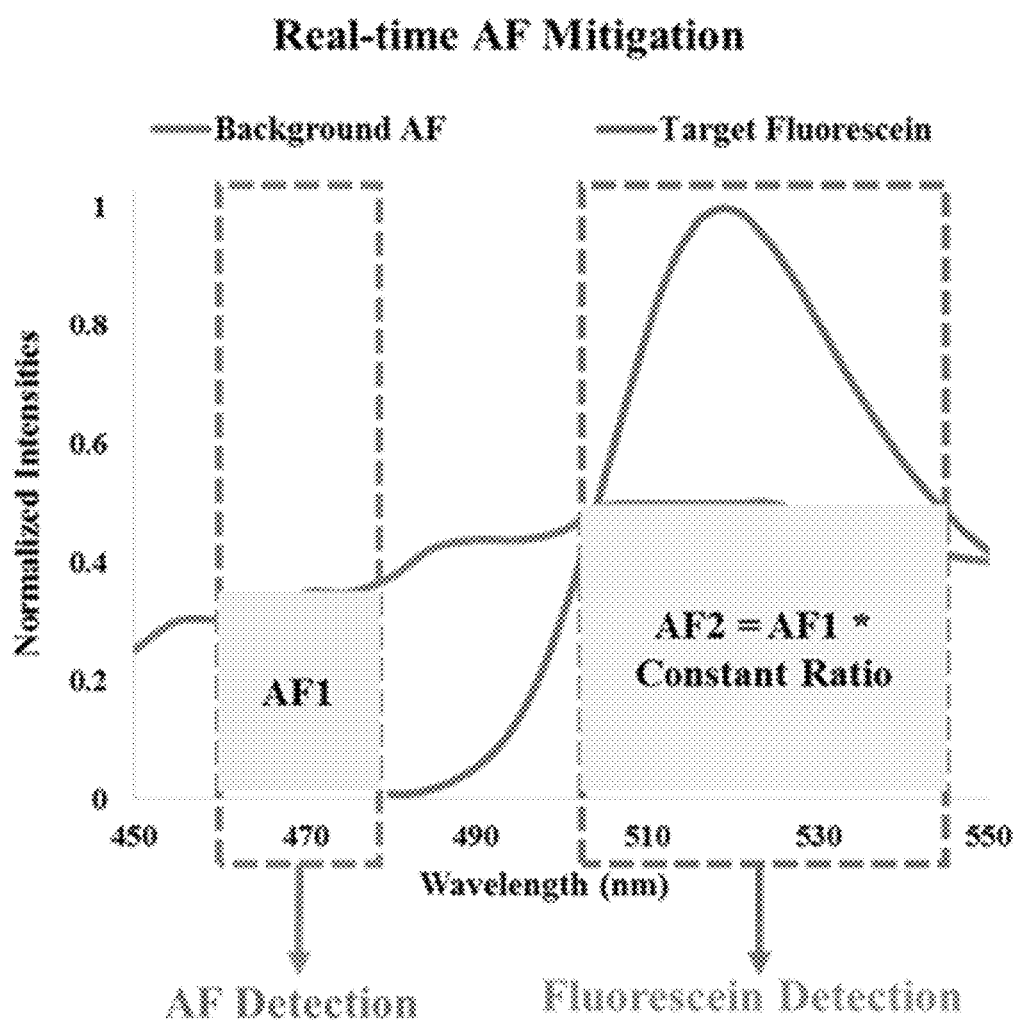
Figure 3C:
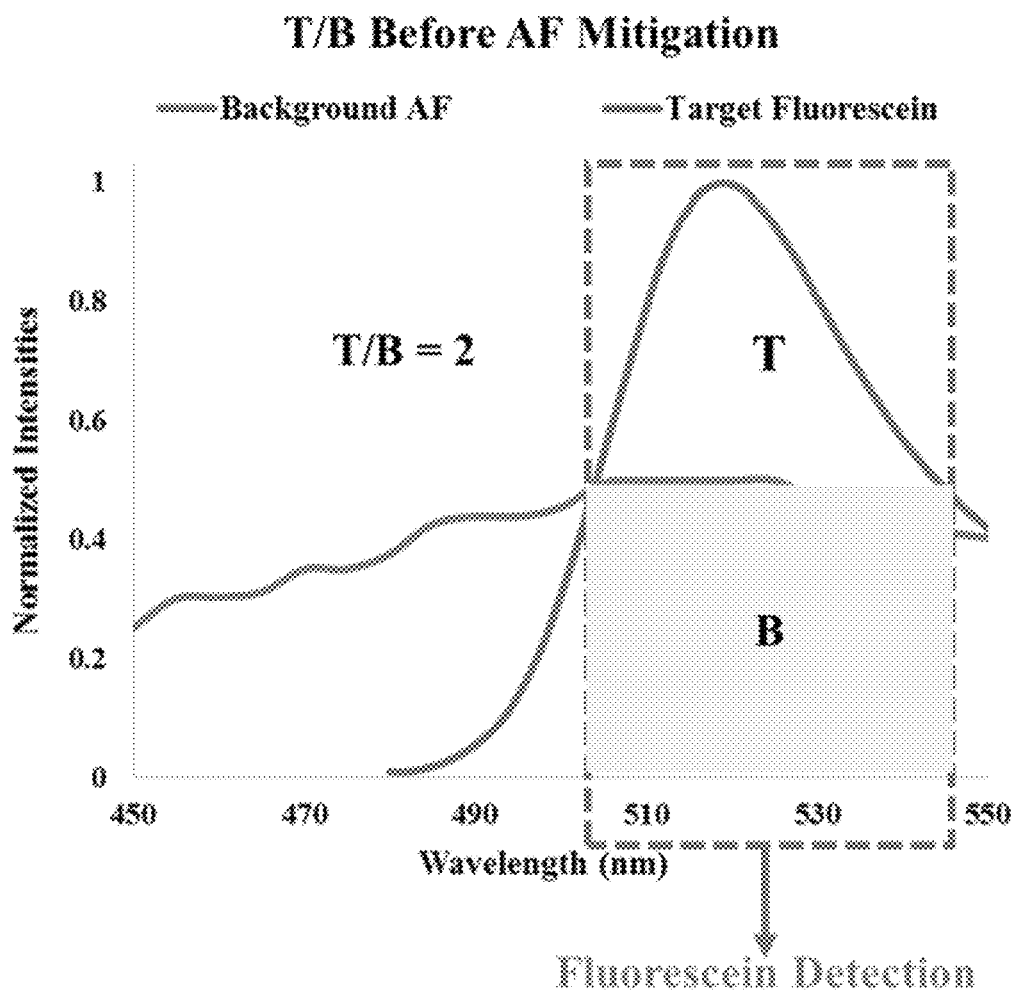
Figure 3D:
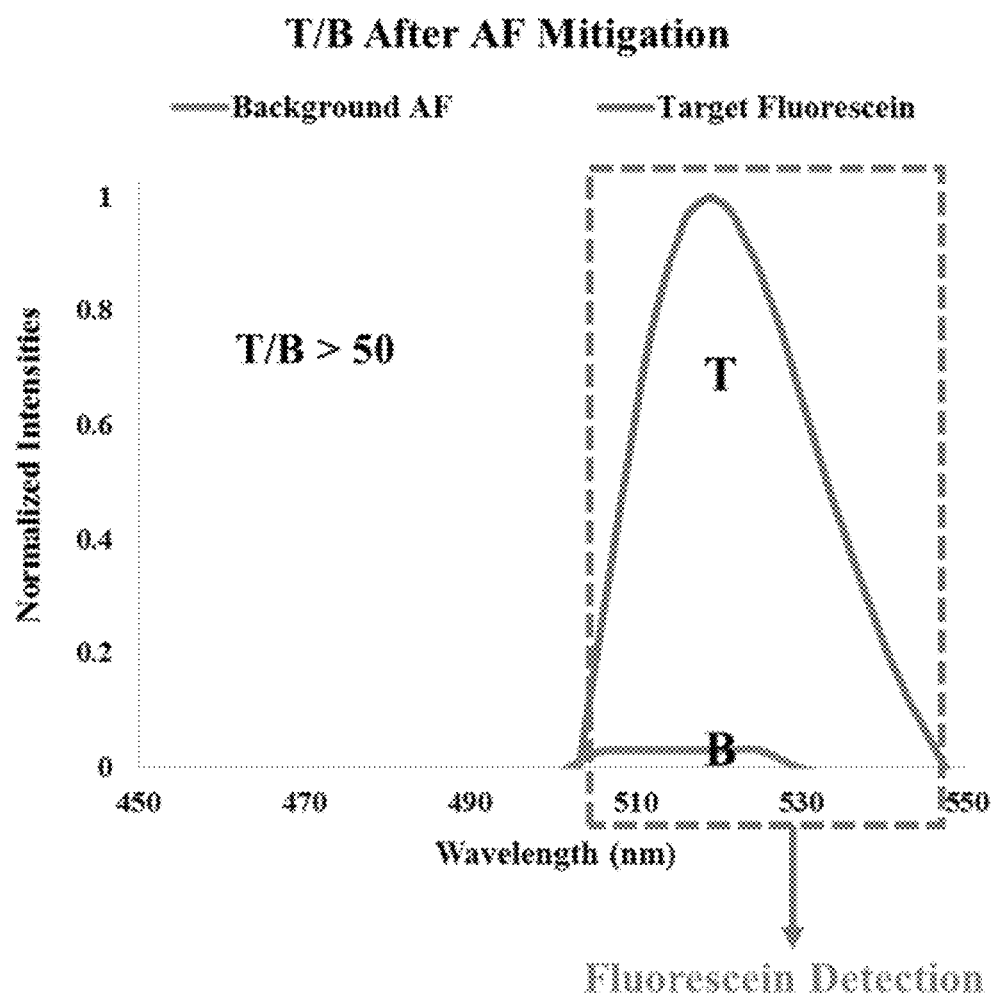

The implementation of the real time AF mitigation algorithm works by simultaneously launching a reference beam (445 nm laser) together with the target beam (488 nm laser). Their respective emission signals are recorded in concurrent but separate detection channels, as the AF and fluorescein detection channels shown FIG. 3A. Mitigation of the background AF signal, as demonstrated in FIG. 3B, is achieved by subtracting from the target signal the reference signal (AF1) multiplied by a pre-calibrated constant ratio, at a pixel by pixel resolution from the (fluorescein+AF2) signal. After the AF subtraction/mitigation, the T/B will be enhanced by a significant amount due to the elimination of the background signal. FIGS. 3A-3D graphically illustrate this AF mitigation algorithm when fluorescein is the target fluorophore.

Exemplary methods and apparatus related to this section are provided below in Example 2.

Color-Matched and Fluorescence-Labeled Esophagus Phantom

Molecular imaging (also known as immunophotodiagnostic imaging) has drawn increasing interest in the field of diagnostic medicine because of its potential to target disease biomarkers for biopsy and diagnostic purposes. For example, in gastrointestinal endoscopy, the combination of fluorescence labeled molecular probes with wide-field multi-modal endoscopic devices can provide visualization of detailed biological information at the cellular or subcellular level, holding promise to enhance diagnosis and characterization of early cancer lesions in the GI tract. In the development of these molecular imaging approaches, it is critical to have realistic, stable and reproducible optical phantoms, to calibrate endoscope systems and evaluate their performance. Moreover, crucial problems in molecular imaging such as biomarker quantification and mapping of probed disease lesions can be explored in vitro using these realistic phantom models.

One application of molecular endoscopic imaging is the detection of high-grade dysplasia and early adenocarcinoma in Barrett's esophagus. The mucosa of Barrett's esophagus has a much greater risk of progression to cancer (30 to 125 times greater than normal esophagus). Therefore, surveillance of patients with Barrett's esophagus is critical for early detection and localization of dysplasia. However, conventional white light endoscopy screening has significant limitations because high-grade dysplasia and early adenocarcinoma lesions usually lie flat on the tissue surface and are endoscopically "invisible" as they do not differ in appearance to the surrounding mucosa. Therefore, there is a need for a targeted molecular imaging strategy for early detection and prevention of cancer in patients with Barrett's esophagus. Furthermore, topical application of targeted fluorescent probes is favored over intravenously administered markers since regulatory limitations are less restrictive for short term exposure to surface contrast agents. Peptide conjugated dyes (e.g. FITC) tend to concentrate in the upper mucosal layers and are activated by shorter wavelength (~480 nm) light sources. A phantom model developed for simulating Barrett's esophagus, including the molecular probed surface dysplasia, would be of value for the purposes of instrument calibration and diagnostic algorithm development.

Phantoms are often constructed to simulate tissue optical and/or morphological properties for the development of imaging techniques. Among these phantom designs, some were employed with multiple materials to construct stable, multi-layer tissue phantoms with essential optical properties, some were fabricated with three-dimensional structures for the purpose of quantitative optical spectroscopy and for the application in photodynamic therapy. Additionally, work has also been done incorporating fluorescent nanoparticles into optical phantoms to act as quantitative molecular imaging standards. However, little has been addressed in the field of optical phantoms for the purpose of simulating fluorescent labeling of targeted surface biomarkers in clinical endoscopy, specifically in the field of quantitative fluorescent molecular video-endoscopy. Therefore there is a need to develop optical phantoms for both research purposes and preclinical instrumentation evaluations, which incorporate the simulation of quantifiable surface molecular biomarkers into a multi-layer three-dimensional tissue phantom.

Figure 4:
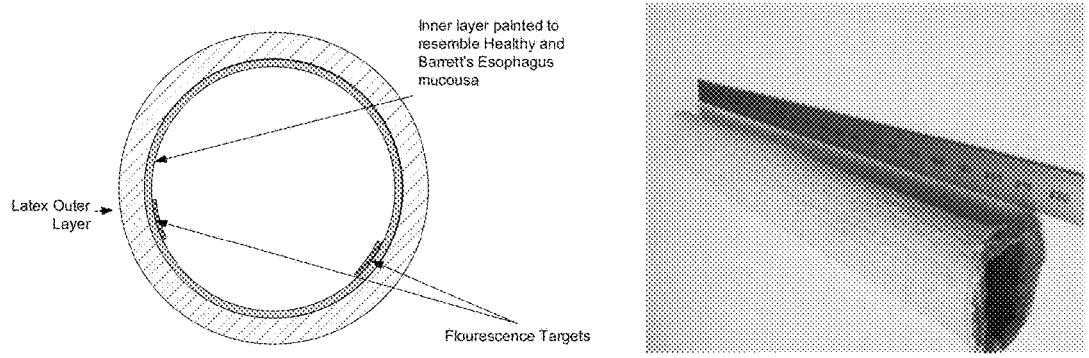
FIG. 4 shows a cross-sectional graph illustrating the phantom design (left) and a photo overview of the resultant phantom (right) in accordance with embodiments.

Recent studies have demonstrated three-dimensional tissue phantoms with a quantitative subsurface fluorescence contrast agent, subsurface tissue autofluorescence, as well as phantoms with quantitative quantum dot-based molecular imaging. In these studies, deep tissue optical penetration was discussed since the biomarker was buried at the subsurface level. Here, we fabricated a synthetic phantom developed to simulate topically labeled fluorescent biomarkers (FIG. 4). Since the biomarker labeling is applied topically to the esophageal tissue, the surface reflectance properties are modeled to accurately mimic the disease condition, whereas synthetic tissue transparency and deep tissue optical penetration were less relevant. This phantom was designed for assisting in the validation of a new multi-spectral fluorescence endoscope for diagnosing high grade dysplasia and neoplasia (in Barrett's esophagus (BE)).

A paintable elastomeric material (latex) was selected and used to fabricate a three-dimensional model that is flexible enough to mimic the essential body movements such as opening and closing of the lower esophageal sphincter while retaining its basic cylindrical shape. Then, a color matching methodology was developed to simulate the visual appearance and diffuse spectral reflectance properties of the tissue. Paint formulations were created to match the visible color properties for a broad spectral range (400 to 700 nm), and a photostable dye was selected which mimics the properties of an FDA approved fluorescent dye (FITC). The dye was diluted to low concentrations in a polyurethane resin and cast into optically thin, rigid forms, to represent low concentrations of biomarker probed disease "hot-spot" locations. The resultant dye-in-polymer phantom is stable, repeatable, economical to fabricate, and has been successfully used to develop image based biomarker labeled quantification techniques.

Phantom Materials

A low-odor, brush-on latex elastomer (RL-451-80, Silpak Inc., Pomona, Calif.) was chosen as the structural base of the phantom. This latex is a water-ammonia mixture and has been widely used in making theatrical masks. Once shaped into a durable, hollow, cylindrical form the flexible tube mimics adult human esophagus morphology while allowing for physiological simulations, such as the opening and closing of the lower esophageal sphincter as well as other body motions.

Healthy and Barrett's esophagus mucosa layers were simulated through combining acrylic liquid-based paint colors (Golden Artist Colors, Inc. New Berlin, N.Y.) and a gel-based matte medium (Golden Artist Colors, Inc. New Berlin, N.Y.). The spectral characteristics of each paint color incorporated were established by obtaining the diffuse reflectance values at different dilutions (1:1, 1:3, 1:7, and 1:10) with Titanium White (Golden Artist Colors, Inc. New Berlin, N.Y.). After characterization, paints that displayed the correct spectral features were then combined in appropriate proportions to match the target spectrum. To account for the high viscosity of the paint, reverse pipetting was used and no volumes less than 200 μL were used for the creation of the finalized paint recipes. The mixture was then applied in layers onto the inner surface of the latex cylinder by first inverting the cast latex cylinder before painting. After the paint layers were applied, fluorescent dye-in-polymer targets were placed inside the cylinder to mimic biomarker labeled fluorescent hot-spots.

The dye-in-polymer material contained a substituted 1,8-naphthalimide fluorescent dye (Fluorol, Exciton Inc., Dayton, Ohio) that was diluted in a clear two-part polyurethane resin (AquaClear Resin, ArtMolds, Summit, N.J.). The Fluorol dye is well characterized, soluble and stable in polymer resins and its excitation and emission spectral features are close to FITC, an FDA-approved dye. FITC itself was not selected for this study because it lacks long-term photostability, while Fluorol has been used in dye laser research where photostability is required.

Phantom Fabrication

The template mold for the latex was a tubular plastic PVC mandrel with 2.5 cm outer diameter that matches the diameter of the adult human esophagus. A simple wooden dowel fixture held the PVC tube, about 25 cm long, in a vertical position during application of the latex material. The latex phantom was fabricated by applying multiple layers of latex to the PVC mandrel in order to construct a phantom with dimensions that resemble that of a typical human esophagus, approximately 25 cm in length and 2.5 cm in diameter. A layer of aluminum foil was placed between the PVC mandrel and the first layer of latex; this prevented the latex from adhering to the PVC mandrel and allowed easy separation of the phantom and the mandrel. The first layer was applied in a thin coat to prevent formation of air pockets as recommended by the supplier of the latex material. Hot air (~75° C.) was applied using a hair dryer for approximately 2 minutes to accelerate the drying process of the first layer. This process of applying thin coats of latex and then drying was repeated until the desired thickness was reached with about 10 accumulated layers, giving a phantom which has ~3 mm wall thickness. The thickness is appropriate for allowing the model to maintain both structural integrity and flexibility.

After storage for 24 hours at room temperature, the phantom was then easily removed from the PVC mandrel due to the release property of the aluminum foil layer. The aforementioned paint-gel medium was then brushed onto the inner surface of the latex cylinder in layers, with drying of each layer accelerated using the hair dryer. In this process, the paint formulation simulating healthy esophagus tissue was applied first on the entire inner surface, then the paint layer representing Barrett's esophagus was applied. Fluorescent targets were attached with transparent adhesive tape to the painted Barrett's esophagus regions to resemble biomarker labeled high-grade dysplasia (HGD) and early stages of cancer.

To fabricate the fluorescence targets, a dye-in-polymer material was formed by first dissolving the Fluorol dye powder into Part A of the polyurethane resin. Slow stirring and low temperature heating (~45-50° C.) were used to dissolve the dye in the resin. Initially a high dye-in-resin concentration (0.01 mol/L) solution was prepared and served as the master batch for further dilution into the final target concentrations in the micromole/L range. Finally the diluted Part A-dye solution was mixed with Part B at a 1:1 ratio by volume, as instructed by the polymer manufacturer. Before mixing, the Part A solution was cooled to room temperature. The dilution effect of Part B was accounted for in computing the final dye concentration in the solid polymer. Air bubbles from the mixing process were rapidly removed by using a centrifuge (Thermo Scientific Sorvall® Legend® RT) operated at 2400 RPM for 2 minutes at 2° C. The bubble-free liquid dye-in-resin mixture was then poured into 2.5 cm diameter molds. After 24 hours curing at room temperature, the rigid dye-in-polymer material was removed from the mold; the solid cylindrical castings were then sliced into thin disks using a Saw Microtome (Leica SP1600, Leica Microsystems, Nussloch, Germany). The thin (0.5 to 1.0 mm) disks were then die-cut into distinctive star shapes, which were then mounted onto the inner surface of the phantom to simulate targeted biomarker hot-spots. The concentration of these simulated fluorescent hot-spots was in the range of 1 to 100 μmol/L to match the in vivo human topical dye-peptide concentration.

The painted inner layer diffuse reflectance was measured with an Integrating Sphere (ISP-REF, Ocean Optics, Inc., Dunedin, Fla.) and a spectrometer (USB2000+, Ocean Optics, Inc). A 99% diffuse reflectance Labsphere Spectralon target (SRT-99-020, North Sutton, N.H.) was used as the reference standard. Data were analyzed and plotted offline.

Figure 5:
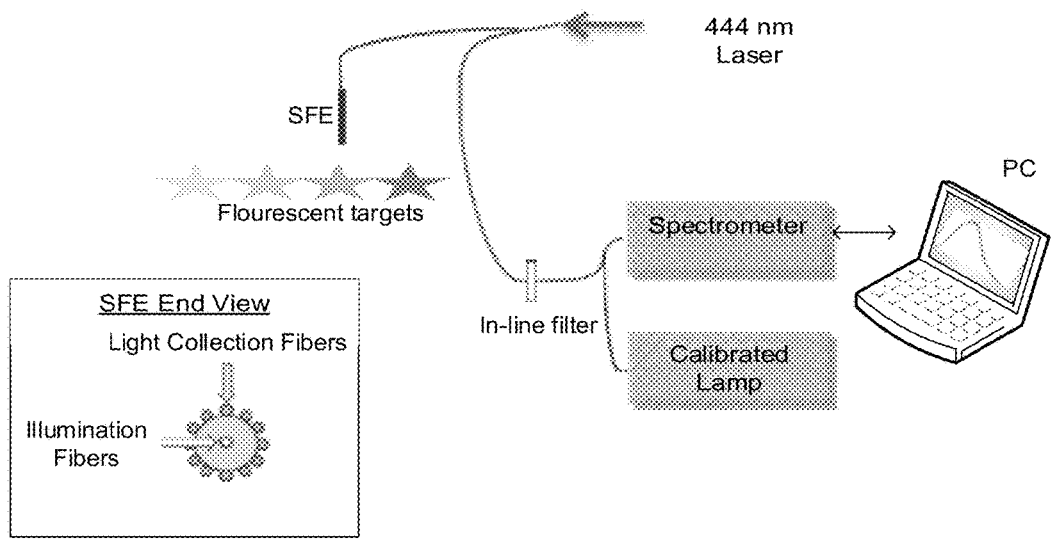
FIG. 5 shows a schematic diagram of the experimental setup to calibrate and quantify targets' fluorescence in accordance with embodiments.

The fluorescent dye-in-polymer's capability as a quantitative standard was tested for validation. The experimental setup is shown schematically in FIG. 5. These targets with concentration ratio of 1:2:3:4 were excited with a 444 nm laser (Blue Sky Research, Milpitas, Calif.) at a fixed distance and angle. The emission spectra were measured using the aforementioned Ocean Optics spectrometer; with a 450 nm longpass filter (NT62-982, Edmund Optics Inc. Barrington, N.J.) at the spectrometer entrance aperture to attenuate the excitation laser light. The emission intensity for each fluorescent target was calculated as the area under the emission curve and then, the dye concentration vs. fluorescence intensity relationship was plotted.

Imaging Platform

The SFE is an ultrathin and flexible endoscope device developed in our laboratory. It provides high-quality live videos and images with wide field-of-view (up to 100-deg FOV). The SFE has been tested in vivo in digestive tracts (esophagus, stomach, and bile duct), as well as other parts of the body such as dental tissue and airways (pig).

In the present study, a 1.2 mm diameter SFE endoscope was used. Briefly, red (635 nm), green (532 nm), and blue (444 nm) lasers can be launched collectively or selectively at the proximal end of the SFE and transmitted to the distal end using a single mode illumination fiber. Diffuse reflected light from the target is collected by a concentric ring of optical fibers surrounding the central scanning fiber and lenses. For the 1.2 mm diameter SFE, 68 high-NA (50 μm diameter) multimode optical fibers were used. Details concerning the SFE imaging system are described elsewhere.

The ability of the SFE to perform fluorescence quantification was assessed by using the aforementioned calibrated dye-in-polymer targets. Fluorescence images of the targets excited by a 444 nm laser were taken with the SFE at a fixed angle and distance. The fluorescence intensity was calculated by selecting a target region in the resultant images and calculating an average intensity for all pixels enclosed in this target region. The dye-in-polymer concentration versus fluorescence intensity relationship was then plotted and compared to the spectrometer results to verify linearity.

Figure 6:
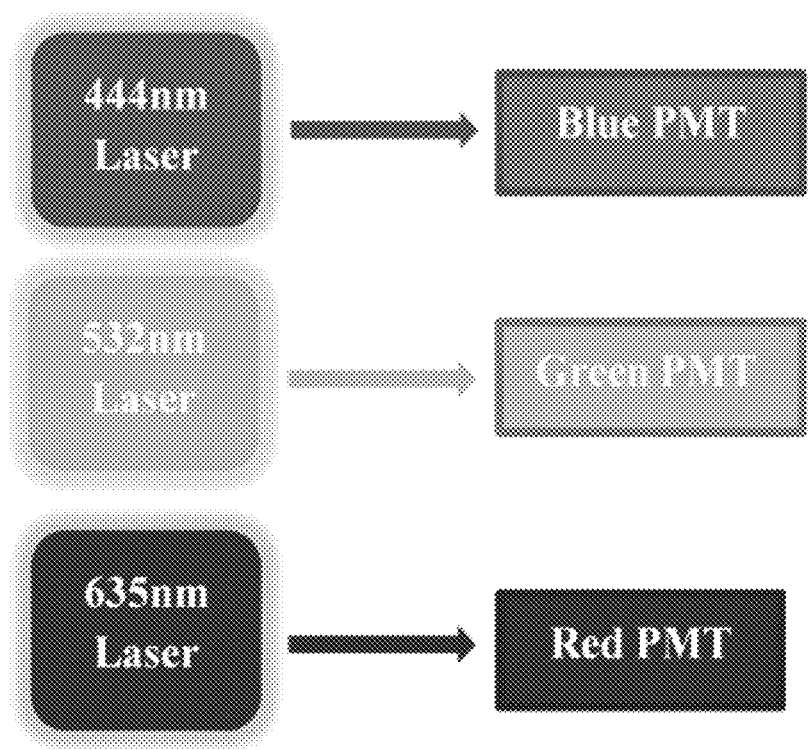
FIG. 6 shows a representation of standard SFE RGB imaging in accordance with embodiments.

White light reflectance SFE imaging of the phantom was performed and recorded. As illustrated in FIG. 6, the standard SFE RGB reflectance imaging system uses blue (444 nm), green (532 nm) and red (635 nm) laser illuminations and the RGB signals are then simultaneously detected and amplified by three individual photomultiplier tubes (PMTs).

Figure 7:
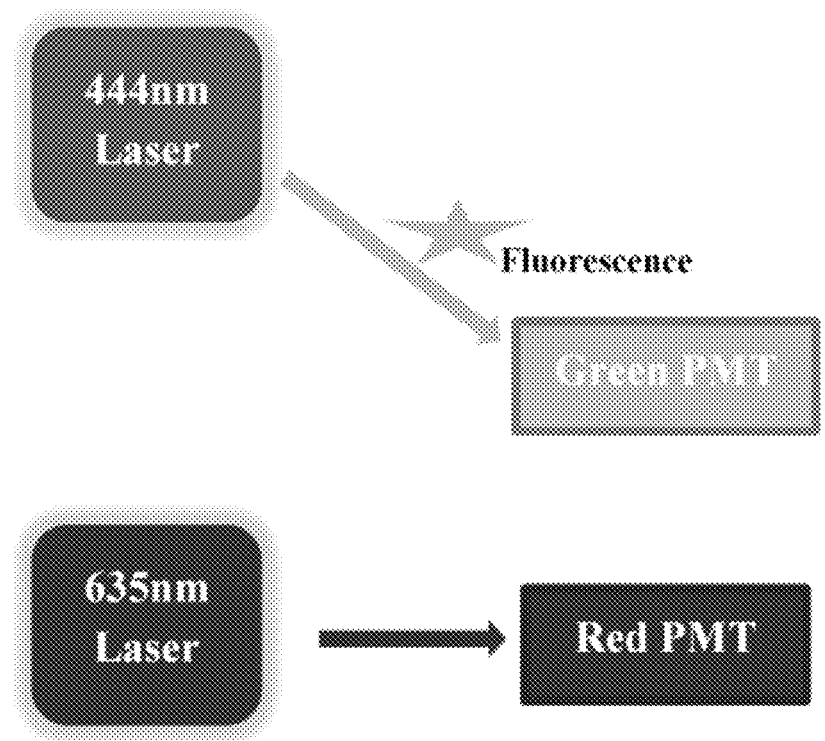
FIG. 7 shows a representation of SFE dual mode imaging, with the blue photomultiplier tube (PMT) channel inactive in accordance with embodiments.

Concurrent dual-modal imaging (FIG. 7) was achieved by configuring the SFE such that the standard green channel was converted into the fluorescence mode by deactivating the standard green laser so that only fluorescence signals in the green spectrum were recorded. The standard red channel was used for simultaneous reflectance imaging.

Exemplary methods and apparatus related to this section are provided below in Example 3.

Detecting Fluorescence Hot-Spots Using Mosaic Maps Generated from Multimodal Endoscope Imaging Fluorescence labeled biomarkers can be detected during endoscopy to guide early cancer biopsies, such as high-grade dysplasia in Barrett's Esophagus. To enhance intraoperative visualization of the fluorescence hot-spots, a mosaicking technique was developed to create full anatomical maps of the lower esophagus and associated fluorescent hot-spots. The resultant mosaic map contains overlaid reflectance and fluorescence images. It can be used to assist biopsy and document findings. The mosaicking algorithm uses reflectance images to calculate image registration between successive frames, and apply this registration to simultaneously acquired fluorescence images. During this mosaicking process, the fluorescence signal is enhanced through multi-frame averaging. Preliminary results showed that the technique promises to enhance the detectability of the hot-spots due to enhanced fluorescence signal.

Within the field of medical diagnosis there has been increasing interest in molecular imaging because of its potential to target specific bio-markers at the cellular and molecular level. In particular within the field of Gastrointestinal (GI) endoscopy, by combining fluorescence labeled molecular probes with wide-field multi-modal endoscopic devices there is significant potential to provide enhanced diagnosis and characterization of early cancer lesions by allowing for visualization of detailed biological information at the cellular or sub-cellular level.

Currently, fluorescence peptides targeting the molecular signature of cells are under investigation for imaging of adenocarcinoma and high-grade dysplasia in Barrett's esophagus. These fluorescent peptides can be combined with a multimodal wide-field endoscopic imaging system to highlight suspect regions (also known as hot-spots) within the esophageal mucosa. These hot-spots can be small and sparse and can be as small as only a few cells. Additionally the detectability and quantitative assessment of the fluorescence signal is affected by both the level of background noise and distance from the fluorescence source to the endoscope, respectively.

In order to increase the effectiveness of this new technique it is important to implement image processing algorithms and software tools, in parallel with the development of molecular probes and imaging hardware, which allows for meaningful and quantitative diagnostic information to be obtained from these small and sparse hot-spots. The image processing software, along with its graphic user interface, will perform analysis and visualization of the regions of interest from a combined white light reflectance and fluorescence image.

In the present study, a combined image mosaicking and distance compensation algorithm is applied to endoscopic video, to enhance intraoperative visualization of these hot-spots. This proposed image processing tool has been shown to improve recognition of fluorescent regions by registering together the concurrently acquired and thus co-registered reflectance images. The resulting video mosaic can be extended to create anatomical maps of the esophagus and labeled hot-spots to assist biopsy and to serve as documentation of the procedures.

Imaging Platform

In the current study, a 1.2 mm diameter scanning fiber endoscope (SFE) was used. The SFE is an ultrathin and flexible endoscope developed in the Human Photonics Laboratory. It provides wide field-of-view (up to 100-degree) and high-quality live videos and images. This endoscope device has been tested in vivo in esophagus, bile duct and stomach, as well as dental tissue, colon (mouse) and airways (pig). In the operation of the SFE, red (635 nm), green (532 nm), and blue (444 nm) laser light is launched collectively or selectively at the proximal end of the SFE and transmitted to the distal end using a single mode illumination fiber. This fiber tip is scanned in a spiral pattern at near its resonant frequency by a custom tubular piezoelectric actuator. A lens assembly provides wide field and large depth of focus of this apparent white-light illumination. Diffuse reflected and/or excited fluorescence from the target is collected by a concentric ring of optical fibers surrounding the central scanning fiber and lenses.

Figure 8:
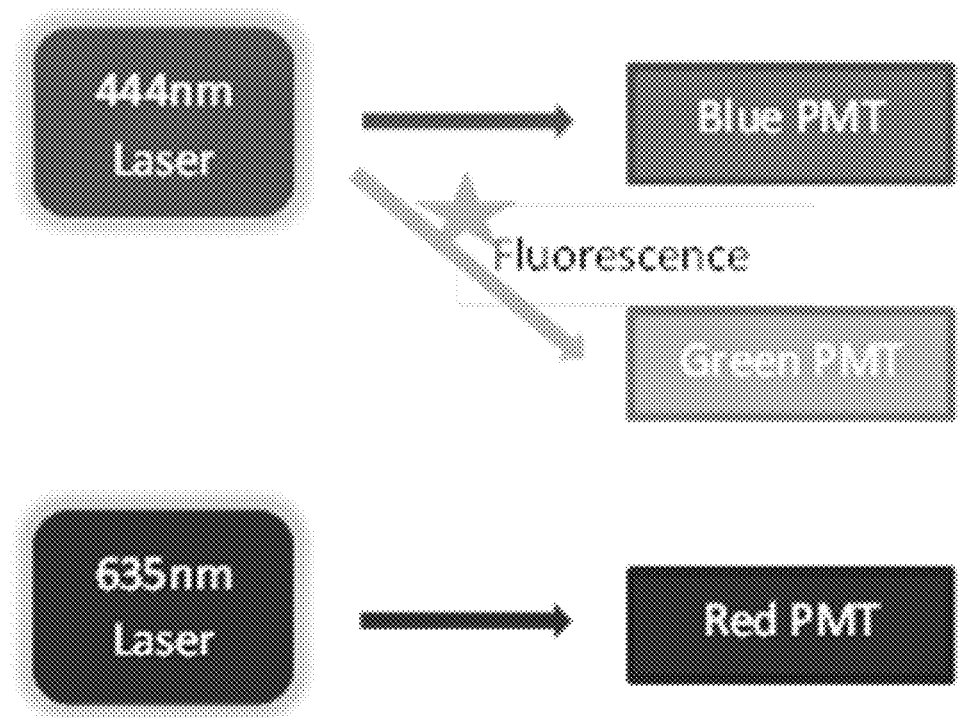
FIG. 8 shows a representation of SFE dual-mode imaging, with standard green laser inactive.

As illustrated in FIG. 6, the standard SFE reflectance imaging system uses red, green, and blue (RGB) laser illuminations. Reflected light is filtered, detected and amplified by three individual photomultiplier tubes (PMTs). To achieve concurrent dual-mode reflectance/fluorescence imaging, the green laser was turned off so that only fluorescence signals in the green spectrum were recorded. Therefore, the standard green channel was converted into fluorescence mode. The standard blue and red channels were used for simultaneous reflectance imaging (FIG. 8).

Algorithm and Software Design

Figure 9:
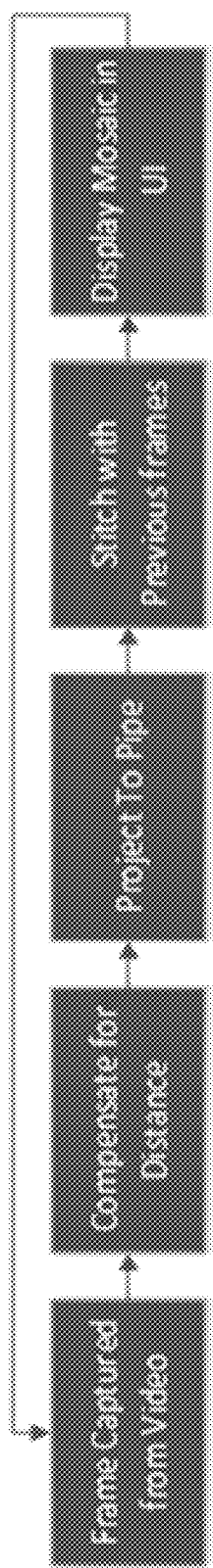
FIG. 9 shows a software design flow chart in accordance with embodiments.

The mosaicking tool we developed registers successive video frames/images using optical flow. The overall algorithm is shown in FIG. 9 below.

The software operates by first capturing images or frames from the video stream, and then for each captured frame, applying a fluorescence quantification algorithm. This quantification uses an empirically optimized non-linear ratiometric algorithm to compensate for the differences in relative distance and orientation between the fluorescent targets and the endoscope.

Figure 10:
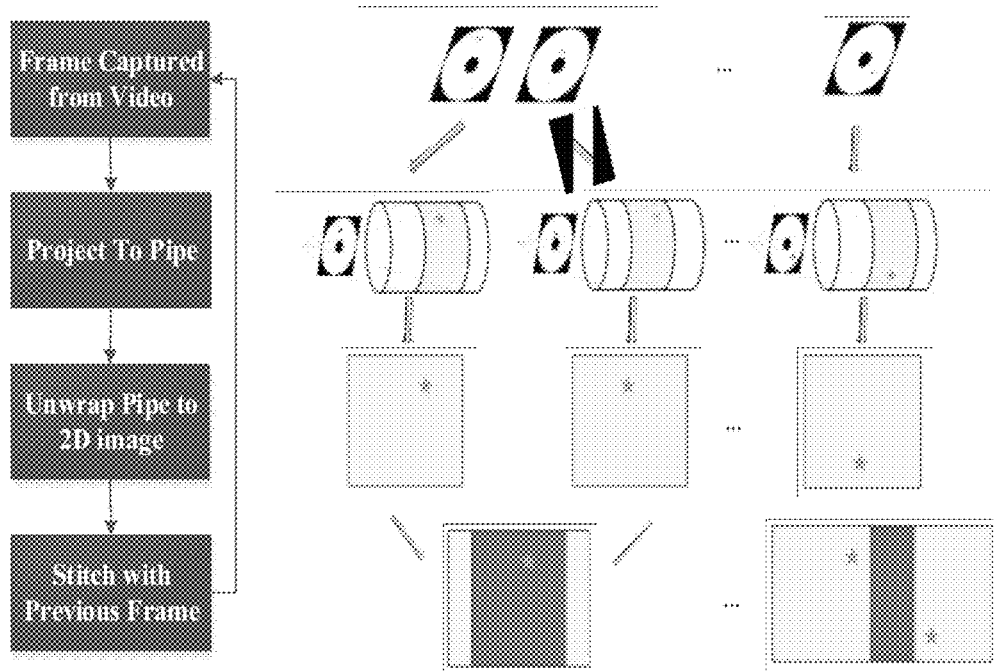
FIG. 10 shows a flowchart for the pipeline of image stitching software (left) and a graphical illustration of the pipeline (right) in accordance with embodiments.

After applying the distance compensation algorithm, we projected the image frame onto a 3D surface model. A virtual pipe or cylinder was used, as it generally represents the shape of an esophagus, and also because the surface map of a cylinder/pipe can be easily unwrapped and shown in 2D. The pipe projection is depicted in FIG. 10. FIG. 10 depicts the following steps (from top to bottom): Capture video frames, project image onto pipe model, unwrap pipe to a 2-D image, and stitch together with previous frames. The final column on the right of FIG. 10 shows result after multiple frames. The distance compensation algorithm is not shown in FIG. 10 but is applied after capturing video frames and before projecting the image onto the pipe model.

Next the image is stitched together with previous frames. During this process, to improve the registration the algorithm leveraged a unique feature of the Scanning Fiber Endoscope (SFE) in where reflectance and fluorescence images are acquired simultaneously. First, we used successive reflectance images to calculate the required transformation between frames due to the camera movement/motion. Next, this calculated transformation was applied to both the reflectance and fluorescence images to form a combined image with the previous frame. The software uses a combination of techniques in order to determine the best transformation to apply such as to minimize root-mean-square (RMS) error.

To improve processing speed, an incremental, multi-resolution approach was applied during the stitching process. The original reflectance image was projected into an image that measured 700 by 1280 pixels. This was then decreased to ¼ of its size (to 350 by 640) which lowered the resolution and decreased the time required to calculate the transformation between frames. An initial estimation of the transformation was achieved by the normalized cross-correlation method. Then, an incremental sub-pixel alignment back on the high-resolution image was conducted using the Lucas-Kanade algorithm to reach the final high-accuracy registration. Finally, a dual-mode mosaic map of the esophagus was formed by stitching successive dual-mode images together based on the calculated transformation from the reflectance image.

Exemplary methods and apparatus related to this section are provided below in Example 4.

Mitigating Fluorescence Spectral Overlap in Wide-Field Endoscopic Imaging

The number of molecular species suitable for multi-spectral fluorescence imaging is limited due to the overlap of the emission spectra of indicator fluorophores, e.g. dyes and nanoparticles. To remove fluorophore emission cross-talk in wide-field multi-spectral fluorescence molecular imaging, we evaluated three different solutions: (1) image stitching, (2) concurrent imaging with Cross-talk Ratio Subtraction algorithm and (3) frame-sequential imaging. A phantom with fluorophore emission cross-talk was fabricated and a 1.2 mm ultrathin scanning fiber endoscope (SFE) was used to test and compare these approaches. Results showed that fluorophore emission cross-talk could be successfully avoided or significantly reduced. Near term, the concurrent imaging method of wide-field multi-spectral fluorescence SFE is viable for early stage cancer detection and localization in vivo. Furthermore, a means to enhance exogenous fluorescence target-to-background ratio by the reduction of tissue autofluorescence background was demonstrated.

It is now widely accepted that optically active fluorophores, conjugated to targeted disease probes, are effective for image-guided diagnosis and surgical procedures. Fluorophore conjugates are routinely used to identify specific DNA components in flow cytometry systems, DNA microarrays, and in microscopic histology examinations (e.g. fluorescence in situ hybridization, FISH). Over the past two decades fluorophore optical probes have been evaluated for in vivo clinical imaging applications to identify pre or early stage cancerous conditions, such as neoplastic lesions in human oral tissue, dysplasia in colon, high grade dysplasia (HGD) in Barrett's Esophagus (BE), as well as screening and early detection for breast cancer, bladder cancer, and lung small cell carcinoma. Meanwhile, in vivo molecular optical imaging has also been used in ovarian cancer surgery guidance, as well as for visualization and delineation of tumor margins. It has also been shown that optical contrast agents can aid in guiding diagnosis of difficult cancers such as ovarian cancer, acute leukemia and pediatric cancer.

Many tumors express multiple cell surface and proteomic markers. Therefore, simultaneous multi-fluorophore imaging of numerous molecular targets is important for cancer diagnosis and therapy. Currently, multi-spectra fluorescence imaging techniques are employed in microscopic analysis in vitro, such as conventional immunohistology and fluorescence-assisted cell sorter. These microscopic imaging approaches are time-consuming, have a small field-of-view which means they are not applicable for in vivo cancer detection and localization. Therefore, multi-fluorophore molecular imaging techniques for clinical endoscopic imaging are needed.

One of the remaining obstacles to full implementation of multi-fluorophore imaging is the spectral width of the emission spectra as laser sources can help to reduce overlap in excitation. Although quantum dot fluorophores have narrow bandwidths (FWHM~25 nm), unresolved toxicity questions limit their application in human clinical studies. A small number of organic fluorophores, for example FITC and ICG have been approved by the FDA. In addition, most organic fluorescent dyes tend to have an asymmetric spectral profile that typically extends from the peak emission to well over 100 nm in the long wavelength tail. Overlapping emission spectra are present among most common organic dyes, for example 7-Diethylaminocoumarin-3-carboxylic acid (DEAC), Fluorescein isothiocyanate (FITC), Carboxytetramethylrhodamine (TAMARA) and Cyanine (Cy5.5), that have been developed for fluorescence labeling. Therefore, incorporating two or more fluorophore targeting agents may be problematic as a result of overlapping emission spectra. Confusion over the correct spectral intensities of multi-fluorophore labels could lead to misdiagnosis of overexpressed cell surface protein markers.

Although isolation filters can be used to separate the emission spectra, significant signal loss can occur. The fluorescence emission cross-talk problem is typically encountered in multi-color fluorescence microscopic imaging. In such diagnostic optical systems, sequential or synchronous excitation techniques can be used to separate overlapping emissions from each individual fluorophore. However, in a real time and wide-field image visualization system such as an endoscope, sequential image capture may introduce unacceptable image rendering lag times in a busy clinical work flow scenario. Therefore, we have evaluated three different options including concurrent and sequential excitation/emission image capture for distinguishing emissions from two spectrally intersecting fluorescent dye targets using a wide field scanning fiber endoscope (SFE).

The first real-time in vivo imaging of a multispectral target with the SFE was demonstrated with the identification of dysplastic "hot-spots" in a murine model of colorectal cancer. It was also shown that topically administered fluorescent molecular probes combined with endoscopic imaging, can readily identify cancerous lesions. In the diagnosis of HGD and early cancerous lesions in BE, multiple overexpressed cell surface targets, such as, epidermal growth-factor receptor (EGFR and ErbB2), hepatocyte growth factor receptor gene (MET), vascular endothelial growth factor receptor 2 (VEGFR2) have been reported. As a result, the coincident emission signature from multiple fluorescent-labeled probes is expected to provide a more sensitive and specific disease state diagnosis than a single molecular target for HGD and early cancer detection in BE We developed a color-matched, fluorescence-labeled esophagus phantom for dual-mode fluorescence-reflectance imaging with a single fluorescent molecular probe. Other applications for fluorescence molecular imaging were also demonstrated using the phantom, for example fluorescence distance compensation as well as image stitching.

In the current study, a second fluorescent dye was added to the phantom to construct a two-dye fluorescence model that represents imaging with emission cross-talk. Three approaches: (1) image stitching, (2) concurrent imaging with Cross-talk Ratio Subtraction (CRS) algorithm, and (3) frame-sequential imaging were evaluated for the removal/reduction of fluorescence emission cross-talk in a wide-field multi-spectral fluorescence endoscopic system. For each approach, we describe the concept, outline the method of execution, and present evaluation test results. Finally, the strengths and limitations of each approach are compared and discussed. Each of the three proposed methodologies shows promise for wide-field multi-spectral fluorescence endoscopic imaging with mitigated dye emission cross-talk. Furthermore, they are also applicable to the reduction of autofluorescence and thus enhancement of target-to-background ratio during in vivo molecular imaging.

Phantom Model

Two-Dye Fluorescence Targets Fabrication and Calibration

Fluorescent dye-in-polymer targets were fabricated to represent the molecular probe targeted tissue biomarker. Briefly, two dyes: chemical name Fluorol 555 (Exciton Inc., Dayton, Ohio) and Pyrromethene 597-8C9 (Exciton Inc., Dayton, Ohio) were dissolved in a clear polyurethane resin using a master-batch dilution protocol described in.

The Fluorol (FL) and Pyrromethene (PM) dyes were chosen as they are well characterized soluble and stable in polymer resins. Moreover, their emission spectral features are close to Coumarin (DEAC), Fluorescein (FITC), 5-Carboxytetramethylrhodamine (5-TAMRA), Cyanine (Cy5.5), 5-Aminolevulinic Acid Hydrochloride (5-ALA) and Indocyanine Green (ICG) dyes, which will be used for the in vivo human subject studies. The FDA approved dyes were not selected for this study because they lack long-term photostability, while the currently selected FL and PM dyes have been used in dye laser research where photostability is required.

The liquid resin dye-in-polymer material was cured in a 2.5 cm-diameter cylindrical mold and the solid material was then sliced into thin disks using a Saw Microtome. The final fluorescence targets were die-cut into distinctive star shapes with an outside dimension of ~0.5 cm. The molar concentration of the fluorescent targets was in the range of 1-100 μmol/L to match the molecular probe concentrations topically applied for in vivo human subject studies.

In the current study, 3 types of dye-in-polymer targets were fabricated: the FL-only, the PM-only, and the FL-PM mix. The FL-PM mix targets represented the spatial co-location of molecular probes at the biomarker hot-spots. The FL and PM dye-in-polymers' quantitative capability was then tested using a calibrated spectrophotometer. A 442 nm laser (Blue Sky Research, Milpitas, Calif.) was used as the excitation for the FL target and a 532 nm laser (Blue Sky Research, Milpitas, Calif.) was used for the excitation of the PM target, and accordingly, a 450 nm in-line long-pass filter (NT62-982, Edmund Optics Inc. Barrington, N.J.) or a 532 nm in-line rejection filter (NT63-346, Edmund Optics Inc., Barrington, N.J.) was used individually for each excitation wavelength to attenuate excitation laser light. The fluorescence emission spectra of the two dye targets, measured from a spectrometer (USB2000+, Ocean Optics, Inc), were plotted and overlaid to represent the dye cross-talk issue.

Barrett's Esophagus Phantom

In the current study, a color-matched Barrett's esophagus phantom was used. The fluorescent dye-in-polymer targets were attached with transparent adhesive tape to the simulated Barrett's esophagus regions to resemble molecular probe labeled high-grade dysplasia and early cancerous hot-spots of the mucosal surface.

Imaging Platform

A 1.2 mm outer diameter (OD) scanning fiber endoscope (SFE) was used in the current study. The laser-based SFE technology was developed in our laboratory for the purpose of performing high-quality, wide field (FOV up to 100 degree) video imaging via an ultrathin and flexible endoscope. Unlike a conventional passive imaging system that uses diffuse light illumination, the SFE incorporates low power blue (442 nm), green (532 nm) and red (635 nm) laser illumination. The lasers can be collectively or selectively launched at the base station and sent to the distal end of the SFE scope via a single-mode optical fiber. The resulting laser beam is focused by a lens assembly, and scanned in a spiral pattern by a tube piezoelectric actuator across the field of view. Reflected and fluorescence light are both collected by a concentric ring of high numeric aperture multimode optical fibers surrounding the central fiber scanner and lens assembly. The collected light is focused onto two dichroic beam splitters and then separated into three (Red, Green, and Blue respectively) detection channels. Prior to impinging on the photomultiplier tube (PMT) detection channel, the color separated light beam passes through a high optical density band-pass filter. The SFE system software then maps the synchronized PMT detection signals as points in the spiral scan pattern to the two dimensional pixel position of the RGB digital display. At a standard setting, the SFE outputs 500-line images at a frame rate of 30 Hz.

SFE Imaging Solutions For Dye Cross-Talk

Figure 11:
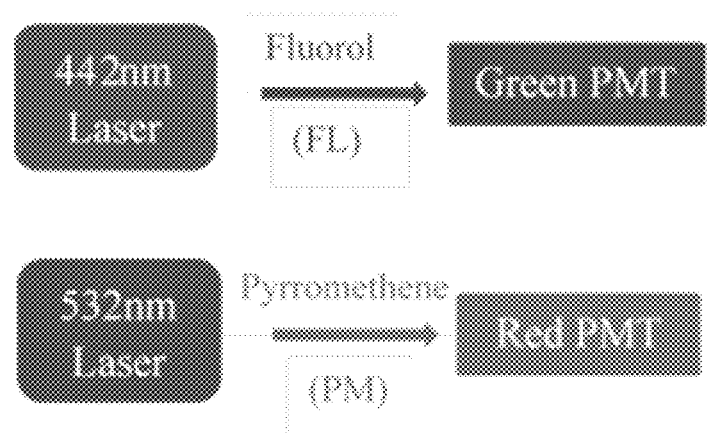
FIG. 11 shows a representation of SFE excitation lasers and output channels for two-dye fluorescence imaging in accordance with embodiments.

In the present study, the 442 nm laser was used as excitation for the FL dye-in-polymer targets and the green detection channel was used to detect its fluorescence emission, whereas the 532 nm laser was used for the excitation of the PM dye-in-polymer targets and the red detection channel was used to detect its fluorescence emission, as illustrated in FIG. 11. The 442 nm laser was used as excitation for the FL dye targets and the green detection channel was used to detect its fluorescence emission, whereas the 532 nm laser was used for the excitation of the PM dye targets and the red detection channel was used to detect its fluorescence emission.

For quantitative two dye imaging, the automatic gain control in the SFE system was turned off. The gain and offset on the PMTs as well as the electronic digital display were also calibrated and maintained at a constant value. SFE images and video frames were captured and saved through the system software and analyzed off-line. In the current study, a color-matched Barrett's esophagus phantom was used. Three types of aforementioned fluorescence targets: FL dye only, PM dye only, and FL-PM mix were all placed in the phantom mucosal surface for the dual-fluorescence imaging.

To mitigate the fluorescence dye emission cross-talk, three approaches were implemented and evaluated:

Merging Multispectral Fluorescence Scans Using Image Stitching

In separate image capture scans, alternating once between excitation lasers, a continuous series of images were captured as the SFE scope was moved along the central axis of the phantom. All the fluorescent targets were distributed on the phantom surface but only a single fluorescent specie was excited in each scan. An image stitching algorithm was applied to 40 to 50 video frames of each scan and generated a two dimensional (2D) anatomical map containing the fluorescent hot-spots. Finally, these individual 2D maps were spatially registered and combined using shared anatomical features. This wavelength separated image collection approach has minimal dye emission cross-talk, as the dyes are excited at separate wavelengths.

SFE Dual-Fluorescence Imaging

Figure 12:
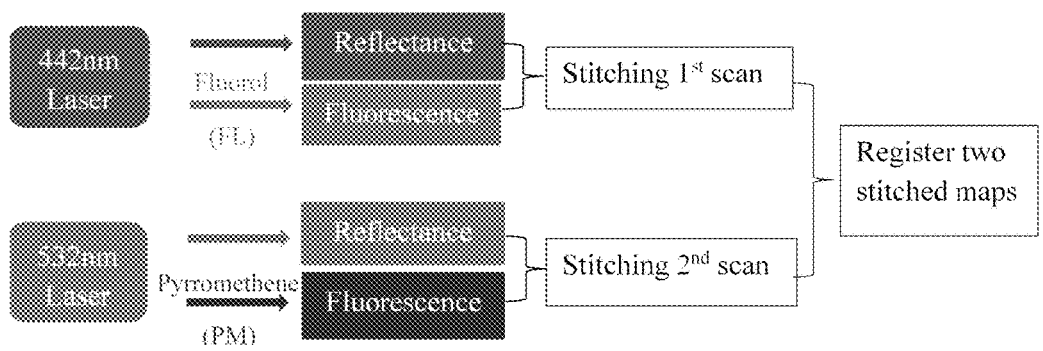
FIG. 12 shows a flowchart for the concept of two-dye imaging using image stitching in accordance with embodiments.

A simplified flowchart containing the key steps of the image stitching approach is shown in FIG. 12. At first, FL target fluorescence and reflectance images were recorded. To concurrently obtain the fluorescence and reflectance images, the 442 nm laser was turned on as illumination source and the 532 nm and 635 nm lasers were disabled. The reflectance image was captured in the blue channel and the fluorescence was captured in the green channel.

In the first scan shown in FIG. 12, concurrent FL target fluorescence and reflectance images were recorded, and then imported into the image stitching software to generate a 2D FL dye fluorescence hot-spot map. In the second scan shown in FIG. 12, concurrent PM target fluorescence and reflectance images were recorded, and a 2D PM dye fluorescence hot-spot map was then generated. The software then spatially registered and merged the individual FL and PM map into a combined map with FL-only, PM-only and FL-PM mix targets.

Once the first scan was finished, the recorded images were imported into the image stitching software to generate a 2D unwrapped map of the lower esophagus with FL fluorescence hot-spots. The 2nd scan for the PM target followed the same procedure, except that in this case, the 532 laser was turned on as illumination source whereas the other two lasers were disabled. The reflectance image of the lower esophagus phantom and the targets were captured in the green channel and the PM fluorescence was captured in the red channel. A 2D unwrapped map of the lower esophagus with PM fluorescence hotspots was then generated. The 2D FL and PM fluorescence stitched maps were then spatially registered and merged into a map showing all three types of fluorescence targets: PM, FL and PM-FL mix.

Image Stitching Algorithm and Software Design

As described in the previous section, Image stitching is used to combine multiple frames from the endoscopic scan into a single 2-D map. This section will further describe the approach and process involved.

As illustrated in FIG. 10, the image stitching software operates by first capturing images or frames from the video stream, and then the endoscopy image frame is projected onto a 3D surface model. A virtual pipe/cylinder surface model is used as it represents the general shape of an esophagus. After the pipe projection, the texturized surface map of the cylinder is unwrapped and shown in 2D. Next, the 2D unwrapped individual frame is stitched together with the previous frame. This process is achieved by leveraging the SFE's unique feature where reflectance and fluorescence images are acquired simultaneously. Reflectance images are used to calculate the required transformation between frames due to the camera motion. For this step, a normalized cross-correlation method is first applied to calculate the initial transformation and align the frames together at pixel level, then, optical flow (Lucase-Kanade) algorithm is used to reach a higher-accuracy image alignment at a sub-pixel level. The calculated transformation is then applied to both current reflectance and fluorescence images to form a combined image with the previous frame. By stitching successive frames together, a dual-mode reflectance-fluorescence 2D mosaic map of the lower esophagus is then formed. The 2D mosaic map for individual fluorescence scan can then be registered together to form a final composite mosaic map with multi-spectral fluorescence hot-spots. The mosaicking software was originally created to assist biopsies and document findings during fluorescence endoscopy for HDG and early cancerous lesions in BE. This approach also demonstrated enhanced signal-to-noise ratio (SNR) fluorescence imaging using co-acquired high SNR reflectance imaging.

Concurrent Multispectral Fluorescence Imaging

In this approach all fluorescent species are illuminated concurrently with both lasers and have their emissions collected simultaneously. The dye emission cross-talk is mitigated by applying a FL Cross-talk Ratio Subtraction (CRS) algorithm:

$$CR\_dye\_I = \frac{FL\_dye\_I \text{ in } R}{FL\_dye\_I \text{ in } G} \qquad \text{Eq. (1)}$$

$$\text{Corrected } R_I = \text{Measured } R_I - \text{Measured } G_I \times CR \qquad \text{Eq. (2)}$$

Where CR=Cross-talk Ratio; R=red detection channel; G=green detection channel; I=intensity. Equation 2 applies when green channel has contribution from a single dye.

At the step 1, a constant: FL dye Cross-talk Ratio (CR) is calculated from Equation (Eq.) 1 by experimentally imaging FL dye targets alone at various intensities and distances in the phantom. At step 2, concurrent laser wavelength excitation is enabled. The FL dye cross-talk signal (calculated as Measured $G_I$*CR in Eq. 2) is subtracted from the red detection channel, and the corrected PM dye red signal intensity is therefore obtained.

Concurrent SFE Dual-Fluorescence Imaging

A series of SFE calibration experiments were performed with the dye-in-polymer materials. First, a test was carried out to verify that the laser excitation wavelengths exclusively excited one of the two dye targets, for example, 442 nm laser alone does not cause PM fluorescence emission, and the 532 nm laser alone does not cause FL fluorescence emission. Next, the linearity of the fluorescence detection channels (G and R) was tested by plotting the fluorescence images' pixel intensity versus the dye molar concentration of the targets. Then, the aforementioned Cross-talk Ratio (CR) was calculated from images with 442 nm excitation only. The fluorescence intensity was obtained by selecting a target region in the resultant images and calculating an average intensity for all pixels enclosed in this target region. Also, the consistency of the CR was tested by plotting it against the distance of the SFE to the fluorescence targets. This CR is then applied to the concurrent red detection channel based on Eq. 1, to subtract out the FL dye emission cross-talk. Concurrent images and videos are then acquired.

Figure 13:
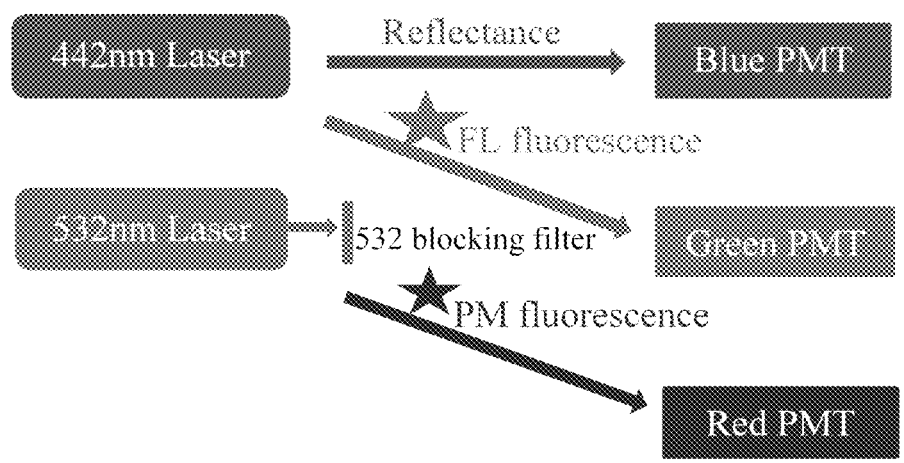
FIG. 13 shows a representation of dual-mode fluorescence-reflectance two-fluorophore imaging in accordance with embodiments.

The SFE setup is illustrated in FIG. 13. The 632 nm laser is powered off. The 532 nm laser is blocked in front of the green detection channel, only allowing fluorescence signal to pass through. Therefore, the green and red detection channels are configured for fluorescence imaging whereas the blue detection channel is for reflectance imaging. The 442 nm and 532 nm lasers were turned on for the simultaneous illumination of FL and PM fluorescence targets respectively. The green detection channel was used to receive the FL emission signal whereas the red detection channel was for the PM emission. A short wave pass filter (SP01-532RU, Semrock, Rochester, N.Y.) was used in the green detection channel to block the 532 nm excitation laser.

Sequential Multispectral Fluorescence Imaging

Figure 14:
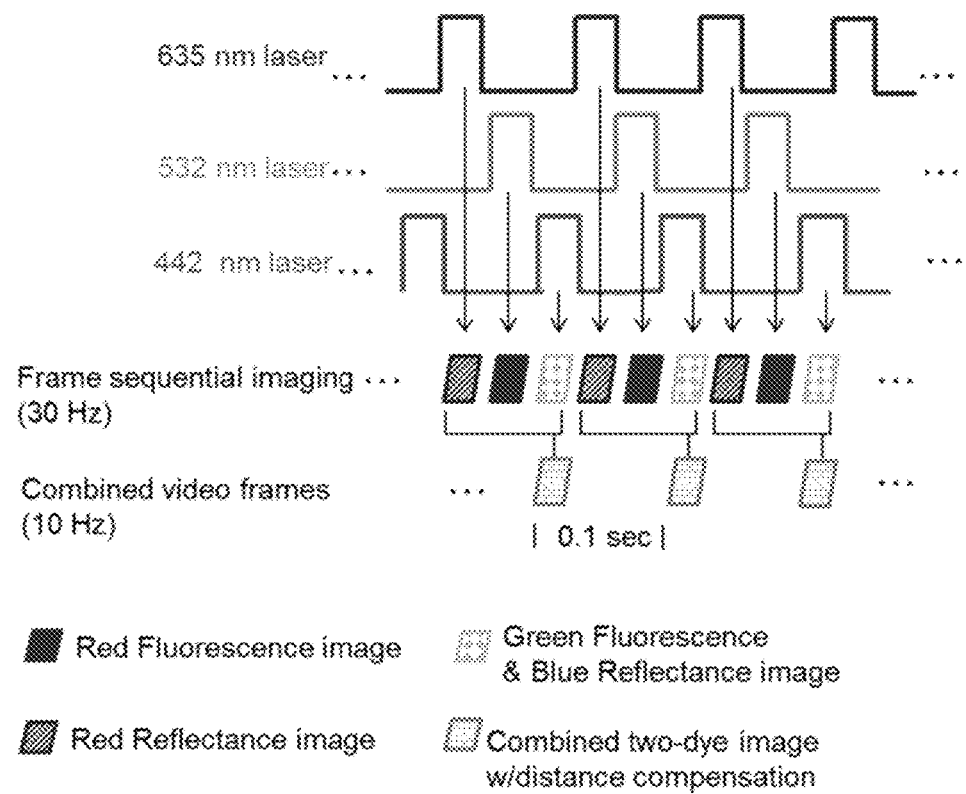
FIG. 14 shows a graphic illustration of the frame sequential multispectral fluorescence imaging technique in accordance with embodiments.

This method addresses the dye emission cross-talk problem through excitation and collection of one fluorescence species at a time. However, instead of using image stitching to post-process and composite the multiple fluorescence target images, this sequential imaging approach works by sequentially activating the excitation lasers in an interleaved pulsed mode as illustrated in FIG. 14. Briefly, each of the red, green and blue lasers was turned on individually and sequentially. Meanwhile, red reflectance, PM red fluorescence, and FL green fluorescence were received in the detection channels sequentially at 10 (30/3) Hz. The red reflectance frames were acquired to enable the Distance Compensation (DC) algorithm for quantitative fluorescence imaging. When the DC algorithm is not needed for the application, only PM red and FL green fluorescence are acquired at 15 (30/2) Hz. In normal operation, red, green and blue reflectance are used for conventional "white light" color imaging. As a result, the fluorescence signals are individually acquired in an interleaved mode and then composed at near real time.

SFE Dual-Fluorescence Imaging

A new SFE system feature was implemented to enable the excitation lasers to be sequentially activated, so that the red, green and blue lasers were turned on one at a time. In the detection channels, red reflectance, PM red fluorescence, and FL green fluorescence were received sequentially at 30 Hz (10 Hz for each). The red reflectance images were acquired to enable the application of the Distance Compensation algorithm. This quantification uses an empirically optimized non-linear ratiometric method to compensate for the difference in relative distance and orientation between the fluorescence targets and the distal end of the SFE probe. The composite rendering was formed from sequential red fluorescence, green fluorescence and blue reflectance images merged together into full RGB images.

Exemplary methods and apparatus related to this section are provided below in Example 5.

EXAMPLES

The following examples are included to further describe some aspects of the present invention, and should not be used to limit the scope of the invention.

Example 1

Detection Sensitivity of Scanning Fiber Endoscope with Multiple Fluorescence-Reflectance Imaging Channels for Guiding Biopsy This example is related to the above section titled "Scanning Fiber Endoscope with multiple fluorescence-reflectance imaging channels for guiding biopsy."

The detection sensitivity of the SFE was evaluated with a series of small-volume (50 uL) and low-concentration (nanomolar to micromolar) fluorophore dilutions. All experimentation used low laser output powers of each channel (2.2 mW 448 nm, 3.2 mW 488 nm, and 5 mW 642 nm) measured with Newport optical power meter (Model 1830-C). In the current study, the fluorescein and Cy5.5 dyes were chosen for the sensitivity test, since they were to be used in the next step ex vivo or in vitro image applications.

The multispectral SFE detection sensitivity limit was 5 nanomolar for the fluorescein dye and 10 nanomolar for the Cy5.5 dye at video rate with signal-noise-ratio (SNR) at 2:1. The SFE detection channels' linearity was demonstrated on the 0-100 micromolar scale. The same method was also used here, by plotting the dye concentration versus image intensity relationship to evaluate the green and red detection channel at 0-100 nanomolar scale. Here, shown in FIG. 15A-15B, the linearity was confirmed for low (nanomolar) concentration range. Each data point was an average of n=5 and error bar represented the variability in the fluorescence signal intensity measurement. Meanwhile, the significant increase (20×) in signal collection of the 2.1-mm scope was also confirmed by imaging the same fluorescence target and comparing its intensity to that of the 1.2-mm scope.

Conclusion

This study demonstrated the clinically essential features for a newly developed multispectral scanning fiber endoscope operating in wide-field fluorescence imaging mode at video rates. The endoscope's mechanical features, small size, and flexibility are achieved with equally important optical resolution and high detection sensitivity. Incorporating the SFE fluorescence detection system into other clinical devices such as the working channel of conventional flexible endoscopes and colonoscopes extends its range of applications. Used separately, the SFE scope can provide wide-field fluorescence imaging in small ducts and tissue cavities, such as the lung, bile duct, and blood/vascular system etc. Meanwhile, the small scale imaging technology can be extended to transnasal or pinhole brain surgeries for minimally invasive fluorescence guided tumor resection.

Figure 15A:
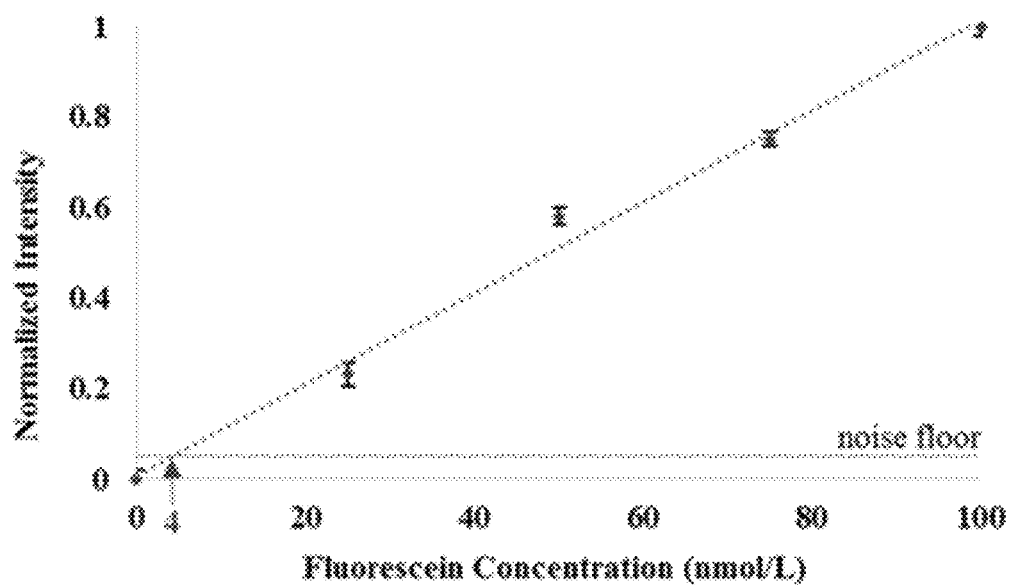
FIG. 15A shows fluorescence intensity as a function of fluorescein concentration.
Figure 15B:
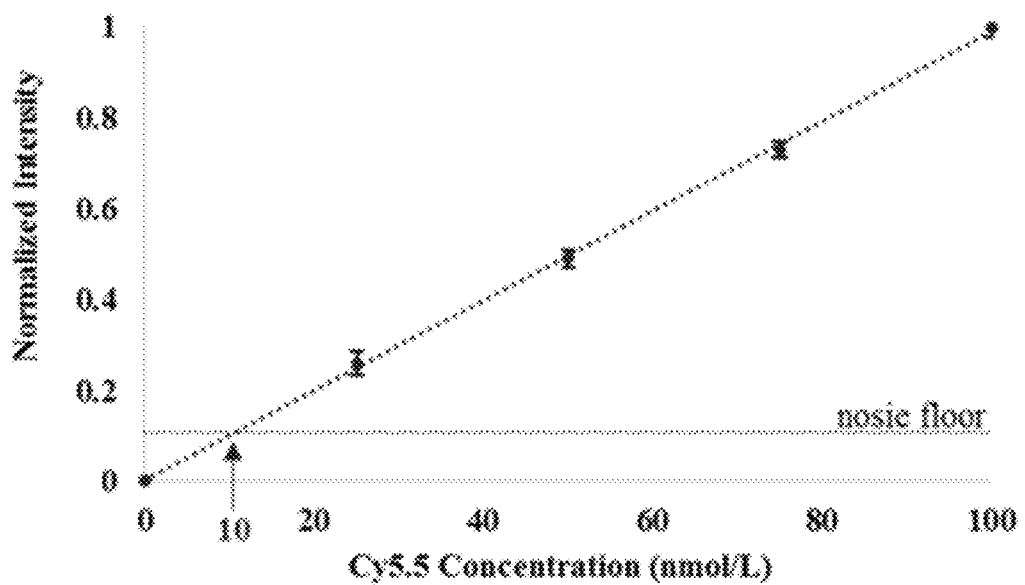
FIG. 15B shows fluorescence intensity as a function of Cy5.5 concentration in accordance with embodiments.

Secondly, concurrent laser excitations with separate detection channels across the ultraviolet to visible to infrared spectra, allow customized designs for almost any wavelength combinations. This system design flexibility expands the choice of fluorophore conjugate probes for various applications. Having separate individual detection channels for different fluorescence molecular probes, each channel laser illumination and detection setting can be optimized individually for the greatest SNR. Diagnostic signal threshold for each molecular probe can also be adjusted separately before combined multichannel/multicolor display visualizations to the clinician. The SFE noise floor was estimated to be at equivalent concentrations of 4 nmol/L and 10 nmol/L for fluorescein sodium and Cy5.5 NHS ester based on linear analysis of the data (FIG. 15A-15B). This high sensitivity provides a means to detect early cancers and pre-cancers in vivo and guide biopsy and surgical resection. At 2:1 image contrast ratio, the current visual sensitivities for fluorescein sodium and Cy5.5 NHS ester were determined at 5 nmol/L and 10 nmol/L using SFE scope output power of 3 mW and 5 mW respectively. This low laser power provides a higher level of safety for patient and clinical staff.

Furthermore, quantitative fluorescence imaging for in vivo clinical application also requires a high target-to-background ratio (T/B) during tissue imaging. The design of multispectral SFE is uniquely suited for the implementation of a real time AF mitigation algorithm, which can improve the in vivo fluorescence T/B by >50 fold which significantly improves the sensitivity and specificity of molecular probe imaging of exogenous fluorophores.

In conclusion, preliminary results show that the newly developed SFE technology has met many of the essential requirements for clinical implementation, and will be evaluated in upcoming clinical/pre-clinical trials for the detection of early stage cancer and image guided biopsy.

Example 2

Application of Multi-Spectral Scanning Fiber Endoscope with Concurrent Autofluorescence Mitigation for Enhanced Target-to-Background Ratio Imaging This example is related to the above section titled "Multispectral Scanning Fiber Endoscope with concurrent autofluorescence mitigation for enhanced target-to-background ratio imaging."

Validation of the AF Mitigation

As illustrated in FIG. 3A-D, it is assumed that the AF emission spectral profiles were nearly identical for the 445-nm excitations and the 488-nm excitations, so that a constant ratio can be applied to AF1 (in the AF channel) to calculate AF2 (in the detection channel).

To validate this assumption, we acquired the individual AF emission spectra of the two excitation wavelengths using a quantitative fluorescence imaging instrument—the IVIS Spectrum (Perkin-Elmer, Norwalk, Conn.). Ex-vivo porcine esophagus epithelium tissue was used in this validation study for the imaging. Porcine esophagus is often used as a model for human esophagus tissue because its morphology, histology and biochemistry are similar to that of human. Two excitation filters (Perkin-Elmer, Norwalk, Conn.) 430/±15 nm and 460/±15 nm from the IVIS system were used to closely match with the SFE's 445 and 488 nm lasers, and AF emission were acquired from 500-800 nm and their intensities plotted to form the AF emission spectra.

Results

Figure 16A:
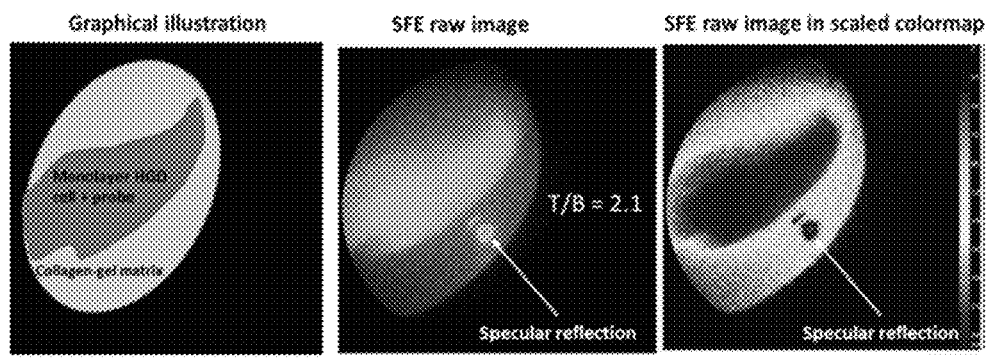
FIG. 16A-16B show real time AF and specular reflection mitigation on a tissue phantom in accordance with embodiments.

The tissue phantom, illustrated in FIG. 16A (left), showed the targeted area with high-grade dysplasia (HGD) cell and an AF background. A T/B of 2 was calculated for the targeted fluorescein fluorescence area (FIG. 16A (middle), and FIG. 16A (right) showed the original image in a scaled intensity map) and the adjacent background. When applying AF mitigation algorithm, the T/B was consistently enhanced above 50. No AF was observable outside of the targeted areas on the fluorescein imaging channel except for minimal electronic noise (FIG. 16B (middle and right). Furthermore, using the same approach, any bleed-through specular reflectance signals in the fluorescein/Green channel are subtracted based on the signals from the AF/Blue channel, at the same pixel location.

Figure 16B:
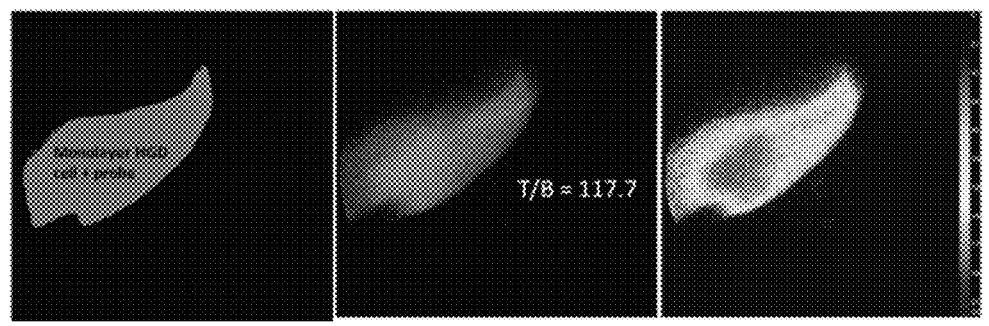

The results shown in FIG. 16B demonstrate the significant improvement in T/B and elimination of specular reflection after applying the algorithm. Specifically, the T/B ratio was increased from 2.1 to 117.7 and the specular reflection from FIG. 16A was removed, resulting in a sharp and clear delineation of the targeted HGD cell region.

Figure 17:
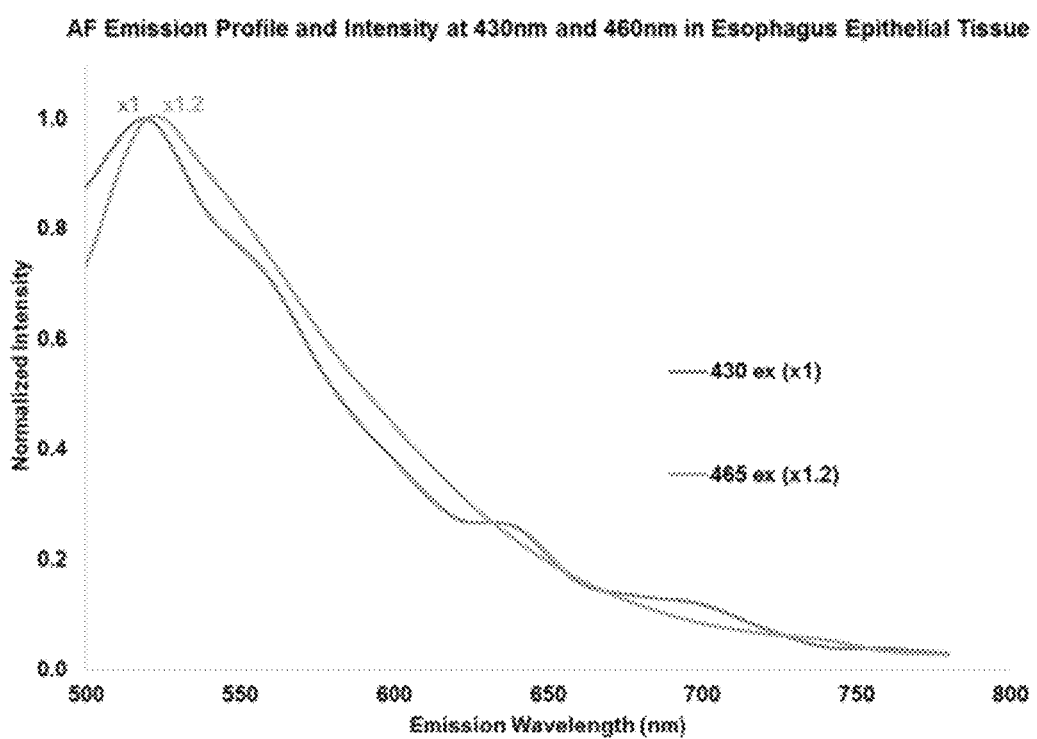
FIG. 17 shows emission profiles under two different excitation lasers (430 nm and 460 nm) in esophagus epithelial tissue in accordance with embodiments.

In the AF verification study, porcine esophagus tissue was acquired from a certified abattoir following the Standard Operating Procedure for porcine tissue by the University of Washington. FIG. 17 showed that the AF emission profiles plotted from emission spectra (500-800 nm) measured with two closely spaced excitation sources (430±15 nm and 460±15 nm) were nearly identical. Their emission signal intensities were also nearly equivalent (FIG. 17).

Fluorescence molecular imaging is often limited by the abundant tissue autofluorescence (AF) background, resulting in a low target-to-background ratio (T/B), and thus decreasing the sensitivity and specificity of this type of imaging modality.

In the present study, we implemented and demonstrated an AF mitigation algorithm on a newly developed wide-field multispectral scanning fiber endoscope (SFE) at 30 Hz video rate. Significantly enhanced T/B was realized by using concurrent excitation and detection of multiple laser wavelengths to separate the AF background from the targeted fluorescence. On a tissue phantom featuring collagen-associated background AF and fluorescein molecular probe targeted high-grade dysplasia (HGD) cells, we achieved a >50-fold T/B with the real time AF mitigation algorithm.

Meanwhile, the same algorithm can also eliminate bleed-through specular reflection, and therefore reduce false-positive signals for wide-field fluorescence molecular imaging. The ability to eliminate false positive hot spots of fluorescence in molecular imaging of disease will allow robust computer aided diagnostic algorithms to be developed for automated surveillance and screening.

Furthermore, we verified the basic assumption of the AF mitigation algorithm using a gold-standard quantitative imaging device. It was confirmed that the AF emission spectral profiles were nearly identical for closely spaced excitation wavelengths (445 and 488 nm), and therefore, a constant pre-calibrated ratio can be applied to calculate and then subtract the AF signal in the target/fluorescein detection channel.

Finally, this was the first use of the Coherent® OBIS Galaxy™ beam combiner system (Coherent, Santa Clara, Calif.) for concurrent wide-field multichannel fluorescence endoscopy. The multi-laser source coupled to a single-mode optical fiber ultimately proved to be plug-and-play with fiberoptic connectors and straightforward user interface. Power levels at the endoscope distal end (445 nm=10 mW and 488 nm=20 mW) were more than sufficient and spectrally clean, which provided bright AF and fluorescein imaging of biological specimens for demonstrating this new video-rate, pixel-level T/B enhancement in vitro.

Multispectral fluorescence imaging with AF subtraction is necessary for quantitative molecular imaging. By eliminating background AF and specular reflections, computer aided diagnosis of endoscopic images are more quantitative and robust.

Example 3

Application of Color-Matched and Fluorescence-Labeled Esophagus Phantom

This example is related to the above section titled "Color-matched and fluorescence-labeled esophagus phantom."

We developed a stable, reproducible three-dimensional optical phantom for the evaluation of a wide-field endoscopic molecular imaging system. This phantom mimicked a human esophagus structure with flexibility to demonstrate body movements. At the same time, realistic visual appearance and diffuse spectral reflectance properties of the tissue were simulated by a color matching methodology. A photostable dye-in-polymer technology was applied to represent biomarker probed "hot-spot" locations. Furthermore, fluorescent target quantification of the phantom was demonstrated using a 1.2 mm ultrathin scanning fiber endoscope with concurrent fluorescence-reflectance imaging.

Color Matching and Diffuse Reflectance

Initially paint recipes were formulated wherein constituent paint ratios were adjusted so that the resulting diffuse reflectance values approached that of the published non-dysplastic BE. As the paint reflectance values approached those of the published spectrum, a disparity emerged between the formulated paint recipes and the widely reported salmon-red color appearance of Barrett's esophagus.

Figure 18A:
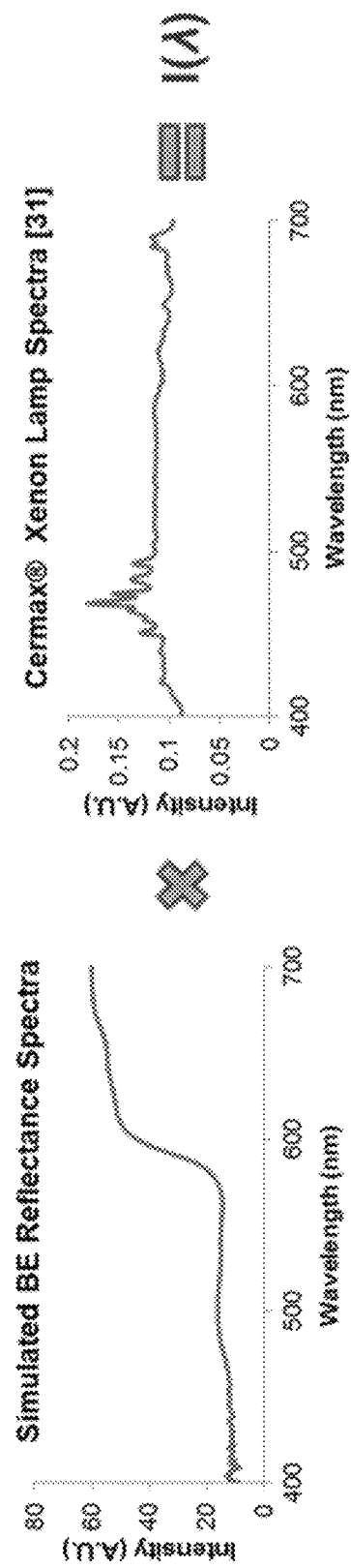
FIG. 18A-18C shows a summary diagram of the CIE color calculation methodology in accordance with embodiments.
Figure 18B:
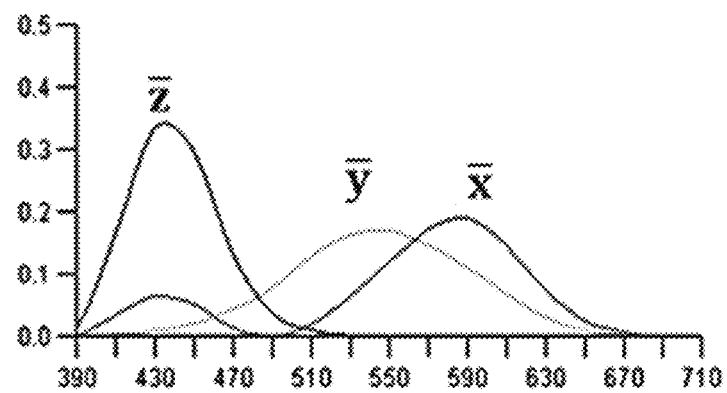
Figure 18C:
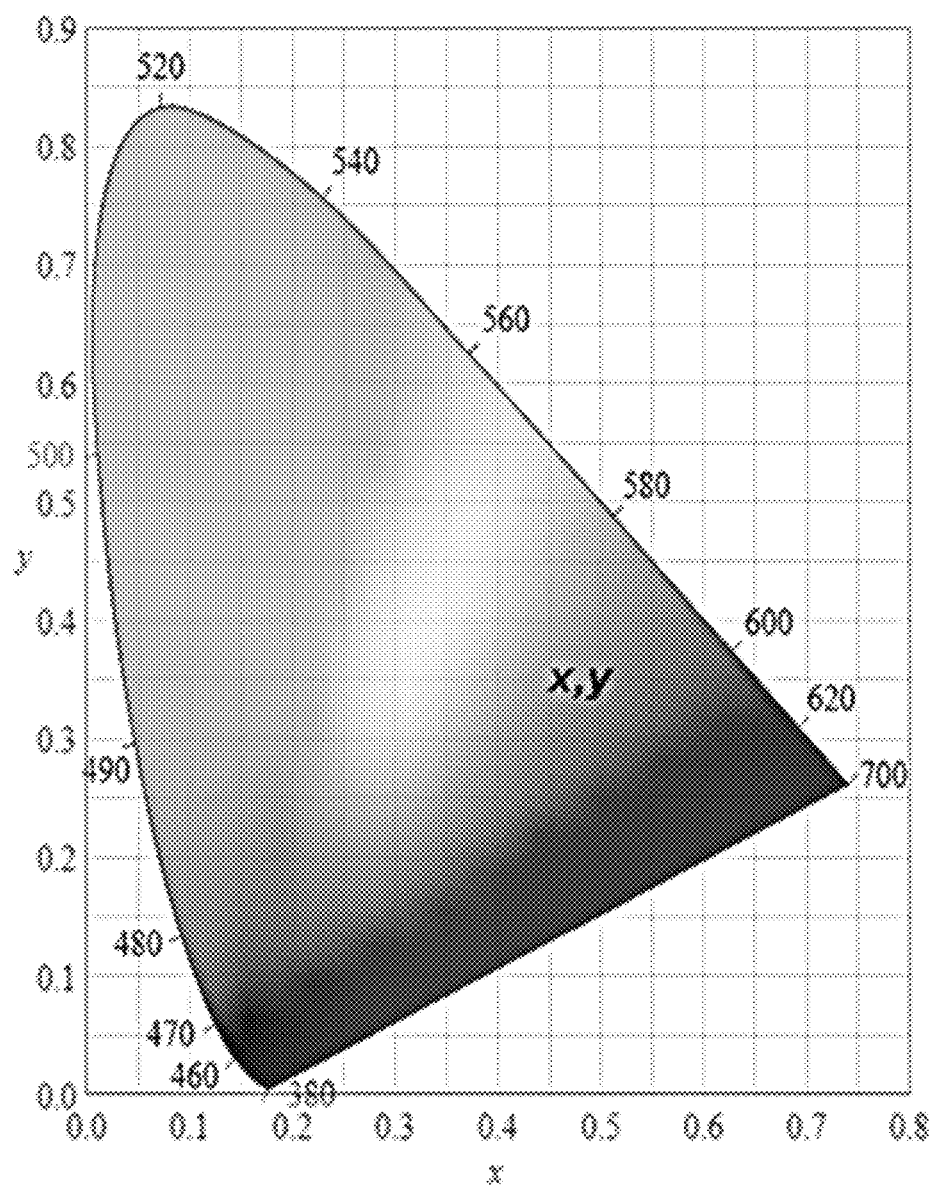
Figure 19:
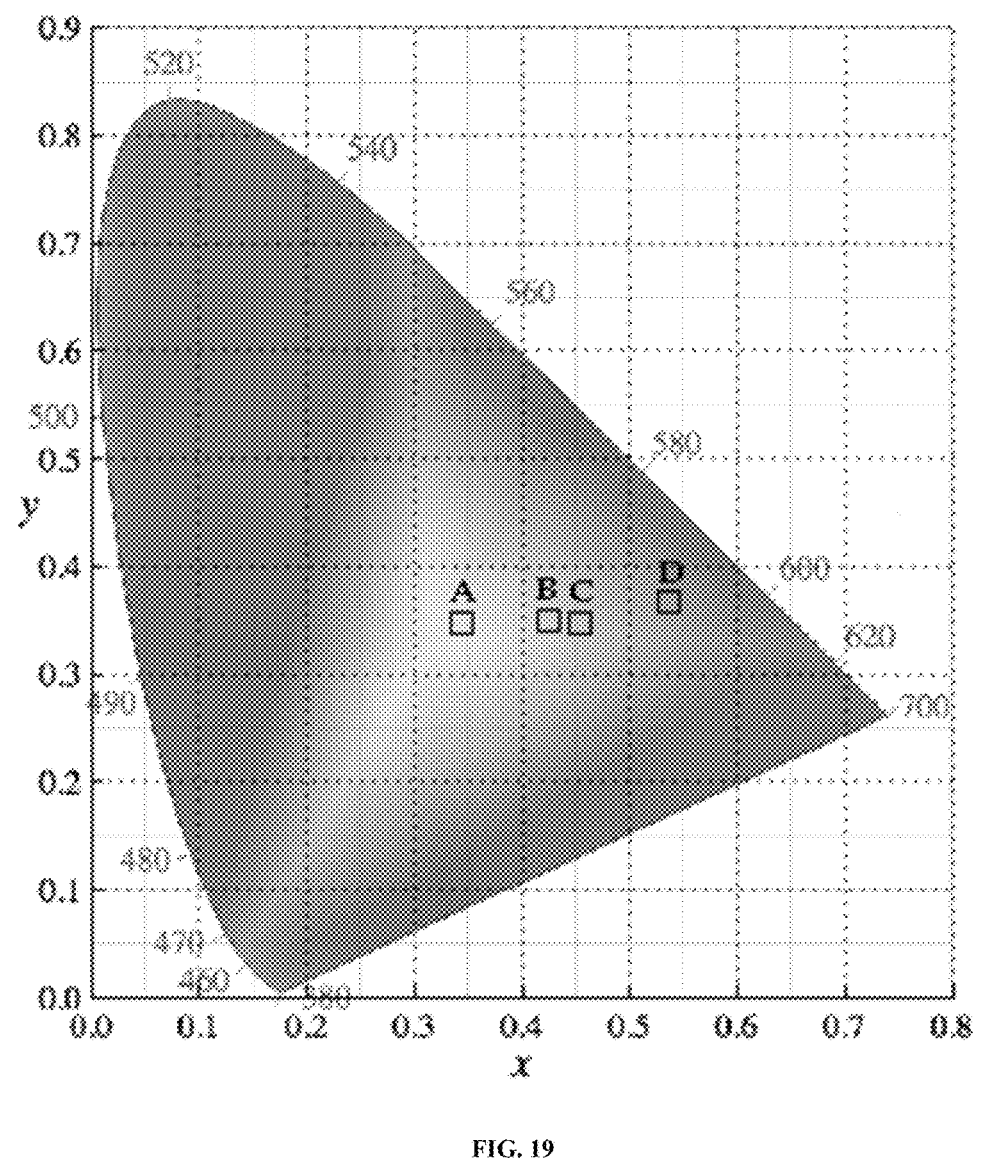

Therefore, color calculations were conducted, based on the 1931 CIE spectral response functions ($\bar{x}, \bar{y}, \bar{z}$) to quantify the visual appearance of the paint recipes. The color calculation methodology is shown in FIG. 18A-C. Briefly, calculated color coordinates represent the visual appearance of a paint recipe viewed under illumination by the xenon Cermax lamp. Clinically BE is observed with an endoscope that incorporates a color CCD camera. The spectral response of modern endoscopic CCD cameras closely matches the ideal $\bar{x}, \bar{y}$ and $\bar{z}$ functions. Therefore, the calculated color coordinates correspond reasonably well to the clinically observed color of BE. We found that the published spectral reflectance of non-dysplastic BE tissue corresponded to an off-white color instead of the widely recognized salmon-red BE color. Furthermore, a color calculation was also performed using the spectral reflectivity of salmon fish fillet. In addition to the spectral reflectance data, the calculations included the relative spectral intensity of a xenon arc light source (Cermax® Xenon, Excelitas Technologies Corp., Fremont, Calif.) that is widely used in modern endoscopes. The results are presented as FIG. 19 and Table 1.

TABLE 1

Calculated color coordinates.

| Light Source | BE | Phantom BE | Salmon | Phantom Healthy |
|---|---|---|---|---|
| Cermax | 0.2969, 0.3286 | 0.4070, 0.3373 | 0.5089, 0.3620 | 0.3769, 0.3378 |

In addition, color calculations based on the reflectance data collected from healthy oral mucosa were consistent with our visual observation of oral tissue. Therefore, the salmon fillet spectra and oral spectra were selected as the representative baseline spectra for BE and healthy esophageal mucosa, respectively. Paint recipes were then optimized to match these guidelines. In addition, we solicited guidance from a panel of experienced Gastroenterologist clinicians to verify paint colors. The final paint recipes are shown in Table 2, all paints used are from Golden Artist Colors, Inc.

TABLE 2

Paint recipes of simulated tissue diffuse reflectance and colors.

| Tissue Type | Paint Ratios (by weight) |
|---|---|
| Healthy esophagus | (Pr:Qm:Hy:Pb:Gg:PgL:TW)(20:10:4:2:1:1:20) |
| Barrett's esophagus | (Qc:Pr:Gg:PgL:PrL)(16:6:4:3:6) |

Pr = Pyrrole red; Qm = Quinacridone magenta; Hy = Hansa yellow; Pb = Phthalo blue; Gg = Green gold; PgL = Permanent green Light; TW = Titanium White; Qc = Quinacridone crimson; PrL = Pyrqrole red Light.

Fluorol Dye-in-Polymer Target Calibration

Figure 20A:
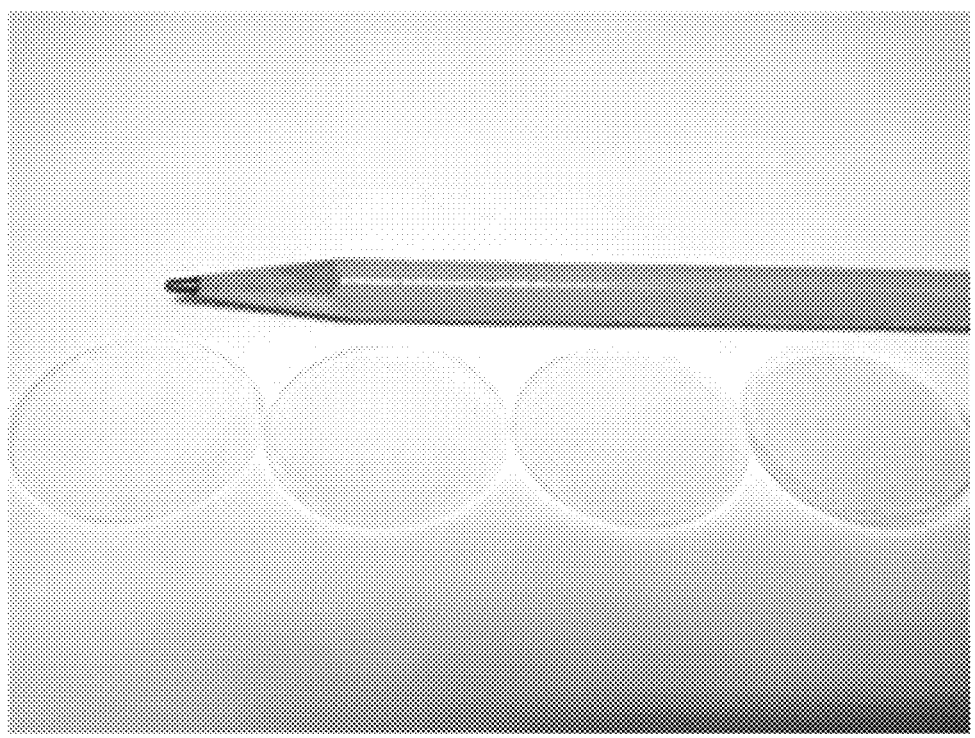
FIG. 20A-20B shows photo representations of dye-in-polymer. ~750 um thin disks (FIG. 20A) and die-cut distinctive star shaped targets (FIG. 20B) in accordance with embodiments.
Figure 20B:
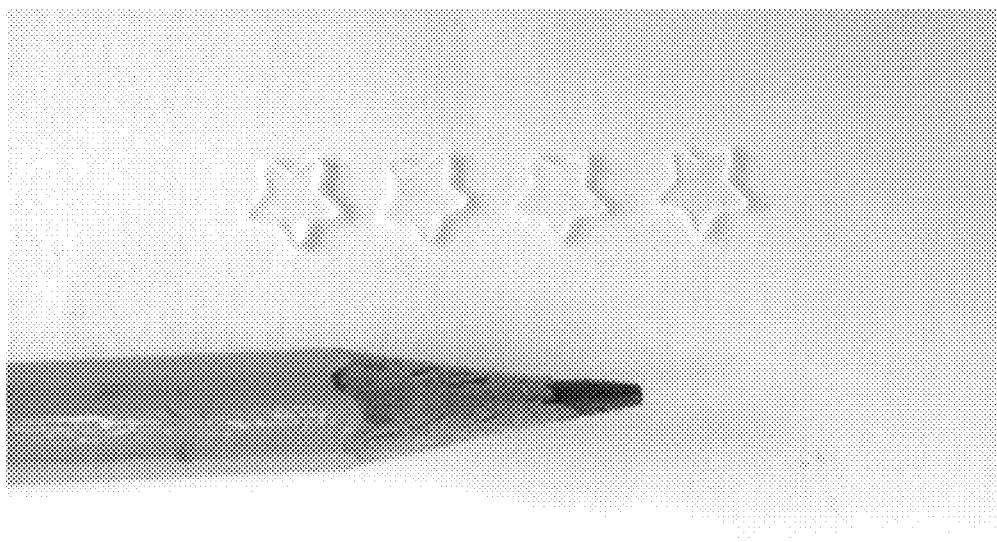
Figure 21A:
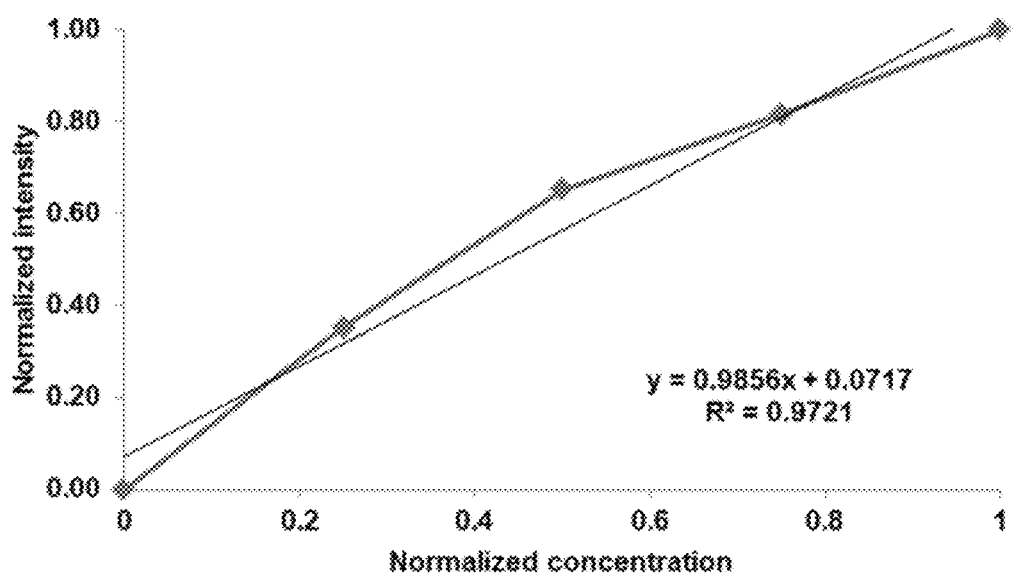
FIG. 21A shows fluorescent target emission intensity recorded with a spectrometer as a function of dye concentration in accordance with embodiments.
Figure 21B:
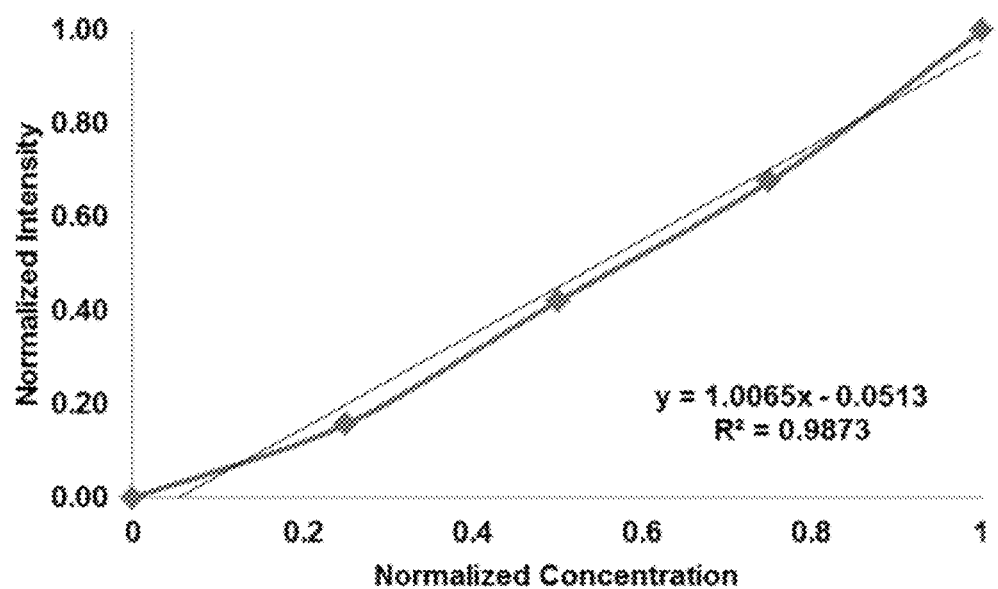
FIG. 21B shows fluorescent target SFE image intensity as a function of dye concentration.

The dye-in-polymer targets produced an emission that peaked at 500 nm when excited by a 444 nm SFE laser. The observed emission spectrum matched the published profile of the fluorescent dye in an acrylic plastic. Targets were saw cut into 750 um thick disks and then die-cut into distinctive star shapes (FIG. 20) with concentrations at 25, 50, 75, and 100 μmol/L. FIG. 21A shows the fluorescence intensity as a function of dye-in-polymer concentration and FIG. 21B presents the SFE fluorescence image analysis of the same dye-in-polymer targets. Both sets of data showed a similar linear behavior.

Phantom Imaging Using the SFE

Figure 22:
FIG. 22 shows SFE images of the same phantom with sphincter open (left) and sphincter closed (right) in accordance with embodiments.
Figure 23A:
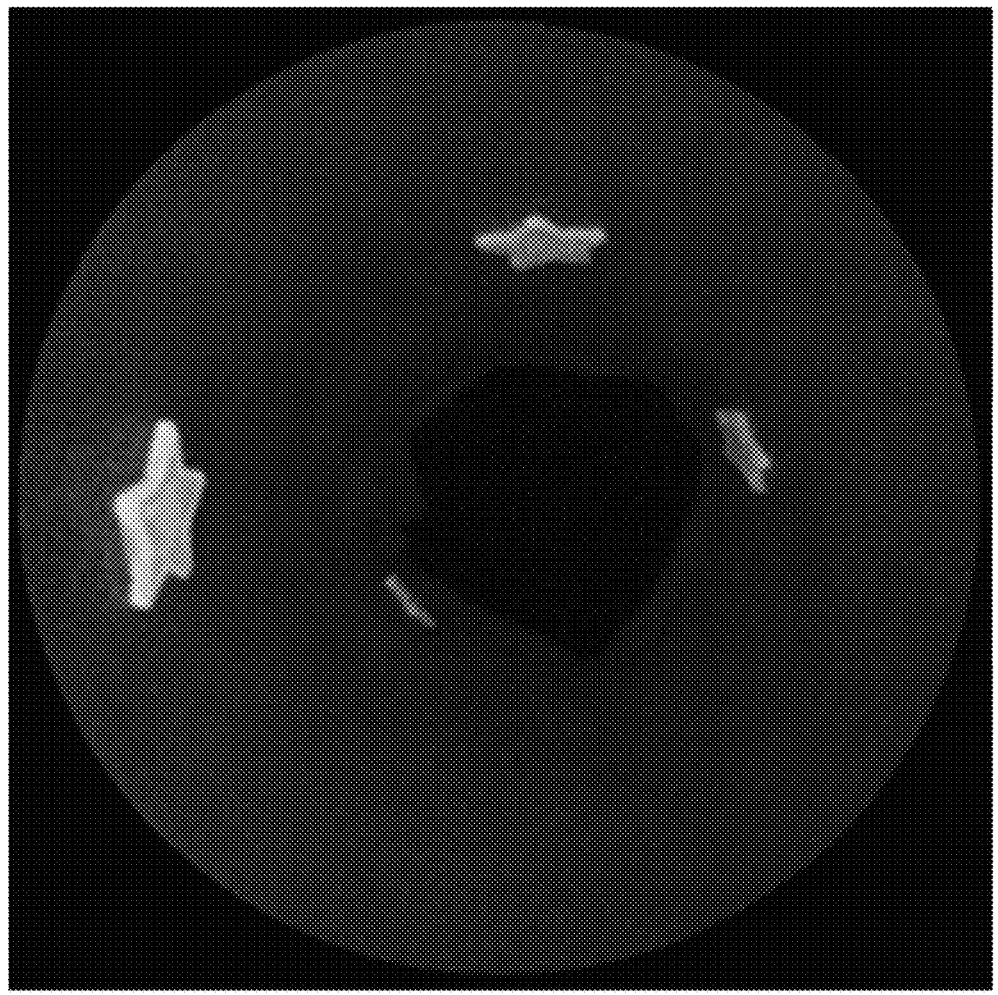
FIG. 23A-23F show application of the SFE distance compensation (DC) algorithm to a phantom esophagus in accordance with embodiments.
Figure 23B:
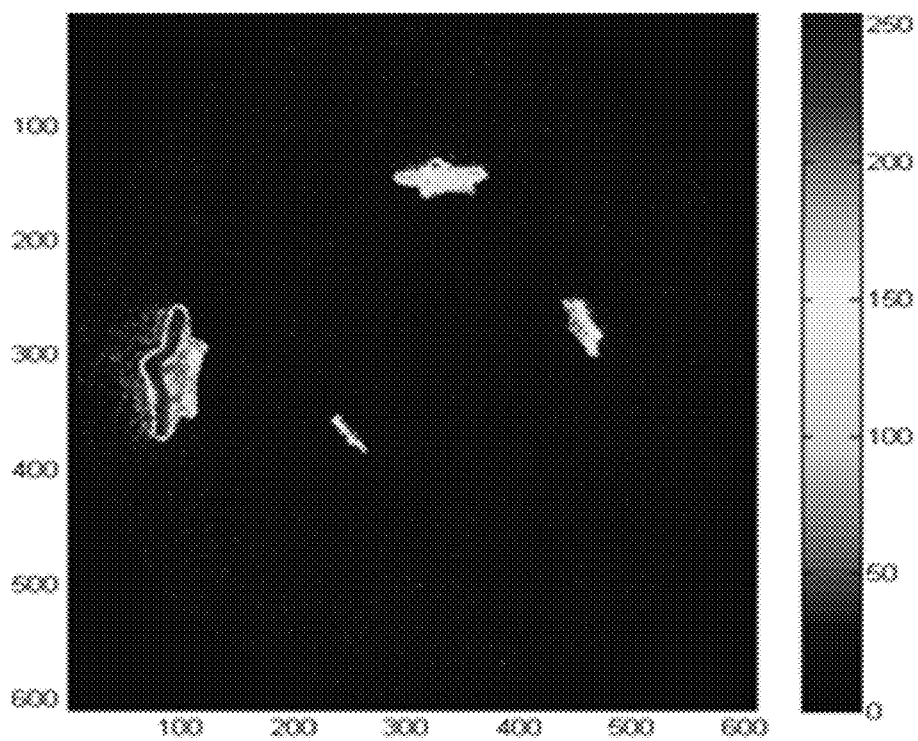
Figure 23C:
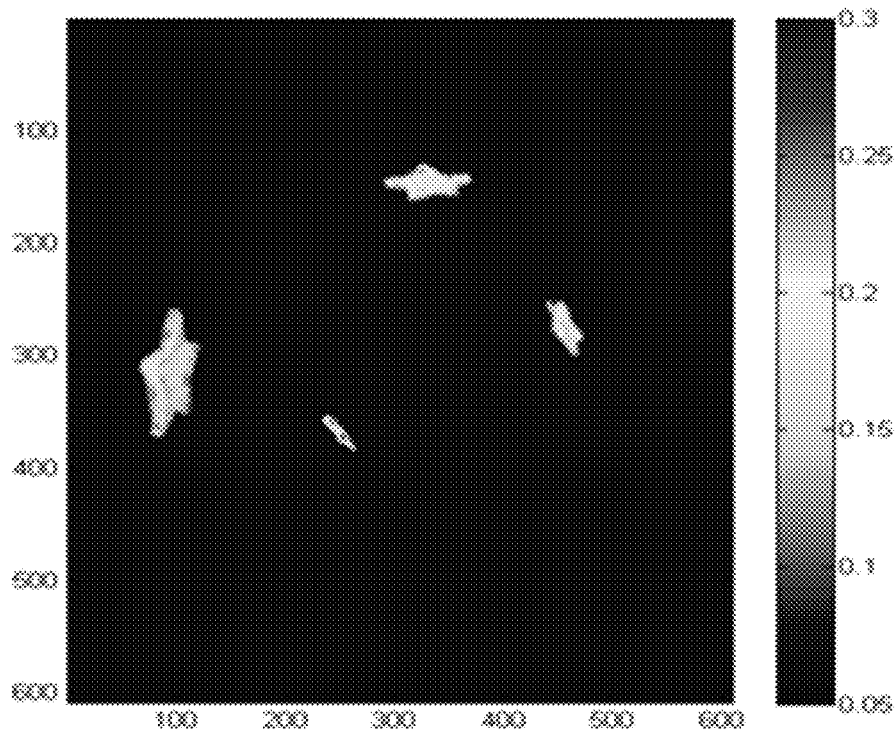
Figure 23D:
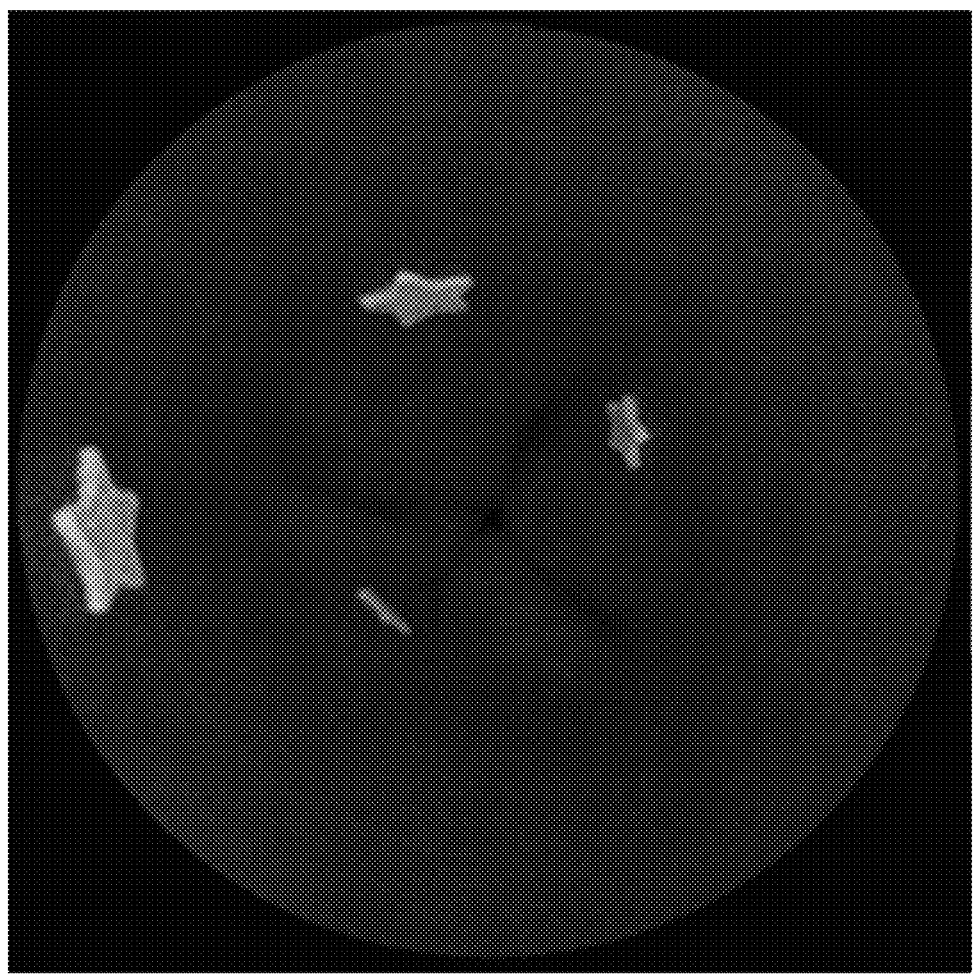
Figure 23E:
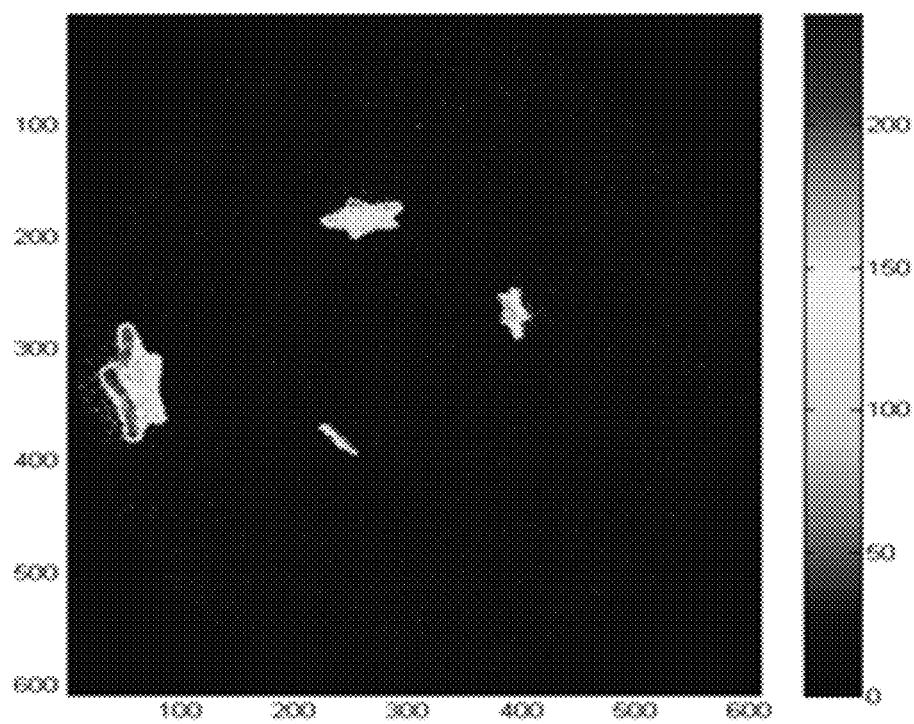
Figure 23F:
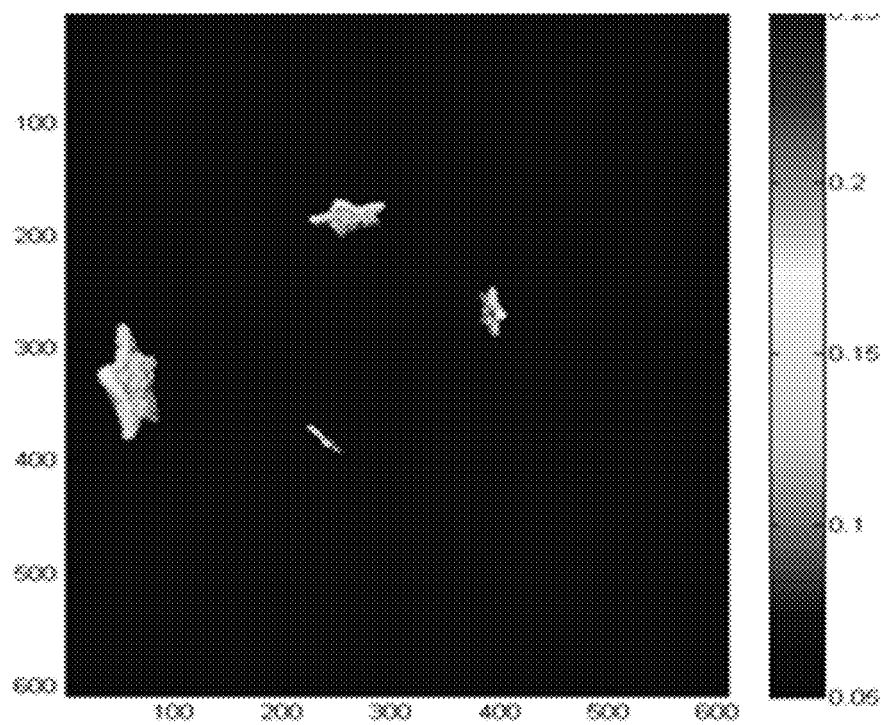

The SFE probe was centered in the esophagus phantom via an in-house designed apparatus, which mimics an endoscope's working channel for transporting the SFE probe into the esophagus. White light and dual mode imaging of the lower esophagus phantom were performed with finger pressure to simulate the opening and closing of the artificial lower esophageal sphincter (FIG. 22 and FIG. 23).

An in vitro SFE image-based fluorescence quantification study was conducted using the realistic esophagus phantom. Quantitative data were obtained by setting fixed gain and offset on the PMTs as well as the digital image formation process through the SFE's computer user interface. Therefore the pixel intensity of the images corresponded to the fluorescence target concentrations and distance from the SFE scope distal end.

The quantification of fluorescence signal was achieved by using an empirically optimized non-linear ratio-metric algorithm, to compensate for the distance differences between the fluorescent targets and the endoscope due to the targets' relative orientation and separations (FIG. 23). FIG. 23A-23C show sphincter open mode. FIG. 23D-23F show sphincter closed mode. FIG. 23A, D show SFE dual-mode (reflectance-fluorescence) images before DC. FIG. 23B, E show intensity maps of the fluorence images from FIG. 23A, D before DC. FIG. 23B, E show intensity maps of the fluorence images from FIG. 23A, D after DC.

This distance compensation algorithm was applied to the simultaneously acquired and thus co-registered fluorescence (F) and reflectance (R) images. A pixel-by-pixel intensity computation using a non-linear ratio of the fluorescence and red channel reflectance ($F/(R^{1.5})$) yielded excellent results.

Before Distance Compensation (DC), the image intensity ratio of two targets with the same dye concentration yielded different values with average errors ~92% for sphincter open mode and ~39% for closed mode. However, the average error after correction was ~8% and ~4% respectively, resulting in a 91% error reduction for sphincter open mode and 89% for closed mode (Table 3). Statistical analysis (paired student-t test, one-tail, $\alpha=0.05$) compared the before and after correction image intensity errors, and result showed the algorithm significantly ($p<0.02$) increased accuracy of target quantification on both modes (Table 3).

TABLE 3

Comparison of targets quantification before and after distance compensation (DC)

a. Sphincter Open Mode

| Location (L) | Expected IR* | before DC* IR | after DC IR | before DC error | after DC error |
|---|---|---|---|---|---|
| L1/L2 | 1.000 | 1.685 | 0.858 | 68.5% | 14.2% |
| L1/L3 | 1.000 | 2.305 | 0.943 | 130.5% | 5.7% |
| L1/L4 | 1.000 | 3.042 | 0.915 | 204.2% | 8.5% |
| L2/L3 | 1.000 | 1.368 | 1.099 | 36.8% | 9.9% |
| L2/L4 | 1.000 | 1.806 | 1.066 | 80.6% | 6.6% |
| L3/L4 | 1.000 | 1.319 | 0.970 | 31.9% | 3.0% | paired student-t test (one-tail) p = 0.013 b. Sphincter Closed Mode

| Location (L) | Expected IR* | before DC IR | after DC IR | before DC error | after DC error |
|---|---|---|---|---|---|
| L1/L2 | 1.000 | 1.227 | 0.998 | 22.7% | 0.2% |
| L1/L3 | 1.000 | 1.510 | 1.087 | 51.0% | 8.7% |
| L1/L4 | 1.000 | 1.764 | 1.035 | 76.4% | 3.5% |
| L2/L3 | 1.000 | 1.231 | 1.089 | 23.1% | 8.9% |
| L2/L4 | 1.000 | 1.438 | 0.998 | 43.8% | 0.2% |
| L3/L4 | 1.000 | 1.169 | 0.952 | 16.9% | 4.8% | paired student t-test (one-tail) p = 0.007

*IR = intensity ratio;
*DC = distance compensation

A custom software user interface was also developed to allow real-time video processing and display of the color-coded map of the distance corrected fluorescence hot-spots with relative quantifications.

A BE phantom was constructed which matched the primary targeted geometric characteristics of the esophagus, measuring 2.5 cm in width and 22 cm in length. This phantom was firm enough to maintain its structure without extra support while also allowing for mechanical manipulation to simulate body motions such as lower esophageal sphincter open and closure.

White light SFE images of the phantom were recorded with a 1.2 mm diameter SFE scope aligned at the center axis of the phantom looking in the direction of the simulated BE tissue. Under white light, the upper portion of the color-matched phantom presented whitish-pink normal esophagus mucosa and in the lower portion a salmon-reddish BE color. The overall appearance of the phantom exhibited similar physical appearance compared to endoscopic images of a human Barrett's esophagus.

The BE diffuse reflectance spectra from the phantom inner surface showed much higher orange-red reflectance compared to the blue-green reflectance. This was similar to the trend observed in the diffuse reflectance spectra feature of Atlantic salmon fillet. As shown in the CIE 1931 color chromaticity diagram (FIG. 19), the referenced Atlantic salmon fillet fell into a distinct red region whereas a previously reported BE color was located at an off-white region. The simulated BE color coordinates were close to the salmon-red color region. At the same time, the simulated normal esophagus color was white-pinkish. We think that the off-white color resulting from the BE reflectance spectra published in was caused by pressure on the tissue by the probe contact. Recently, the effect of probe contact pressure on in vivo optical spectroscopy of soft liver tissue, oral mucosa, and mouse thigh muscle has been studied and distortions of tissue spectra reflectance have been discussed.

In clinical video endoscopy, the perceived tissue colors, as well as disease-healthy tissue color contrast could serve as important diagnostic indicators. Therefore, phantoms designed with realistic tissue colors provide platforms to develop practical in vivo color image processing algorithms. Recently real-time implementation of color enhancement algorithms for endoscopy have been reported that highlight subtle differences between cancerous and healthy tissues, and endoscopic imaging techniques using tissue color enhancement showed value assisting the detection, diagnosis and treatment of gastrointestinal diseases. When visualizing fluorescent targets, the realistic tissue color is important for the selection of pseudo color representations of the reflectance image to enhance contrast. Therefore, phantoms designed with realistic tissue colors could contribute to augmenting molecular imaging modalities for early cancer detection and diagnosis.

In dual mode SFE imaging, concurrent red reflectance image and fluorescent targets were readily visible (FIG. 23). The real-time SFE concurrent fluorescence and reflectance view provides a geometric alignment that is lacking in systems with non-concurrent fluorescence/reflectance image capture. Moreover, Enhanced Spectral Imaging (ESI, nearly equivalent to narrow band imaging) is an enabled feature in the SFE. When wavelength specific spectral imaging is needed, for example in BE ablation surveillance or observation of tissue vascular network, the ESI can be easily performed. One future modification of the phantom would be the addition of a simulated vascular network for the study of narrow band imaging in BE, or other common esophageal diseases such as esophageal varices.

The distance compensation algorithm was applied to both lower sphincter open and closed modes using a 1.2 mm SFE endoscope. The results showed distance normalization of the perceived intensities (FIG. 23). This compensation significantly improved the accuracy of target fluorescence intensity quantification. According to the quantitative analysis in Table 2, after applying the distance compensation algorithm, the targets' intensity error for sphincter open and closed modes has been reduced by 91.3% and 88.8%, respectively. The red reflected light was selected because the red wavelengths are less absorbed by hemoglobin and therefore less influenced by changes in vascularity among diseased tissues. In addition, red reflected light is more uniformly scattered by the tissue morphology. Overall, red light provides a more uniform reflectance image of the target geometry than blue/green colors. The robustness of this algorithm was also tested for scenarios when the endoscope is not aligned with the esophagus center axis, and results yielded consistent normalized image intensity (data not included).

The present esophagus phantom does not include autofluorescence (AF). Collagen is believed to be primarily responsible for esophageal AF when the wavelength of the excitation light is in the 350 to 370 nm range. However, when the excitation wavelength is longer than 440 nm, results from extensive searching of published collagen excitation-emission matrix (EEM) data indicate that the collagen AF decreases by a factor of 3× to 5× compared to the maximum at 350-370 nm excitation. Since the present phantom is intended for molecular imaging studies at wavelengths longer than 440 nm, it was assumed that AF would not be a significant confounding factor. AF could be simulated if necessary by adding collagen material to the paint formulation.

In the current study, the net esophagus diffuse reflection, including surface and shallow subsurface light scattering was simulated. Since the primary interest of this phantom is for simulation of topically applied surface fluorescent labels, deep tissue light optical penetration and scattering were not included. A biomarker that is located on the cell surface is epithelial growth factor receptor (EGFR). However, this EGFR biomarker is overexpressed in only 35% of high-grade dysplasia (HGD) specimens in Barrett's esophagus. HGD has a high probability of advancing to esophageal adenocarcinoma which in turn has a low survival rate (ten to fifteen percent). Therefore, molecular imaging devices may utilize more than one dye label to improve sensitivity and specificity. The phantom model developed in this study can be adapted to include additional fluorescent dye species representing labeling of more than one biomarker. The coincident emission signature from multiple dyes is expected to provide a more accurate disease state diagnosis than a single wavelength marker. This coincident emission signature from multi-spectral molecular probes could be obtained concurrently using the multi-channel photodetection feature of the scanning fiber endoscope. If the administration of multiple probes is restricted to time sequential applications, image alignment can be realized with an image stitching algorithm.

Embedding CT/MRI fiducial markers, to allow for multi-modality imaging strategies for disease diagnostic and treatment, is another future embodiment of the phantom. For example, the co-registration of optical images with CT/MRI volumetric imaging could enable new optical-to-CT/MRI combined data for pre/post tumor resection surgery comparisons. Magnetic Microspheres (Bangs Laboratories, Inc) are stable and dispersible in the urethane resins or acrylic paints in our phantom, and can be made to contain both magnetic and fluorescent material. Properly functionalized spheres could be dispersed in urethane or acrylic paint resins and included in the phantom fabrication process to allow this bi-modal imaging.

In conclusion, a color-matched and fluorescence labeled esophagus phantom for clinical wide-field endoscopy applications was fabricated. The 3D structure of the resultant phantom was semi-rigid with enough flexibility to mimic body movements. Also, through a color matching methodology, the perceived phantom tissue color and diffuse spectral reflectance were reconciled to simulate the clinically observed characteristics of typical human healthy and Barrett's esophagus. The dye-in-polymer method was used to quantitatively simulate surface fluorescence labels. This phantom provides opportunities for assisting in the validation of novel endoscopic imaging systems, such as the wide-field multi-spectral fluorescence scanning fiber endoscope, as well as image-based fluorescence quantification, and other image processing algorithm developments.

Example 4

Application of Detecting Fluorescence Hot-Spots Using Mosaic Maps Generated from Multimodal Endoscope Imaging This example is related to the above section titled "Detecting fluorescence hot-spots using mosaic maps generated from multimodal endoscope imaging."

In Vitro Barrett's Esophagus Phantom Imaging

A color-matched and fluorescence-labeled Barrett's esophagus phantom was developed in our lab for the evaluation of the stitching software. This phantom was fabricated to match the structural dimension of a human esophagus. A paintable elastomeric material was selected and used for the phantom's three-dimensional shape so that it can mimic essential body movements. At the same time, realistic visual appearance and diffuse spectral reflectance properties of the tissue were simulated by a color matching methodology. A photostable dye-in-polymer technology was applied to represent biomarker probed "hot-spot" locations. The resultant phantom has been proven to be stable, repeatable, economical to fabricate, and has been successfully used in other applications such as image-based biomarker quantification.

In the present study, a 1.2 mm SFE was centered in the esophagus phantom via an in-house designed apparatus, which mimics an endoscope's working channel for transporting the endoscope into the esophagus and maintaining its position along the centerline.

Dual-Mode SFE Imaging

Figure 24:
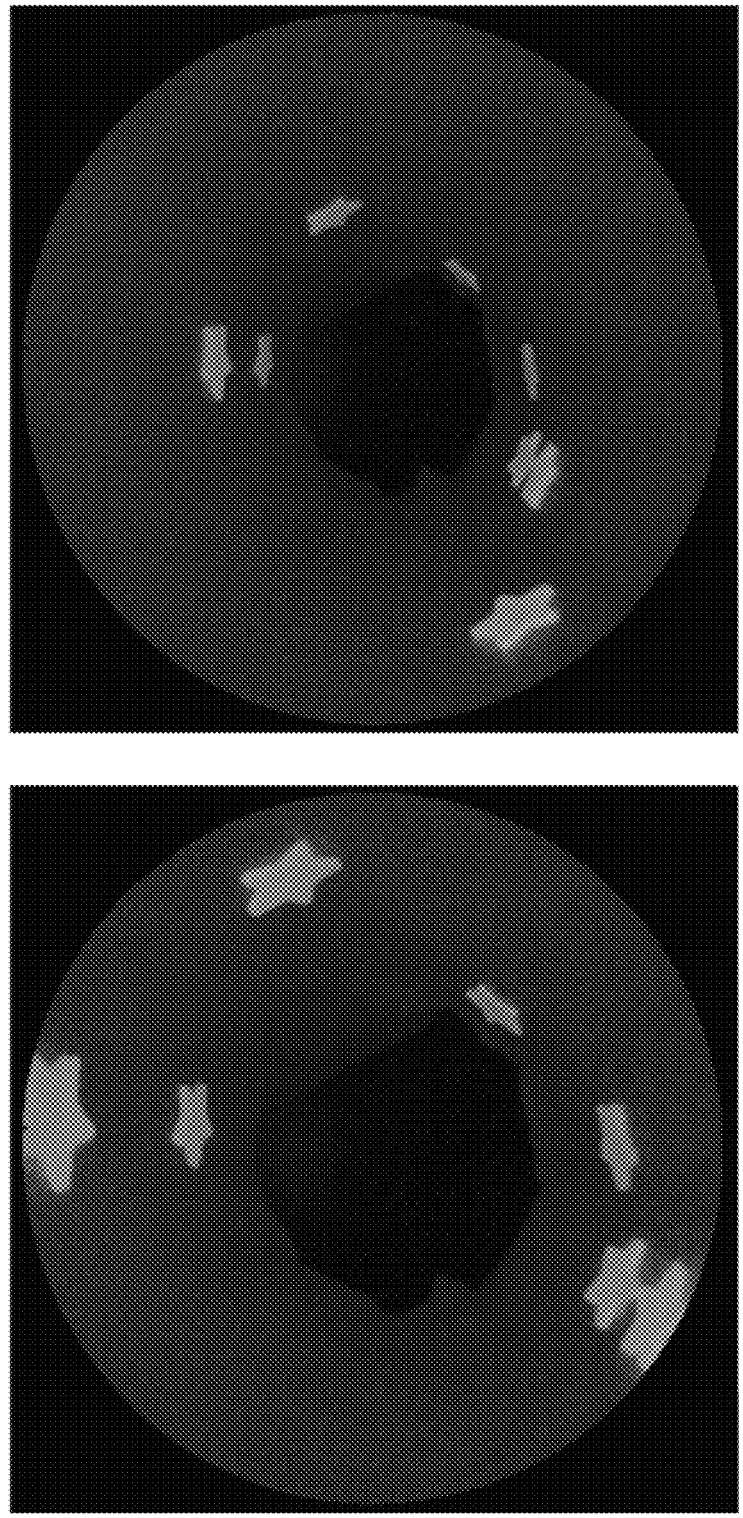
FIG. 24 shows SFE-acquired images of the custom BE phantom in the upper esophagus (top image) and after being inserted several additional centimeters (bottom image) in accordance with embodiments.

The Barrett's esophagus (BE) phantom reflectance-fluorescence images were acquired from the SFE scan. Images were taken which simultaneously captured blue and red reflectance as well as green fluorescence. To represent the high-grade dysplasia and early cancer hot-spots, a total of 8 fluorescent hot-spots were distributed and attached to the lower esophagus area. Within these hot-spots, half had the same high concentration whereas the other half had the same low concentration. Two frames acquired during the same scan were shown in FIG. 24 as examples of the SFE reflectance-fluorescence imaging. The purplish background is a combination of blue and red reflectance, while the green hot-spots were acquired from the fluorescence channel.

Mosaic of the Lower Esophagus

Figure 25:
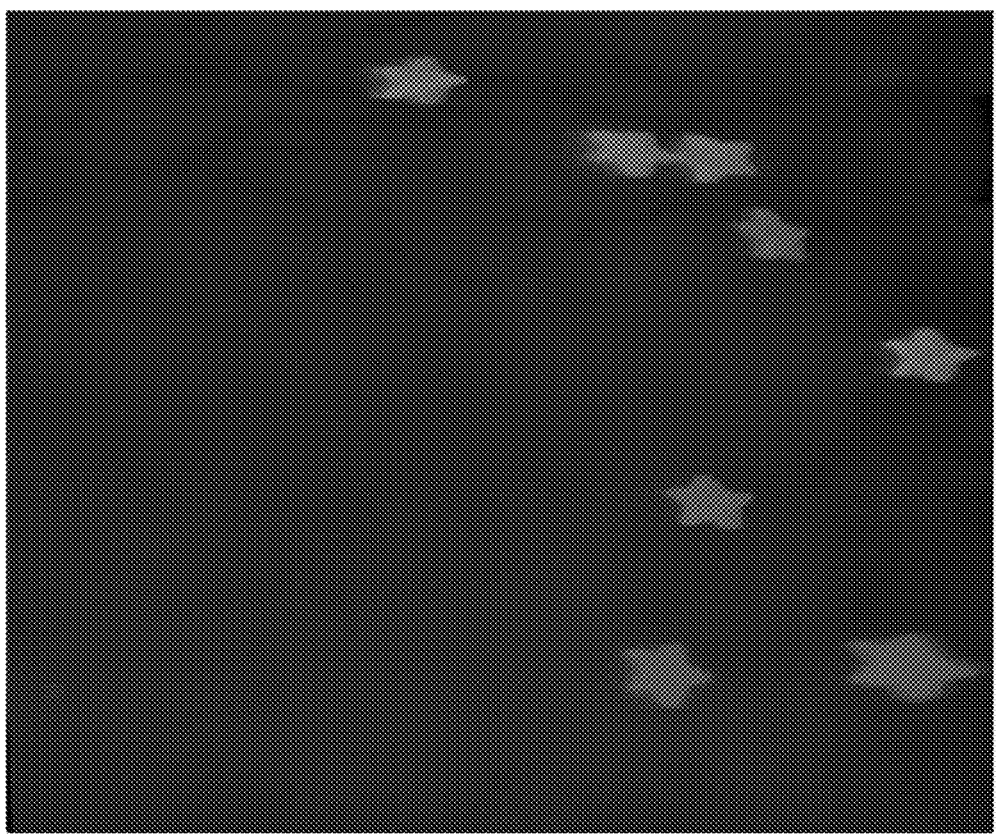
FIG. 25 shows the result of a mosiac map generated from the scan in accordance with embodiments.

A mosaic of the BE phantom endoscopy was generated from the aforementioned stitching software. FIG. 25 shows the resultant unwrapped dual-mode image of the entire lower esophagus where Barrett's esophagus and fluorescent hot-spots were located. The result generated from the scan (~40 frames combined) shows a combined reflectance and fluorescent image of the scanned area (FIG. 25). From the mosaic map, the painted BE area with sparse vessels appears well aligned and the distinctively shaped fluorescent hotspots are clearly visible. Overall, a panoramic view of the BE phantom was generated with a root-mean-square (RMS) error of 1.04.

Figure 26A:
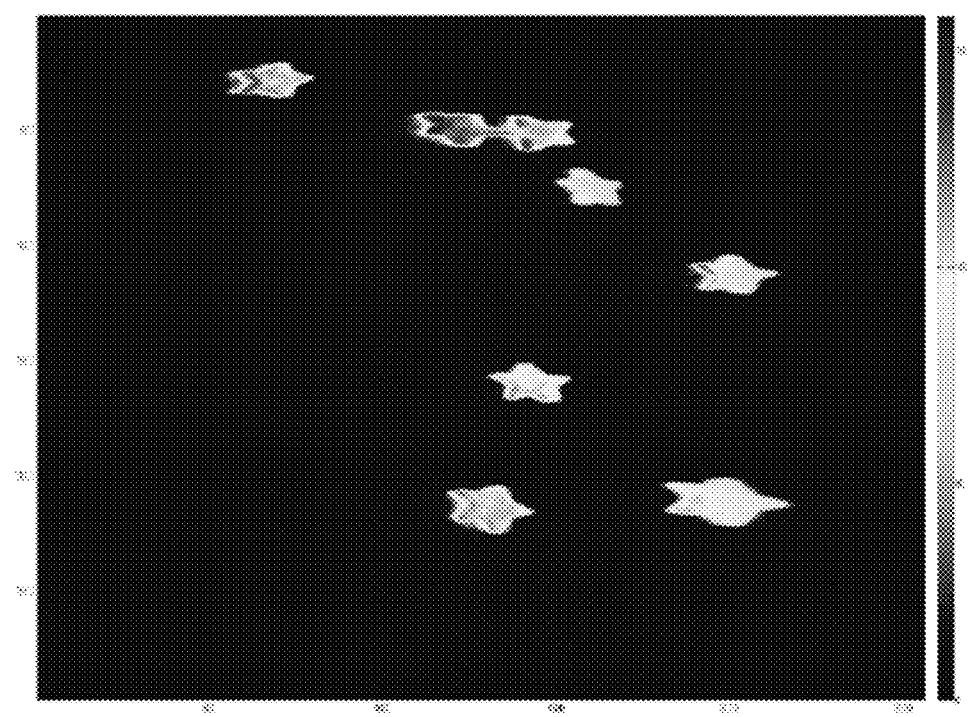
FIG. 26A shows a colormap representation of the fluorescence image in the resultant mosaic in the case where DC is not applied. The target intensities do not match their dye-in-polymer concentrations in accordance with embodiments.
Figure 26B:
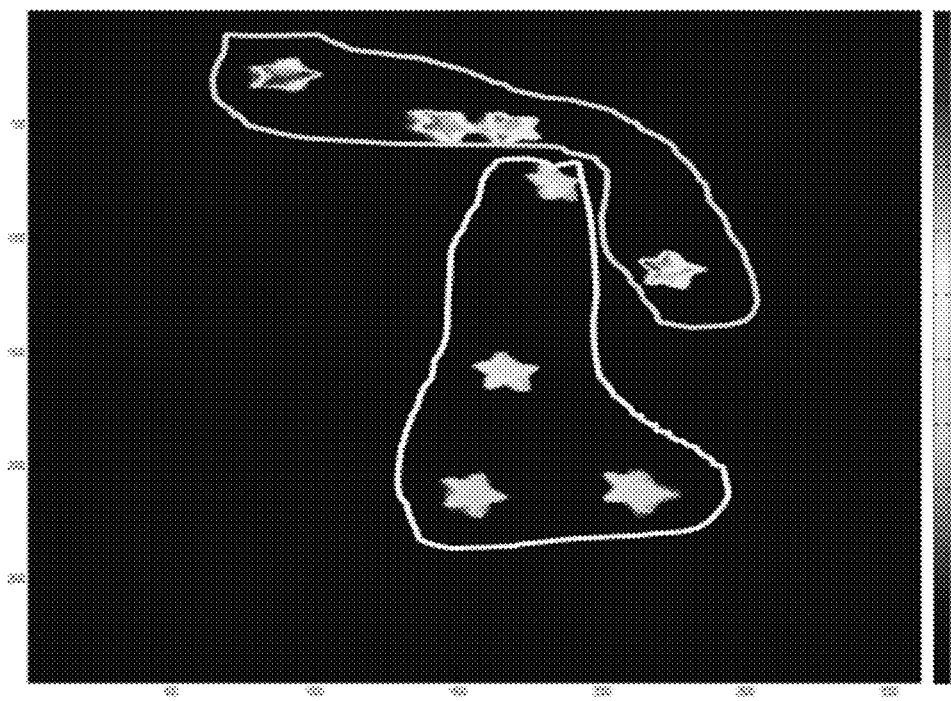
FIG. 26B shows a colormap representation of the fluorescence image in the resultant mosaic in the case where DC is applied. The target intensities match their dye-in-polymer concentrations in accordance with embodiments.

The effect of applying the fluorescence quantification algorithm is shown below (FIG. 26A-26B), comparing the stitched mosaic with the distance compensation quantification algorithm versus the mosaic without this distance correction. In the intensity maps of the fluorescence mosaics, hot-spot intensities from the distance compensation (DC) applied mosaic showed a clear grouping of intensities between targets of similar dye-in-polymer concentration. Whereas the non-DC applied result showed a random pattern of hot-spots intensities that did not necessarily correlate to the dye-in-polymer concentration groupings. Thus, in the case where DC is not applied, target intensities do not match their dye-in-polymer concentrations (FIG. 26A), whereas in the case where DC is applied, target intensities match their dye-in-polymer concentrations (FIG. 26B).

Mosaic on Low Signal-to-Noise Fluorescence

The performance of the mosaicking software was also tested on sets of reflectance-fluorescence images with low signal-to-noise (SNR). Using the same algorithm as previously discussed, registration was calculated from co-acquired high SNR reflectance images, and then applied to both reflectance and low SNR fluorescence images.

Figure 27:
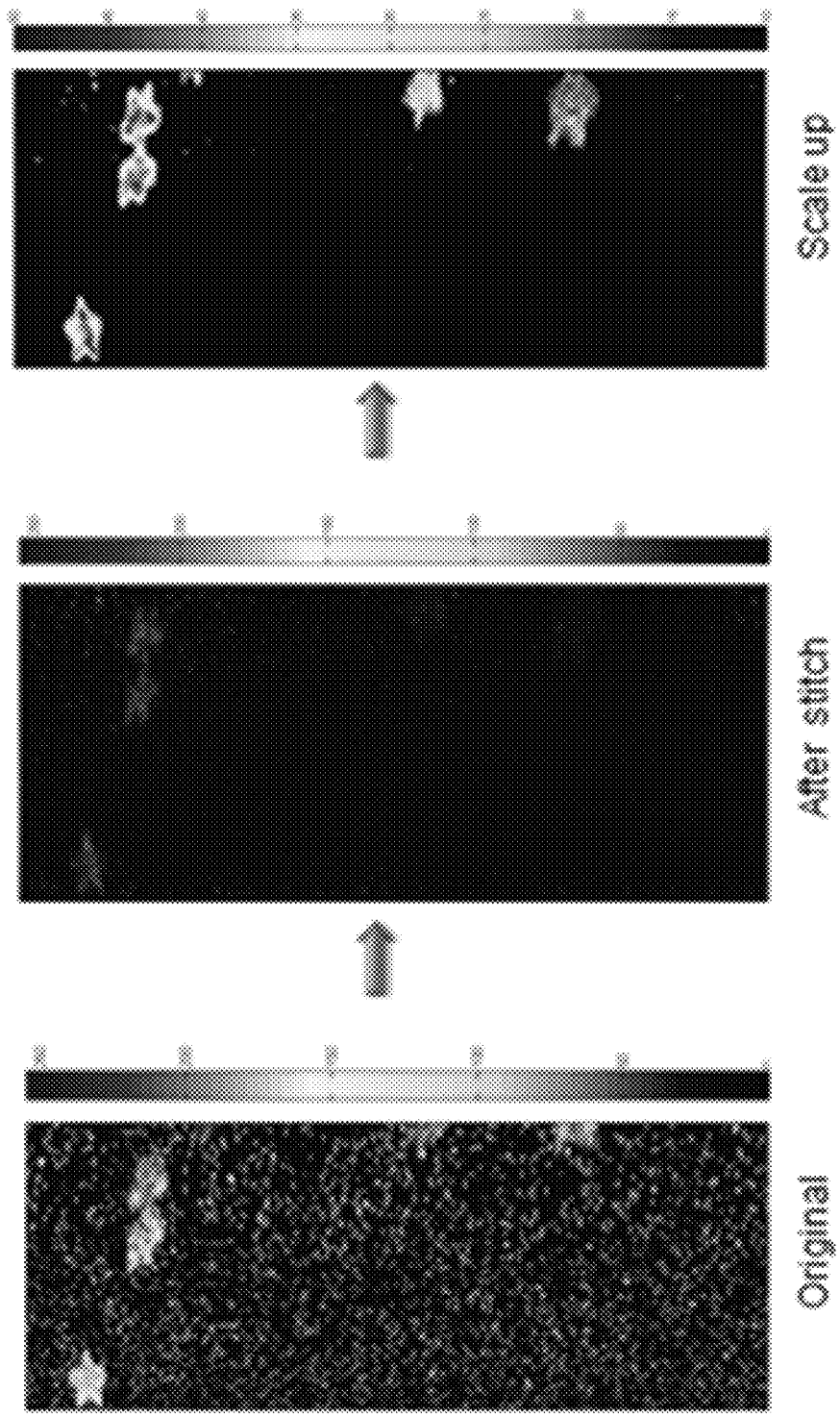
FIG. 27 shows that electronic noise in the original fluorescence images (left) was decreased after stitching (middle). Targets intensities were then scaled up to a hot-spots intensity map (right) in accordance with embodiments.

Images from the same BE phantom described above were acquired with electronic noise simulated in the fluorescence channel (See FIG. 27 left). Results comparing before and after stitching 30 successive frames of the same hot-spots area (FIG. 27 middle) showed that the stitching process reduced a great amount of background noise, and the hot-spots were distinctively visible after scaled up targets intensities (FIG. 27 right). The root-mean-square (RMS) error (1.02) was not affected by the noise in the fluorescence channel as the algorithm only looked into the reflectance channels to solve for the registration.

Figure 28:
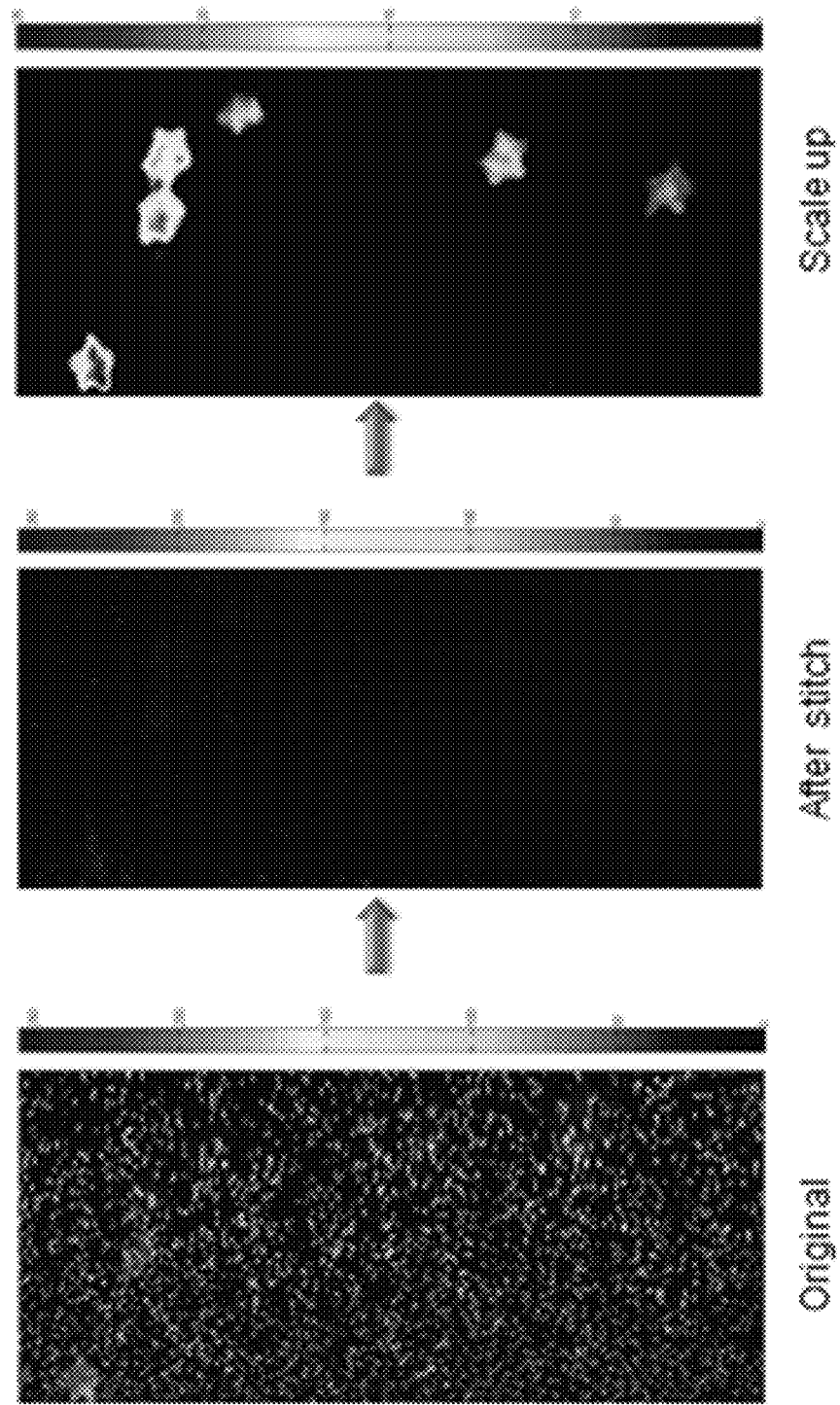
FIG. 28 shows that electronic noise in original fluorescence images of low-intensity fluorescent targets (left) was decreased after stitching (middle). Targets intensities were then scaled up to a hot-spots intensity map (right) in accordance with embodiments.

Furthermore, in order to evaluate the ability of the software to enhance signals with both a high noise level and low signal intensity, the BE phantom images were also acquired which not only had background electronic noise in the fluorescence channel but also had low-intensity fluorescent targets (See FIG. 28 left). Results in FIG. 28 compared the same region of interest before and after applying the stitching algorithm. In the original fluorescence image intensity map shown in FIG. 28, the targets were barely distinguishable from the noise. However, the stitching process averaged out the noise through successive frame overlap and averaging (FIG. 28 middle, right). It improved not only the ability for humans to distinguish these targets from the background but it also increases the applicability of various computer-aided analysis and algorithms (such as using the Weber ratio for target detection). This is despite the fact that the fluorescent channel itself did not have enough features to be successfully stitched.

FIG. 28 shows that electronic noise in the original fluorescence image (left) was decreased after stitching (middle), however, targets intensities were too low to be easily visible. After scaled up to a hot-spots intensity map (right), targets intensities were more visible.

The 1.2 mm SFE with flexible scope demonstrated high resolution, wide field of view, concurrent reflectance and fluorescence imaging of the Barrett's esophagus phantom. In the present study, the standard red and blue SFE detection channels were used for reflectance images whereas the green channel was used for the fluorescence detection. However, additional lasers and detection channels can be added, to perform concurrent RGB white light reflectance and multi-spectral fluorescence imaging. Gathering both signals at the same time allows for the use of all channels of information in the analysis without having to register the spectra against each other, which can be challenging due to variations in the scene or in the scanning procedure (speed of movement etc.). Ultimately, it can lead to improved diagnostic accuracy.

The resultant mosaic encompassed a much wider view of the scene than that captured from a single endoscopic frame. The fluorescence hot-spots were visibly distinct from the background (FIG. 25), with quantitative intensities correctly associated with the targets' concentrations (FIG. 26B). The reflectance images were well aligned and the RMS error of 1.04 was in agreement with a good registration score.

The stitching software utilized a direct (pixel-based) alignment method, instead of feature based methods, to find the motion between two frames. This is because consistent features can be hard to find in the reflectance channel of esophagus, comparing to other parts of the body, such as in the bladder or colon. Meanwhile, using the concurrent reflectance images to solve for the motion is preferable to using the fluorescence channel, as that channel is prone to a low signal-to-noise ratio which significantly increases the error of the stitching. Additionally, by using a multi-resolution, incremental approach to calculating the transformations, the processing time was significantly reduced without sacrificing registration accuracy.

More importantly, this example shows that the stitching algorithm was able to significantly enhance the fluorescent SNR, and provide targets in the stitched map with quantified fluorescence signals by effectively performing an averaging filter over the video without requiring the camera to remain stationary. The recorded mosaic can also be used for more extended review by the clinician without signal decreasing due to fluorescence photobleaching. And this mosaic map can be built into as part of the SFE's graphic user interface and possibly be used for future computer-aided diagnosis tools.

Example 5

Solutions for Mitigating Fluorescence Spectral Overlap in Wide-Field Endoscopic Imaging This example is related to the above section titled "Mitigating Fluorescence Spectral Overlap in Wide-field Endoscopic Imaging."

Characterization of Fluorescence Dye Emission Cross-Talk

Figure 29:
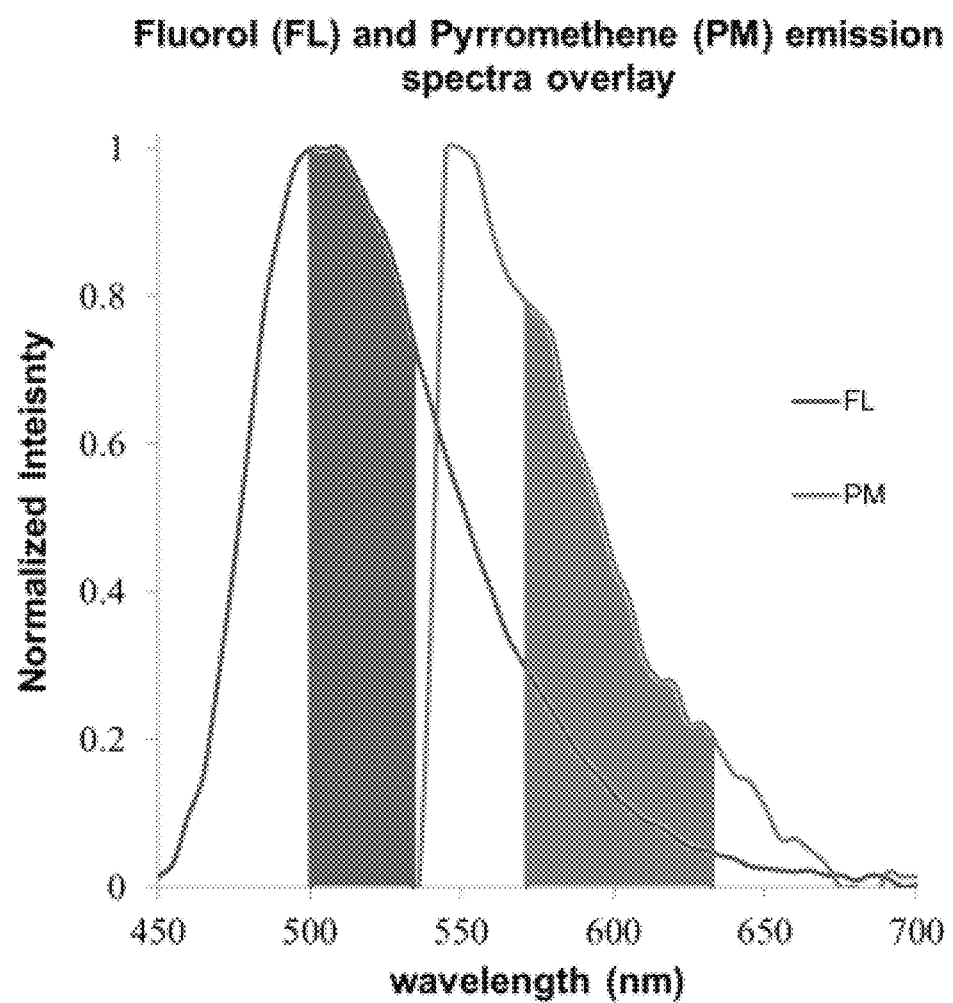
FIG. 29 shows FL and PM dye-in-polymer fluorescence emission spectra superimposed over the SFE green and red channel detection ranges in accordance with embodiments.

The FL dye-in-polymer targets produced an emission that peaked at 500 nm under 442 nm laser excitation and the PM dye-in-polymer targets produced an emission that peaked at 550 nm under 532 nm laser excitation (FIG. 29). The observed emission spectra closely matched the published fluorescent dye profile. FIG. 29 shows that the emission spectra of the two dyes exhibits cross-talk, specifically, the long wavelength tail portion of the FL dye emission spectrum overlaps the PM dye emission from (~540 nm)-(~700 nm). The band pass ranges of the SFE green and red channels, which are situated at 500-540 nm and 570-640 nm respectively, are also plotted and are highlighted as solid green and red colors in FIG. 29.

The FL targets were excited with a 442 nm laser and produced an emission that peaked at 500 nm (FIG. 29). The PM targets were excited with a 532 nm laser and produced an emission that peaked at 550 nm (FIG. 29). The band pass ranges of the SFE green (500-540 nm) and red (570-640 nm)

channels are also plotted and highlighted as solid bands (FIG. 29). The emission spectra of the two dyes exhibit cross-talk. Specifically, the long wavelength tail portion of the FL dye emission spectrum overlaps the PM dye emission from (~540 nm)-(~700 nm).

SFE Imaging Solutions for Dye Cross-Talk

Merging Two-Dye Fluorescence Hot-Spots Using Image Stitching

Figure 30:
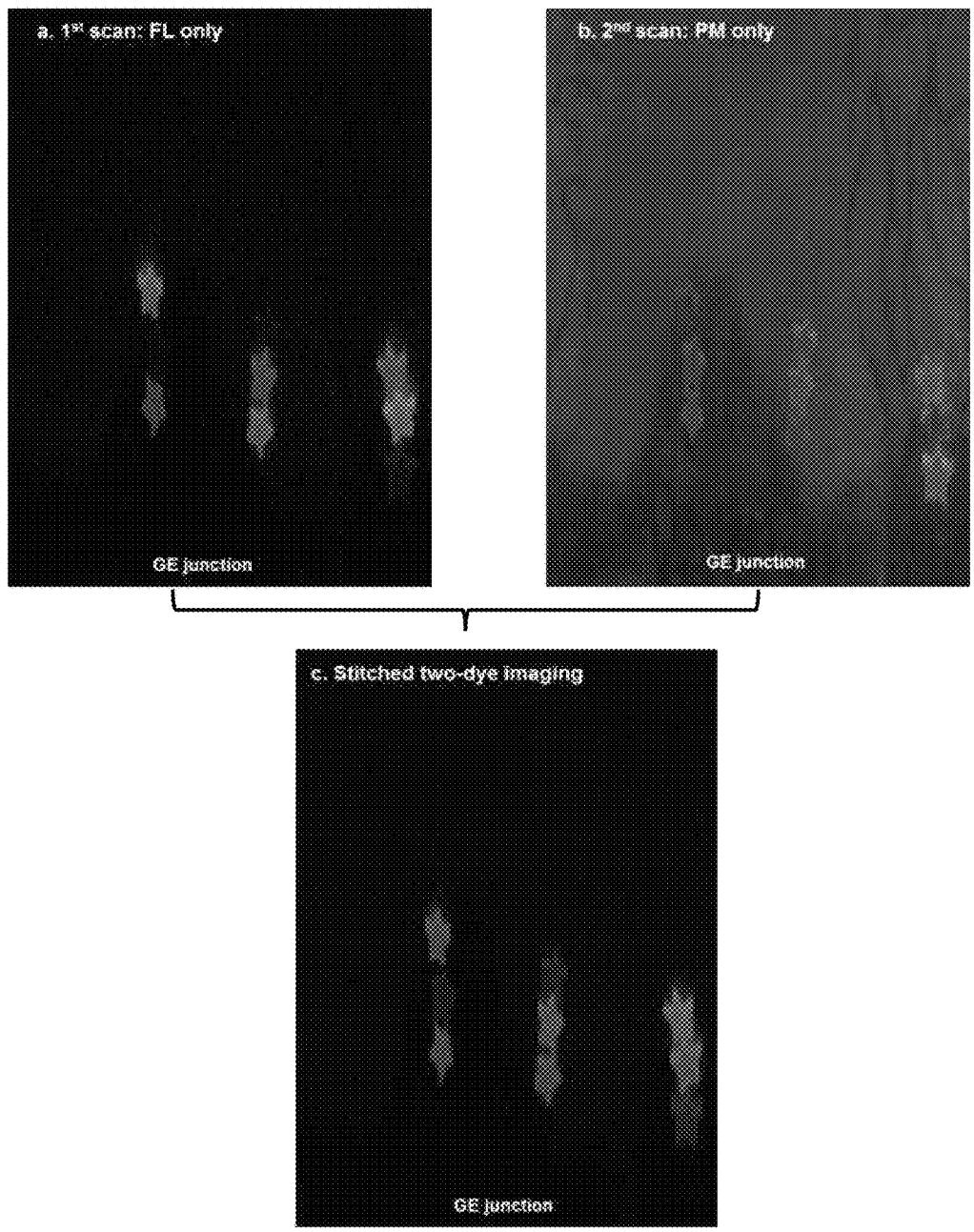
FIG. 30 shows a stitched and unwrapped 2D map for FL imaging in accordance with embodiments.

Two sets of SFE dual-mode reflectance-fluorescence images were collected as described in FIG. 12. The first image consists of the FL dye target emission, the second consists of the PM dye emission. All the other experimental factors (laser power, gain and offset, etc.) were held constant during the image acquisition. The stitched and unwrapped 2D map for the FL imaging (FIG. 30, upper left) comprised the blue reflectance images shown as the background with the FL green fluorescent hot-spots. Meanwhile, the 2D stitched map for the PM imaging (FIG. 30, upper right) comprised the green reflectance image of the same background scene as in FIG. 30 (upper left), with the PM red fluorescent hot-spots. The red fluorescence appeared as an orange color in FIG. 30 (upper right). This was due to the overlap of the red PM targets' color with the green background reflectance.

The two separate stitched 2D maps were then combined and spatially registered using shared information from the blue and green reflectance channels. In the combined stitched map shown in FIG. 30 (bottom), only the FL fluorescence is shown in the green display channel and the PM fluorescence in the red display channel. The FL-PM two-dye targets are shown as orange. No dye cross-talk was observed.

Concurrent Multispectral Fluorescence Imaging

Experiments were conducted to verify that the 442 nm laser exclusively excites FL emission while the 532 nm laser exclusively excites PM emission. Therefore, cross-talk between the green and red SFE detection channels arises only from the overlapping fluorescence from the two dyes as illustrated in FIG. 29. For the micromolar dye concentrations used in this study, dye-to-dye energy transfer was not observed.

Figure 31A:
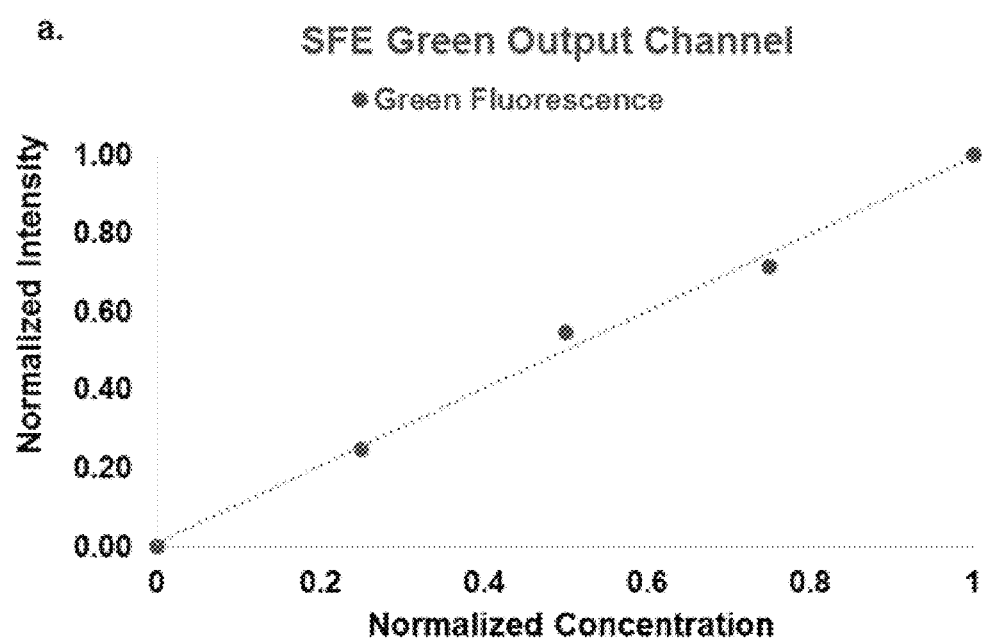
FIG. 31A shows detected fluorescence signals from SFE green detection channel images plotted against the fluorescence dye-in-polymer concentrations in accordance with embodiments.
Figure 31B:
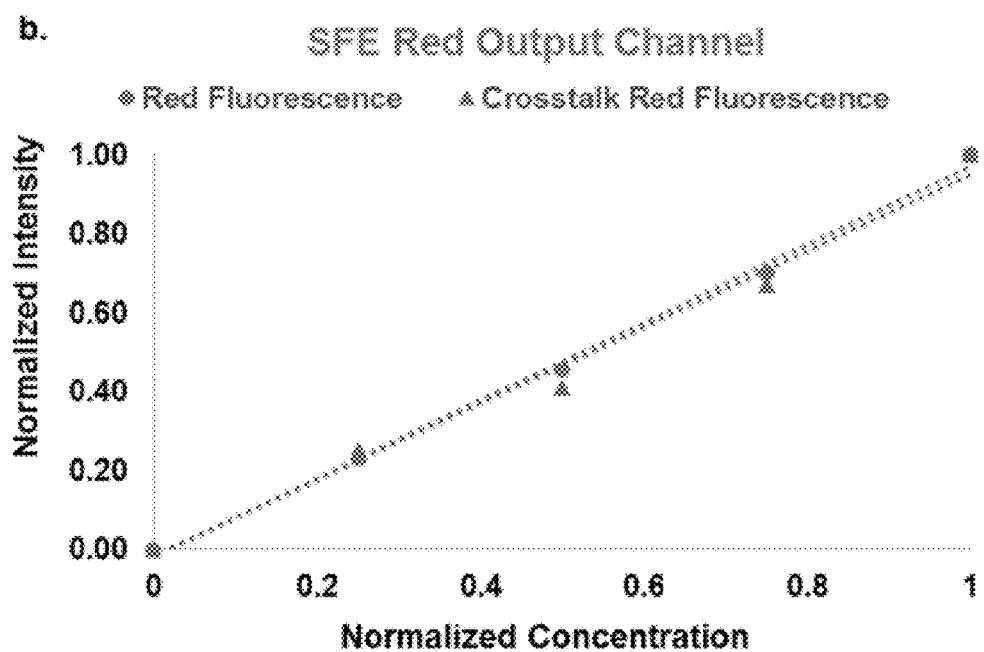
FIG. 31B shows detected fluorescence signals from SFE red detection channel images plotted against the fluorescence dye-in-polymer concentrations in accordance with embodiments.

A linearity test of the fluorescence output channels was conducted and the results are plotted in FIG. 31A-31B. The response of the SFE green and red detection channels were measured by imaging FL and PM targets containing precise dye concentrations. Linear relationships were measured for the dye-in-polymer concentrations as shown in FIG. 31A-31B. The data shows that a linear relationship exists for both channels.

Figure 32:
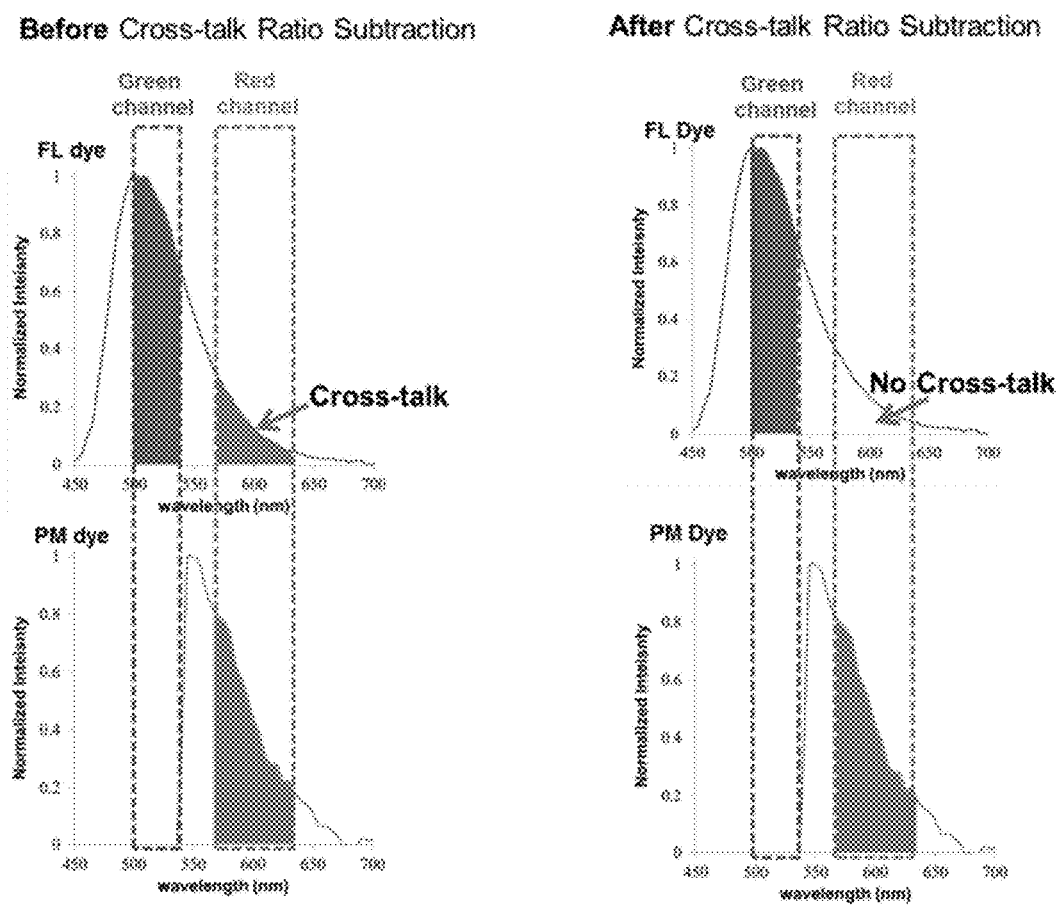
FIG. 32 shows a graphic illustration of concurrent multispectral imaging before (left) and after (right) applying the Cross-talk Ratio Subtraction (CRS) method in accordance with embodiments.

By applying the Cross-talk Ratio Subtraction (CRS) algorithm presented in Eq. 1 and 2, the FL dye Cross-talk Ratio (CR) was calculated and concurrent SFE dual-fluorescence imaging with corrected PM dye signal from the red detection channel was obtained. This process is graphically illustrated in FIG. 32. Before the CRS algorithm, PM dye signal and a confounding FL dye cross-talk signal were detected in the concurrent Red channel (FIG. 32, left). After the CRS algorithm, the FL cross-talk was mitigated and only the true PM dye signal was detected in the Red channel (FIG. 32, right).

The consistency of the CR was tested and the concurrent imaging with CRS algorithm was qualitatively and quantitatively demonstrated.

Figure 33:
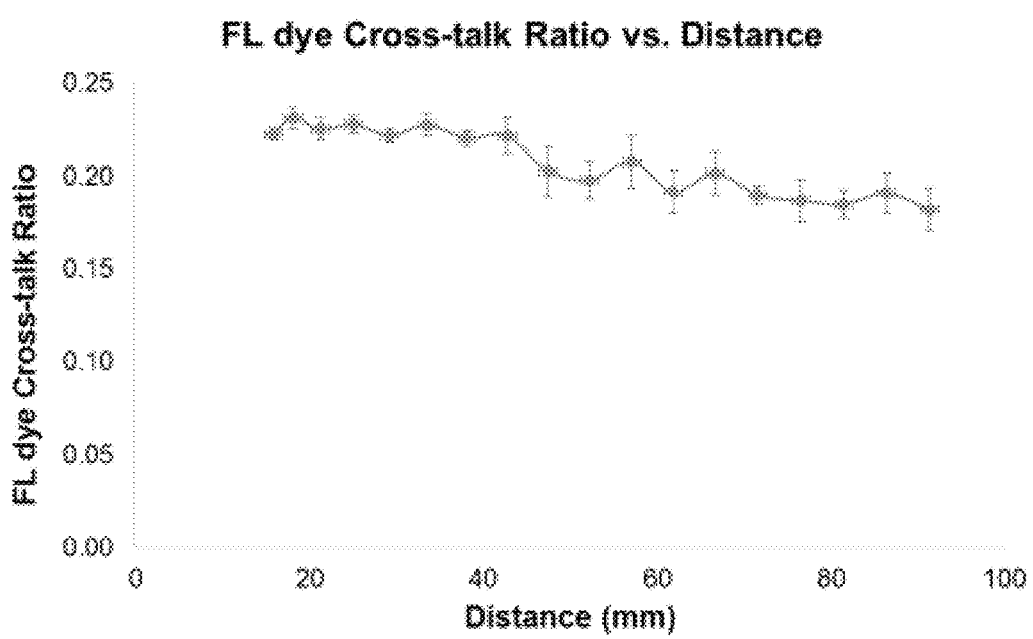
FIG. 33 shows the FL Cross-talk Ratio was plotted as a function of the distance between the distal end of the SFE endoscope and the fluorescence target in accordance with embodiments.

First, the consistency of the FL dye Cross-talk Ratio was tested by imaging the same FL target in the phantom over a range of distances between the SFE scope and the target. The CR was calculated and plotted as a function of the distance. The results, as shown in FIG. 33, demonstrated that the CR remained constant (0.225±0.012) within the 15-40 mm range and was relatively consistent (0.207±0.025) across the 15-95 mm distance range. Distances less than 15 mm were not included as the PMT detector was saturated, whereas at distances more than 95 mm, the signal intensity was too low to be measured.

Figure 34:
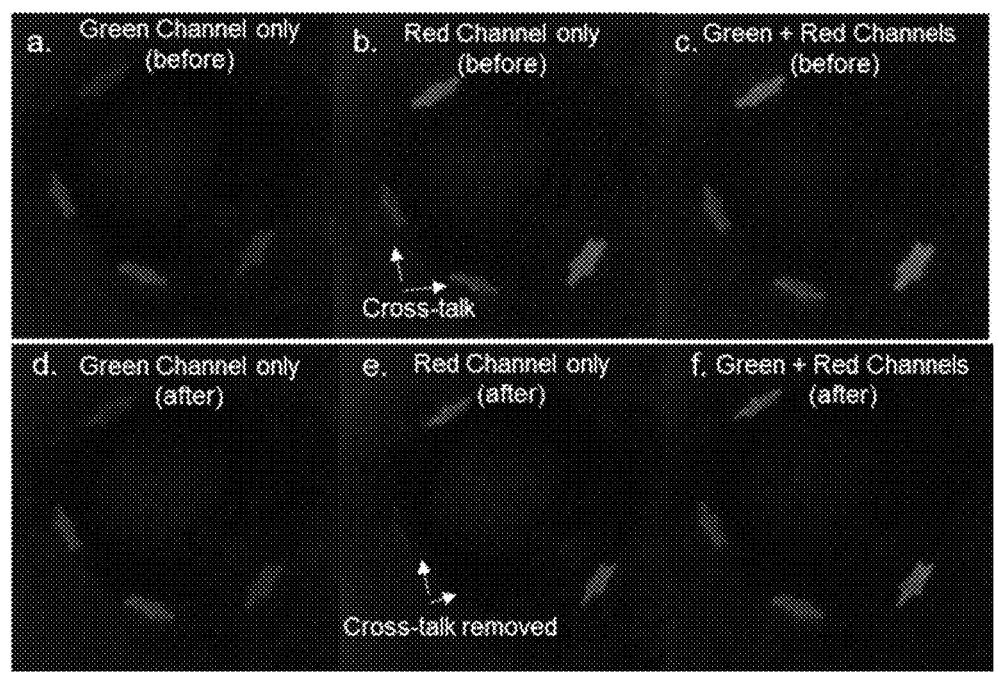
FIG. 34 shows concurrent multi-spectral fluorescence SFE imaging of the BE phantom at 30 Hz frame rate in accordance with embodiments.

During concurrent SFE dual-fluorescence imaging of FL and PM targets, before applying the FL Cross-talk Ratio Subtraction (CRS) algorithm, the FL-only targets exhibited erroneous fluorescence signal in the red channel (FIG. 34 (b)). After the CRS algorithm was applied, the confounding FL red channel signal was strongly attenuated, and the erroneous FL image was removed (FIG. 34 (e)).

This cross-talk also acted as a confounder and interfered with the green FL dye fluorescence display, causing it to appear with a subtle yellow shade FIG. 34 (c) by the addition of red channel bias to the green channel. The FL-only targets were therefore misrepresented in the display as two-dye targets since they had fluorescence signals from both the green and red detection channels. After applying the CRS algorithm, the confounding FL red channel contribution was removed and the green FL targets appeared in the correct green color (FIG. 34 (f)). The concurrent two-dye target imaging after applied the CRS algorithm in FIG. 34 (f) showed correctly rendered green FL, red PM, and orange two-dye display images. All images were single-frame raw video outputs from SFE imaging (80 degree field of view, 500-line resolution).

Figure 35A:
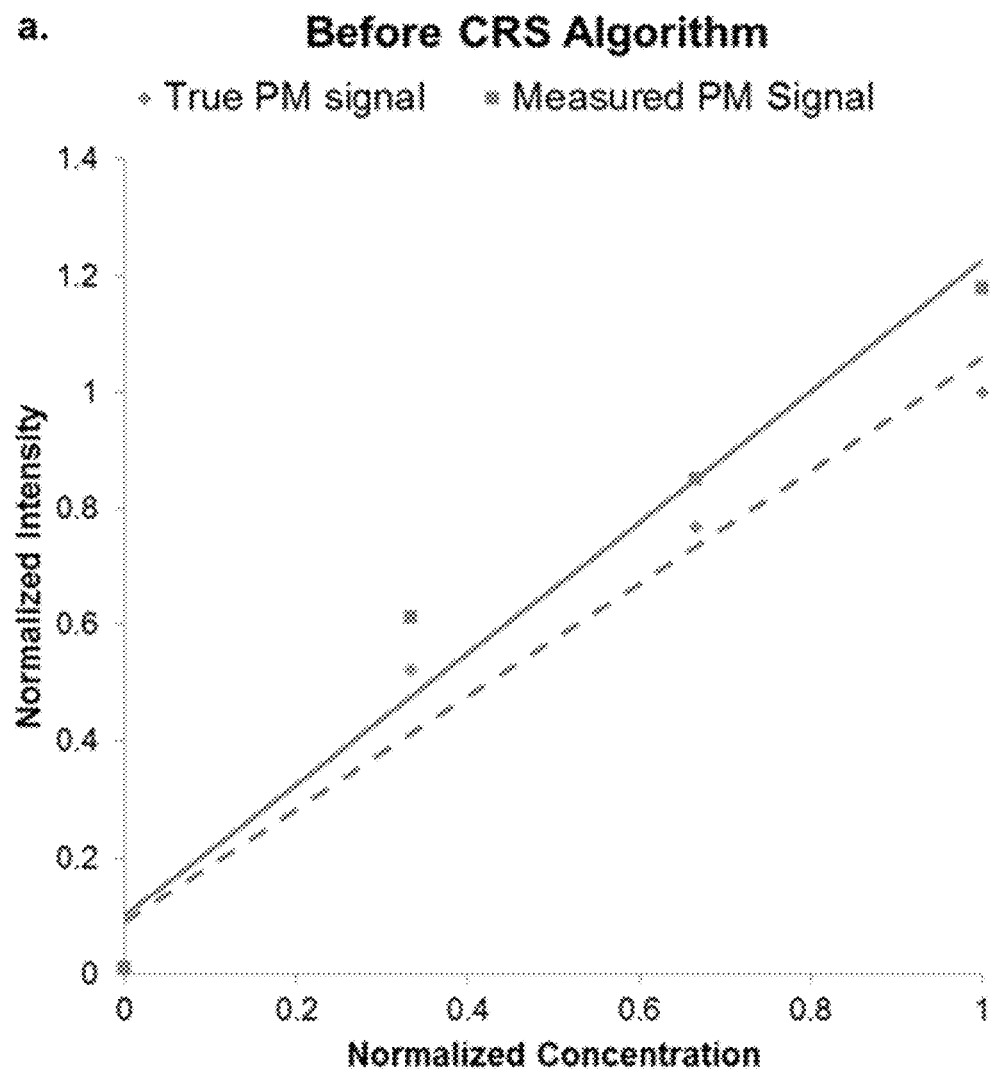
FIG. 35A shows a comparison of the signal from the red output channel to the true PM targets signal during concurrent multispectral fluorescence imaging before applying the CRS algorithm in accordance with embodiments.
Figure 35B:
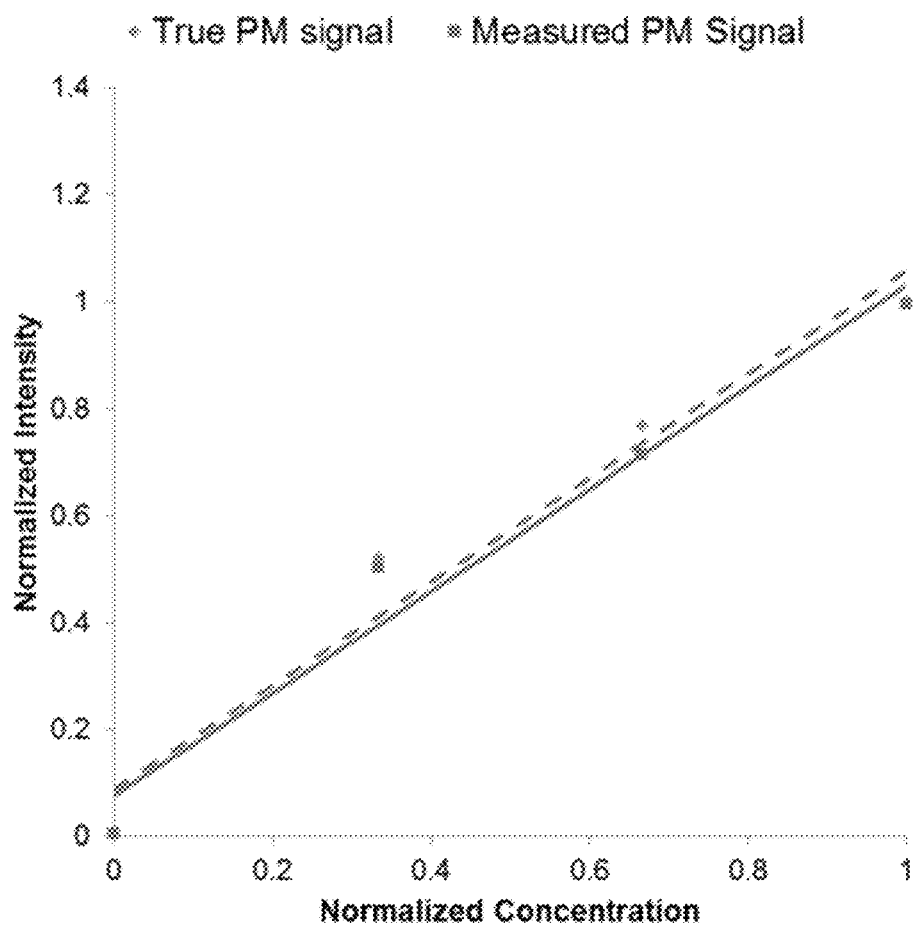
FIG. 35B shows a comparison of the signal from the red output channel to the true PM targets signal during concurrent multispectral fluorescence imaging after applying the CRS algorithm in accordance with embodiments.

Furthermore, quantitative measurements of fluorescence intensity dependence on dye concentration were conducted and the results are shown in FIG. 35A-35B. In this series of experiments, the PM dye with a range of concentrations (25, 50, 75 µmol/L respectively) were mixed with a constant concentration (100 µmol/L) of FL dye. A target with no dye-in-polymer was also used into obtain the system noise floor. The "true" PM signal was obtained by activating only the 532 nm laser and recording the red channel signal from the PM target. Initially, using concurrent laser excitation the red channel detector signal from the PM fluorescence was contaminated by the FL cross-talk signal (FIG. 35A). Therefore, in FIG. 35A, before the CRS algorithm, the fluorescence signal from the red detector channel deviated from the true PM curve. However, after applying the CRS algorithm (FIG. 35B), the red fluorescence signal closely matched the true PM fluorescence curve and the cross-talk signal was reduced by over 90%.

Sequential Multispectral Fluorescence Imaging

The sequential excitation of the R (635 nm), G (532 nm), B (442 nm) lasers was successfully implemented in the SFE system. As described in FIG. 14, for the output, a red reflectance image, a (PM red fluorescence+green reflectance) image, and a (FL green fluorescence+blue reflectance) image were sequentially received at a 30 Hz frame rate, resulting in 10 Hz frame rate for the combined two-dye fluorescence imaging.

Figure 36:
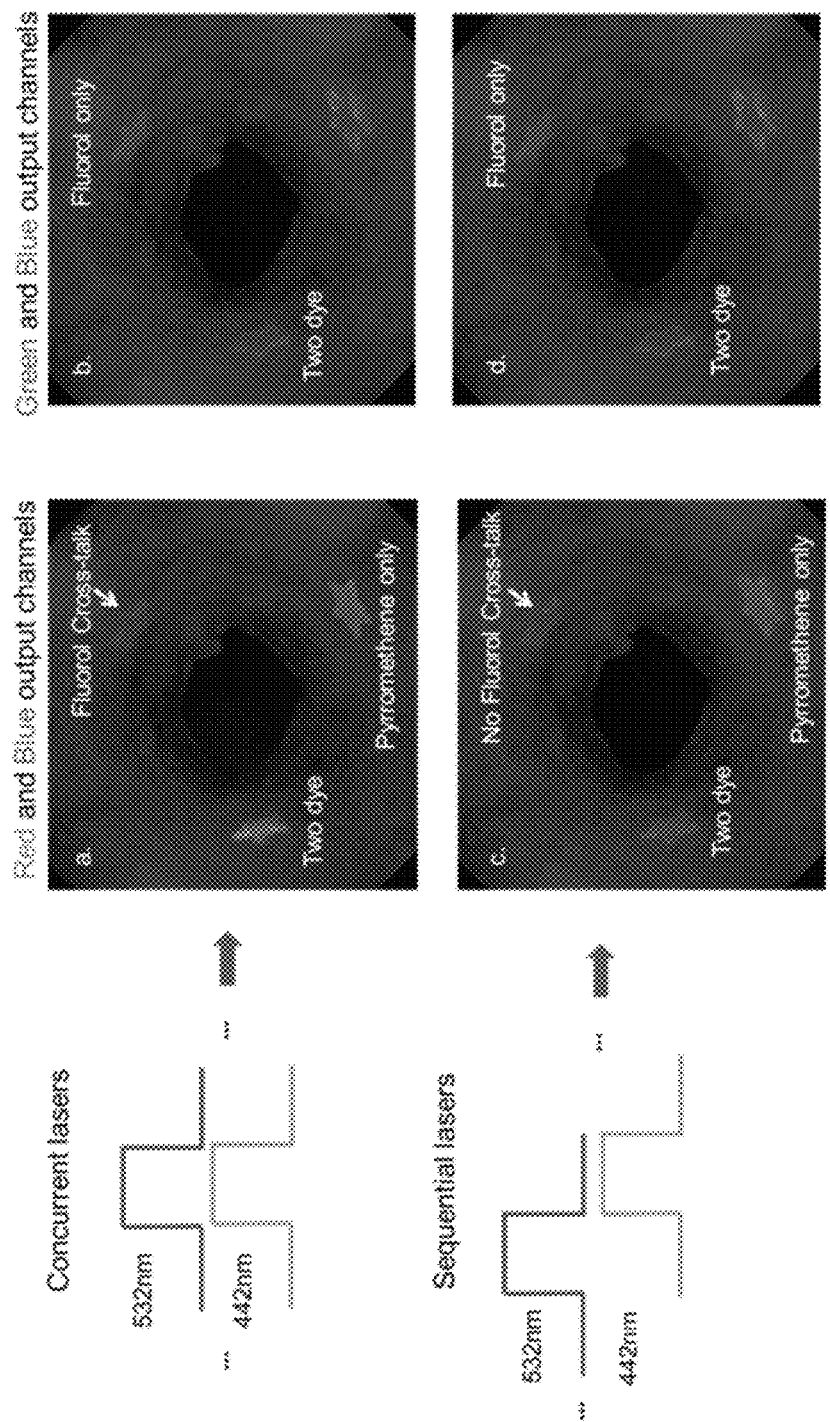
FIG. 36 shows concurrent laser excitation compared to sequential laser excitation results in accordance with embodiments.

In FIG. 36, the combined two-dye images contained fluorescence signals from the red and green detection channels with the reflectance signal from the blue detection channel. In concurrent laser excitation the FL cross-talk signal in the red output channel was present. However, under sequential laser excitation imaging temporal separation of the excitation produces uncontaminated images of the PM and FL dye emissions, with no cross-talk observed. As presented earlier, it is known that the FL and PM dyes do not have overlapping blue (442 nm) and green (532 nm) excitation and therefore sequential excitation is sufficient to separate the overlapping dye emissions.

In the current study, the red reflectance image was also received at every cycle and can be used as an option for Distance Compensation: a pixel-by-pixel intensity computation using a non-linear ratio of the fluorescence and red channel reflectance ($F/(R^{1.5})$).

Cross-talk is a confounding factor when two or more spectrally intersecting fluorescent dyes are used in endoscopic diagnostic imaging. Approaches to mitigate the fluorescence cross-talk were tested using a 1.2 mm diameter wide field-of-view endoscope (SFE). The solutions evaluated in the current study were: (1) image stitching, (2) Cross-talk Ratio Subtraction (CRS) algorithm, and (3) frame-sequential imaging.

In the first approach of stitching to merge multiple fluorescence video frames into a panoramic image, cross-talk was avoided because each fluorescent target was illuminated with one laser excitation wavelength and the corresponding emission was captured in the appropriate detection channel. The resultant mosaic map display of the lower esophagus showed distinguishable green FL-only, red PM-only, and orange two-dye targets with no emission cross-talk observed.

Meanwhile, the stitched multi-spectral fluorescence mosaic encompassed a much wider view of the observation area than that captured from a single endoscopic frame, and could be used for intraoperative navigation for hot-spots biopsy, or saved as the patient electronic medical record for longitudinal surveillance. Moreover, the mosaic map can also be used for extended review by the physicians without photobleaching decreasing the fluorescence signal. The current stitching software generates results within 1 minute with good spatial registration score, and its performance can be improved using higher processing speed.

However, there are drawbacks in implementing the stitching approach. Firstly, it does not offer true concurrent imaging and visualization of multi-spectral fluorescence targets, instead, it requires the running of multiple individual scans, which can be slow for clinical practice. This delay can also complicate the image stitching processing, where the stitching algorithm uses shared anatomical features from the reflectance images and assumes that these features remain static between different scans; however, in a typical in vivo setting, unpredictable motions, specular reflections from saline solutions or mucous, and other factors could cause feature shifts to appear in each scan, and therefore, a more robust algorithm for this approach would be needed for in vivo implementation.

The second approach, concurrent imaging with Cross-talk Ratio Subtraction algorithm (CRS), performs simultaneous imaging where all fluorescence species are illuminated and their fluorescence emissions collected at the same time. In this case the cross-talk signal was successfully attenuated in real-time by applying the CRS algorithm (described in Equation 1, 2, and FIG. 32). The algorithm was applied to the SFE red detection channel during a pre-scan calibration. The FL dye Cross-talk Ratio (CR) remained consistent over a range of imaging distances (FIG. 33). Specifically, the ratio remained constant (0.225±0.012) within a distance of 15-40 mm and kept relatively consistent (0.207±0.025) across a distance of 15-95 mm. For in vivo clinical practice in the luminal esophagus, a distance under 40 mm is a realistic working distance between the endoscope and region of interest under scrutiny by the clinician. The results also showed that the confounding FL dye cross-talk signal was strongly (>90%) reduced (FIG. 34), and quantitative analysis showed that the fluorescence signal closely matched the "true" PM dye fluorescence intensity (FIG. 35B).

Compared to the image stitching approach, the concurrent imaging approach provides visualization of multi-spectral fluorescent targets/hot-spots simultaneously and in real-time. This concurrent method is beneficial for wide-field endoscopic imaging and image-guided biopsies. Viewing coincident emission signatures from multiple dyes will provide a more accurate molecular diagnosis than a single fluorescent marker. Moreover, the concurrent imaging approach is more robust and accurate than the image stitching approach for in vivo settings since the removal of dye cross-talk is not affected by unpredictable motion or specular reflections that complicate image indexing.

However, there are some drawbacks to the concurrent imaging approach in a clinical setting. First, a pre-scan calibration is needed to calculate the cross-talk ratio by imaging a fluorescent standard. Additionally, the gain and offsets on the light detection PMTs and digital outputs must be maintained at a constant level between calibration and measurement scans. This is an extra step that must be automated in a clinical or in vivo study. Meanwhile, as shown in FIG. 33, the FL Cross-talk Ratio remained constant within the distance range of 15-40 mm, but this ratio fluctuated slightly and decreased when extended to a 95 mm distance. This irregularity could be a drawback if the distance accuracy of the fluorescence intensity must be maintained over a very wide range.

The third approach, frame-sequential imaging, was carried out by timed excitation and light collection from only one fluorophore species at a time. This temporal separation of laser illumination and light collection minimizes cross-talk in a manner similar to the image stitching approach; however, instead of collecting the emission signal separately and processing groups of image frames, the frame-sequential imaging method cycles through all of the laser excitation and dye emission combinations at 30 Hz. Therefore, the relatively stationary position of organs and tissue during the fast frame rate imaging process removes the need for image registration. Meanwhile, visualization of multi-spectral fluorescence hot-spots can be achieved by combining each cycle of image outputs: red PM dye fluorescence, green FL dye fluorescence and blue reflectance into combined RGB image frames which can be displayed in real-time during the endoscopy procedure.

In standard RGB operation, the SFE refresh rate is 30 Hz since the image is a composite of all three concurrent colors. However, in the sequential imaging mode the SFE system runs at a 10 Hz frame rate (or 15 Hz if Distance Compensation algorithm is not applied) for each of the individual fluorescence and reflectance frames. Therefore, when the number of fluorophores increases, the frame rate for the sequential images must increase by a factor somewhat larger than the number of fluorophores in order to display a real time view that adapts to body and endoscope movements. Imaging with a low frame rate will be limited to viewing objects that undergo very slow motions, which may not be adequate for clinical endoscopy.

The summary of the three proposed approaches are listed below in Table 1 below:

TABLE 1

Comparative Benefits of three solutions to the problem of fluorescence cross-talk of spectrally intersecting fluorescence signals

| Solution | Benefit |
|---|---|
| (1) Image Stitching | a. Avoids dye cross-talk<br>b. Can be used for extended review and less susceptible to fluorescence photo-bleaching<br>c. Can be saved as patient record |
| (2) Concurrent Imaging Using CRS Algorithm | a. Reduces dye cross-talk<br>b. Real time<br>c. Compatible with in vivo clinical scenario |
| (3) Frame-Sequential Imaging | a. Avoids dye cross-talk<br>b. No pre-scan calibration is required<br>c. Near real-time multispectral fluorescence imaging<br>d. Compatible with in vivo scenario |

Achieving a high target-to-background ratio (T/B) is a driving factor in the clinical realization of optical molecular imaging. For in vivo optical imaging using exogenous targeted contrast agents, the non-specific binding and material accumulation (pooling) of contrast agent and tissue autofluorescence (AF) can cause a significant decrease in the T/B. AF is the major contributor to the background signal in topical application of fluorescence probes to epithelial tissue since non-specific accumulation is minimized in this situation.

The approaches described herein can also reduce the background tissue autofluorescence signals that degrade T/B. It has been reported that tissue AF signals can mask exogenous molecular probe fluorescence, which can limit the in vivo T/B. In the esophagus, stromal collagen is believed to be primarily responsible for the AF signal especially when excited in the near-UV to blue spectral range. Therefore, collagen AF could be a major confounder for commonly used fluorophores such as Coumarin, DEAC, and FITC. Molecular imaging studies of mouse colon cancer using a FITC conjugated peptide marker produced a T/B of only 2-3 as a result of AF. Reducing the AF background signal can increase this T/B ratio. Eliminating the AF background using chemical agents such as Sudan black has been reported in confocal laser scanning microscopy but not applicable for in vivo clinical endoscopy. On the endoscopic imaging device, if a detection channel was designated for autofluorescence, the AF image could be subtracted out from the fluorescent marker channel using either concurrent or frame sequential imaging methods. These improvements could lead to an enhanced target-to-background ratio.

Figure 37A:
FIG. 37A shows a synthetic autofluorescence phantom with a star-shaped fluorescence target captured by the SFE between 500-540 nm after excitation at 442 nm in accordance with embodiments.
Figure 37B:
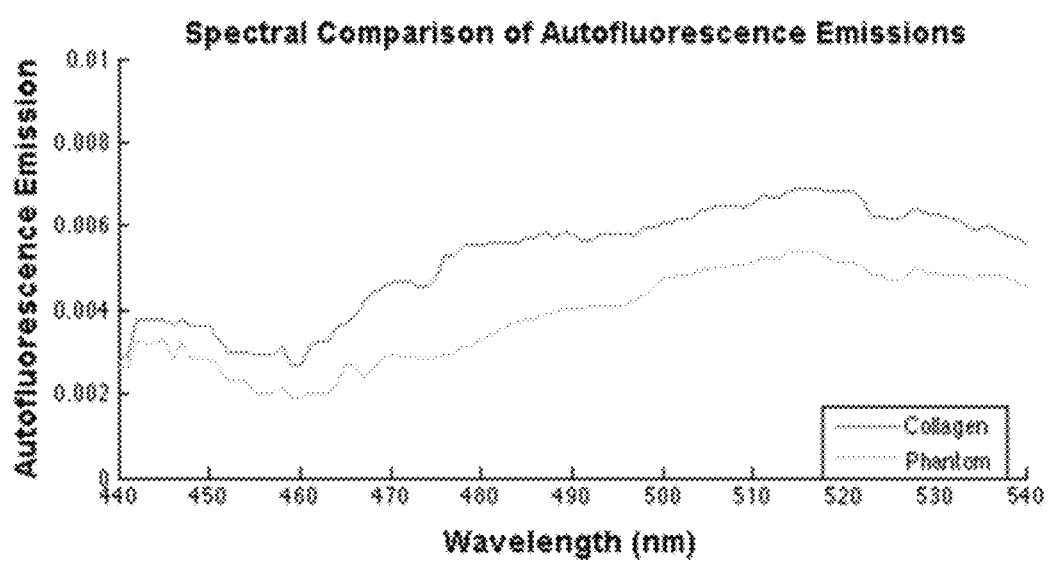
FIG. 37B shows a comparison of AF emissions shows that the phantom fluorescence emission is similar to that of pure collagen in accordance with embodiments.

To test this concept an AF feature was added to a color matched BE phantom (FIG. 37A). The autofluorescence background feature was added to the Barrett's esophagus (BE) phantom. In summary, collagen fibers were converted to powder through heating, drying, and mechanical processing. Double-distilled water (ddH2O) was added and the resulting paste was evenly applied over the phantom subsurface to simulate the stromal collagen layer. After drying, a paint simulated healthy and BE mucousal layer was applied evenly over the collagen layer and allowed to dry. Comparison of AF emissions shows that the phantom fluorescence emission is similar to that of pure collagen (FIG. 37B). Concerns that the excitation fiber exhibits autofluorescence was tested using a spectrometer (USB2000+, Ocean Optics, Inc). No autofluorescence signal was detected with the laser excitation power used in the current study.

The star shape depicted in FIG. 37A is a FL-in-polymer dye target with a concentration of 1 μM, whereas the background fluorescence is due to the embedded collagen AF. Image analysis shows the target to background signal ratio was 4:1. Autofluorescence background subtraction was shown to enhance image contrast for tumor detection, and it is embedded software technology in the commercially available IVIS benchtop system. An estimate of the proposed T/B signal improvement was obtained by subtracting the AF background in FIG. 37B. The T/B increased from 4 to ≥10 following subtraction of the AF background. This enhancement elevates the performance of UV-blue excited fluorophores (e.g. FITC) to the level achieved with red and NIR dyes which are excited and fluoresce in spectral regions considered more immune from AF. Indocyanine green, the only FDA approved NIR fluorescent dye, has a hydrophobic, large heptamethine interior that is surrounded by a negatively charged surface shell. This molecular arrangement will result in comparatively high nonspecific binding and may degrade the T/B advantage of ICG especially in systemic applications. On the other hand, this charge distribution pattern is not present in the FDA approved FITC dye that has a peak excitation wavelength at 488 nm. Less nonspecific binding of FITC combined with mitigation of its AF signal makes this dye a more viable choice for molecular imaging. Gaining FDA approval for any new dye is a very costly and time consuming endeavor and to date no other fluorescent dyes have received clearance for use in routine human clinical procedures. Therefore, any measure that enhances the performance of existing FDA approved dyes has significant translational impact for molecular imaging technology.

Situations where cross-talk occurs for both dye excitation and emission, or cases with 'extreme' cross-talk, where the two dyes' emissions completely intertwine, were not studied, as these situations can be avoided by selecting alternate dye labels. The probes which are likely to be used with the SFE for in vivo study in the near future are Coumarin (DEAC), Fluorescein (FITC), 5-Carboxytetramethylrhodamine (5-TAMRA), Cyanine (Cy5.5), 5-Aminolevulinic Acid Hydrochloride (5-ALA) and Indocyanine green (ICG) dyes. These dyes exhibit moderate levels of intersection compatible with the three proposed spectral overlap solutions. In addition, since the SFE excitation light source is laser based, the excitation bandwidth is less than 2 nm and therefore, in most cases, the excitation overlap can be circumvented. These dyes exhibit moderate levels of intersection compatible with the three proposed spectral overlap solutions. For cases with extreme emission spectrum overlap, sophisticated algorithms such as linear-unmixing for laser scanning microscopy have been proposed and applied. However, due to the additional data collection and processing time required, the linear-unmixing approach might not be suitable for real time wide-field fluorescence endoscopic imaging. In the current study, the image stitching approach and the frame-sequential imaging approach could be applied to solve cross-talk where the emission spectrum suffers from extreme overlap, by separately illuminating each fluorophore, receive and composite near real-time multi-spectral fluorescence imaging. Fluorescence life-time imaging is another feasible approach to delineate highly overlapped fluorescence. Recently fluorescence life-time imaging was applied to delineate fluorescent species, and detection of early cancer lesions. Combining SFE imaging with time-resolved fluorescence spectroscopy was recently reported for biomedical assessment of the bile duct and fluorescence life-time imaging holds potential for the delineation of overlapped multi-spectral fluorophores.

Studies using quantum dots (QDs) for multi-spectral fluorescence imaging have also been reported. Due to the uncertain toxicity and unknown side-effects, QDs are currently not FDA-approved and are less likely to be used in human trials than organic dyes. QDs have a symmetric and Gaussian-like emission spectral profile, and therefore less cross-talk than organic dyes. However, in applications where multiple QDs are imaged simultaneously, emission cross-talk can still occur, and the proposed solutions are applicable to spectral overlap of multi-spectral fluorescence nanoparticle imaging as well.

In conclusion, three different approaches were evaluated for the removal of fluorophore emission cross-talk in wide-field multi-fluorophore molecular imaging: Image stitching, Cross-talk Ratio Subtraction (CRS) algorithm, and frame-sequential imaging. To evaluate these solutions, an in vitro phantom with fluorophore emission cross-talk was constructed. The results showed that fluorophore emission cross-talk could be significantly reduced or successfully avoided. At present, the concurrent imaging method is viable for early stage cancer detection in vivo with the wide-field multi-fluorophore SFE imaging device with addition of an initialization step not unlike the white-balancing step for commercial endoscopes. Furthermore, a means to enhance fluorescence target-to-background ratio that is directly applicable to FITC (FDA-approved dye) by the reduction of autofluorescence background signal was demonstrated.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A wide field spectral imaging apparatus, comprising:
   a display;
   a wide field spectral imager configured for imaging an object with at least a reference beam and a target beam, wherein the wide field spectral imager includes:
      a first and a second fluorescence excitation light source, wherein the first fluorescence excitation light source is adapted to emit the reference beam, and wherein the second fluorescence excitation light source is adapted to emit the target beam; and
   a processor coupled to the wide field spectral imager, the processor comprising instructions that when executed by the processor causes the apparatus to perform operations including:
      receiving a background fluorescence signal and a target fluorescence signal respectively in response to illuminating the object with the reference beam and the target beam:
      enhancing the target fluorescence signal by subtracting the background fluorescence signal multiplied by a pre-calibrated constant ratio from the target fluorescence signal; and
      displaying an image of the object with the display, wherein the image is based, at least in part, on the enhanced target fluorescence signal.

2. The apparatus of claim 1, wherein the first fluorescence light source has a first wavelength, wherein the second fluorescence light source has a second wavelength, and wherein the first wavelength is different than the second wavelength.

3. The apparatus of claim 2, wherein the first wavelength is less than the second wavelength.

4. The apparatus of claim 1, wherein the wide field spectral imager is configured to image the object at one or more of a varying distance and a varying angle.

5. The apparatus of claim 1, wherein the wide field spectral imager further includes an offset setting and a gain setting, and wherein the constant ratio is pre-calibrated based on one or more of the offset setting and the gain setting.

6. The apparatus of claim 1, wherein the processor comprises additional instructions that when executed causes the apparatus to perform further operations including:
   computing the constant ratio as A/B, wherein A comprises an intensity of the target fluorescence signal within a target spectral range of an emission spectrum, and wherein B comprises an intensity of the background fluorescence signal within a reference spectral range of the emission spectrum.

7. The apparatus of claim 6, wherein the intensity within the target spectral range comprises an average of spectral intensities selected from within the target spectral range, and the intensity within the reference spectral range comprises an average of spectral intensities selected from within the reference spectral range.

8. The apparatus of claim 6, wherein the processor comprises additional instructions that when executed causes the apparatus to perform further operations including:
   quantifying the background fluorescence signal as corresponding to an intensity within a reference spectral range of the emission spectrum;
   quantifying the target fluorescence signal as corresponding to an intensity within a target spectral range of the emission spectrum, and wherein the reference spectral range is different than the target spectral range;
   calculated a corrected target fluorescence signal by subtracting the background fluorescence signal multiplied by the pre-calibrated constant ratio from the target fluorescence signal,
   generating the image of the object based, at least in part, on a normalized intensity of the corrected target fluorescence signal.

9. The apparatus of claim 1, wherein the wide field spectral imager is configured to image the object by illuminating the object with reference beam and the target beam concurrently or sequentially for the apparatus to receive the background fluorescence signal and the target fluorescence signal concurrently or sequentially, respectively.

10. The apparatus of claim 1, wherein the processor comprises additional instructions that when executed causes the apparatus to perform further operations including:
   correcting the target fluorescence signal in response to a concurrent reflectance signal.

11. The apparatus of claim 1, wherein the processor comprises additional instructions that when executed causes the apparatus to perform further operations including:
   correcting the target fluorescence signal in response to a concurrent reflectance signal related to a distance of the object from a light collection portion of the wide field spectral imager.

12. The apparatus of claim 1, wherein the processor comprises additional instructions that when executed causes the apparatus to perform further operations including:

receiving a reflectance signal from the illuminating related to a distance of the object from a light collection portion of the wide field spectral imager; and computing a distance compensated fluorescence signal intensity as F/(Rx), wherein F is a raw fluorescent signal intensity included in the target fluorescence signal, R is a raw reflectance signal intensity included in the reflectance signal, and x is an empirically determined number.

13. The apparatus of claim 12, wherein the empirically determined number is in the range from 1.1 to 2.9.

14. The apparatus of claim 13, wherein the empirically determined number is in the range from 1.3 to 1.7.

15. The apparatus of claim 12, wherein the processor comprises additional instructions that when executed causes the apparatus to perform further operations including:

computing the distance compensated fluorescence signal intensity for each pixel in an image.

16. The apparatus of claim 1, wherein the processor comprises additional instructions that when executed causes the apparatus to perform further operations including:

correcting the target fluorescence signal in response to a phantom of the object.

17. The apparatus of claim 1, wherein the wide field spectral imager is further configured to provide a reflectance signal, and wherein the processor comprises additional instructions that when executed causes the apparatus to perform additional operations including:

providing an image of the reflectance signal in co-registration with an image of the target fluorescence signal.

18. The apparatus of claim 1, wherein the processor comprises additional instructions that when executed causes the apparatus to perform operations including:

receiving a reflectance signal concurrently or sequentially with the target fluorescence signal;

displaying an image of the object in which the reflectance signal is co-registered with the target fluorescence signal.

19. The apparatus of claim 18, wherein the wide field spectral imager provides a first image of the target fluorescence signal and a second image of the reflectance signal, and wherein the processor comprises additional instructions that when executed causes the apparatus to perform further operations including:

generating a first projection of the first image onto a three dimensional surface model of the object; and generating a second projection of the second image onto the three dimensional surface model of the object.

20. The apparatus of claim 19, wherein the processor comprises additional instructions that when executed causes the apparatus to perform further operations including:

unwrapping the first projection and the second projection of the three dimensional surface model of the object;

generating a first anatomical map by the unwrapping of the first projection;

generating a second anatomical map by the unwrapping of the second projection; and co-registering the first anatomical map with the second anatomical map.

21. A wide field spectral imaging method, comprising:

receiving a target fluorescence signal and a background fluorescence signal by illuminating an object with a first and a second fluorescence excitation light source included in a wide field spectral imager;

enhancing the target fluorescence signal by subtracting the background fluorescence signal multiplied by a pre-calibrated constant ratio from the target fluorescence signal; and displaying an image of the object based, at least in part, on the target fluorescence signal after the subtracting.

22. The method of claim 21, further comprising:

quantifying the target fluorescence signal as corresponding to an intensity with a target spectral range of an emission spectrum;

quantifying the background fluorescence signal as corresponding to an intensity within a reference spectral range of the emission spectrum, wherein the reference spectral range is different than the target spectral range; and generating the image of the object corresponding to a normalized intensity of the enhanced target fluorescence.

23. The method of claim 21, further comprising:

receiving a reflectance signal in response to the illuminating, wherein the reflectance signal is related to a distance of the object from a light collection portion of the wide field spectral imager; and computing a distance compensated fluorescence signal intensity defined as F/(Rx), wherein F is a raw fluorescent signal intensity included in the target fluorescence signal, R is a raw reflectance signal intensity included in the reflectance signal, and x is an empirically determined number.

* * * * *